US010583250B2

(12) United States Patent
Mazlish et al.

(10) Patent No.: US 10,583,250 B2
(45) Date of Patent: Mar. 10, 2020

(54) SYSTEM AND METHOD FOR ADJUSTING INSULIN DELIVERY

(71) Applicant: Bigfoot Biomedical, Inc., Milpitas, CA (US)

(72) Inventors: Bryan Mazlish, Palo Alto, CA (US); Lane Desborough, Thousand Oaks, CA (US); Ross Naylor, Fullerton, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 173 days.

(21) Appl. No.: 15/870,674

(22) Filed: Jan. 12, 2018

(65) Prior Publication Data

US 2018/0200438 A1 Jul. 19, 2018

Related U.S. Application Data

(60) Provisional application No. 62/446,244, filed on Jan. 13, 2017.

(51) Int. Cl.
*A61M 5/172* (2006.01)
*G16H 20/17* (2018.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
CPC ............ A61M 5/1723; A61M 5/14276; A61M 5/1413; A61M 5/1452; A61M 5/31525; A61M 5/20; A61M 5/24; A61M 5/14244; A61M 5/14248; A61M 5/172; A61M 5/142; A61K 38/28; A61B 5/14532; A61B 5/7275; A61B 5/1495; A61B 5/0002;
(Continued)

(56) References Cited

U.S. PATENT DOCUMENTS 4,464,170 A 8/1984 Clemens et al.
6,379,301 B1 4/2002 Worthington et al.
(Continued)

FOREIGN PATENT DOCUMENTS

JP 2008-545454 A 12/2008
JP 2010-531678 A 9/2010
(Continued)

OTHER PUBLICATIONS

David A. Copp, Ravi Gondhalekar, and Joao P. Hespanha, Simultaneous Model Predictive Control and 5 Moving Horizon Estimation for Blood Glucose Regulation in Type 1 Diabetes, Optimal Control Applications and Methods, Wiley InterScience, DOI: 10.1002/oca, pp. 1-15, Oct. 2016.
(Continued)

*Primary Examiner* — Manuel A Mendez
(74) *Attorney, Agent, or Firm* — TraskBritt

(57) ABSTRACT

The embodiments described herein may relate to methods and systems for adjusting insulin delivery. Some methods and systems may be configured to adjust insulin delivery to personalize automated insulin delivery for a person with diabetes. Such personalization may include adjusting user specific dosage parameters in response to one or more back-filled time segments associated with a diurnal time block.

15 Claims, 27 Drawing Sheets

(51) Int. Cl.
*A61M 5/142* (2006.01)
*A61B 5/145* (2006.01)
*A61B 5/00* (2006.01)
*A61M 5/315* (2006.01)
*G16H 40/63* (2018.01)
*A61K 38/28* (2006.01)
*A61M 5/00* (2006.01)

(52) U.S. Cl.
CPC .... *A61M 5/14248* (2013.01); *A61M 5/31568* (2013.01); *G16H 20/17* (2018.01); *G16H 40/63* (2018.01); *A61K 38/28* (2013.01); *A61M 5/003* (2013.01); *A61M 2205/3379* (2013.01); *A61M 2205/35* (2013.01); *A61M 2205/3569* (2013.01); *A61M 2205/3584* (2013.01); *A61M 2205/502* (2013.01); *A61M 2205/52* (2013.01); *A61M 2205/8206* (2013.01); *A61M 2230/201* (2013.01)

(58) Field of Classification Search
CPC ............... A61B 5/4839; G06F 19/3475; G06F 19/3481; G06F 19/3468; G06F 19/3456; G16H 50/20; G16H 50/50; G16H 20/17
See application file for complete search history.

(56) References Cited

U.S. PATENT DOCUMENTS

| | | |
|---|---|---|
| 6,544,212 B2 | 4/2003 | Galley et al. |
| 6,551,276 B1 | 4/2003 | Mann et al. |
| 6,554,798 B1 | 4/2003 | Mann et al. |
| 6,558,351 B1 | 5/2003 | Steil et al. |
| 6,599,281 B1 | 7/2003 | Struys et al. |
| 6,605,072 B2 | 8/2003 | Struys et al. |
| 6,740,072 B2 | 5/2004 | Starkweather et al. |
| 6,799,149 B2 | 9/2004 | Hartlaub |
| 6,827,702 B2 | 12/2004 | Lebel et al. |
| 6,872,200 B2 | 3/2005 | Mann et al. |
| 6,873,268 B2 | 3/2005 | Lebel et al. |
| 6,936,029 B2 | 8/2005 | Mann et al. |
| 6,979,326 B2 | 12/2005 | Mann et al. |
| 6,997,920 B2 | 2/2006 | Mann et al. |
| 7,025,743 B2 | 4/2006 | Mann et al. |
| 7,060,059 B2 | 6/2006 | Keith et al. |
| 7,066,910 B2 | 6/2006 | Bauhahn et al. |
| 7,109,878 B2 | 9/2006 | Mann et al. |
| 7,133,329 B2 | 11/2006 | Skyggebjerg et al. |
| 7,179,226 B2 | 2/2007 | Crothall et al. |
| 7,204,823 B2 | 4/2007 | Estes et al. |
| 7,220,240 B2 | 5/2007 | Struys et al. |
| 7,267,665 B2 | 9/2007 | Steil et al. |
| 7,354,420 B2 | 4/2008 | Steil et al. |
| 7,402,153 B2 | 7/2008 | Steil et al. |
| 7,404,796 B2 | 7/2008 | Ginsberg |
| 7,491,187 B2 | 2/2009 | Van et al. |
| 7,547,281 B2 | 6/2009 | Hayes et al. |
| 7,569,030 B2 | 8/2009 | Lebel et al. |
| 7,651,845 B2 | 1/2010 | Doyle, III et al. |
| 7,704,226 B2 | 4/2010 | Mueller et al. |
| 7,734,323 B2 | 6/2010 | Blomquist et al. |
| 7,766,829 B2 | 8/2010 | Sloan et al. |
| 7,785,313 B2 | 8/2010 | Mastrototaro |
| 7,806,853 B2 | 10/2010 | Wittmann et al. |
| 7,806,854 B2 | 10/2010 | Damiano et al. |
| 7,815,602 B2 | 10/2010 | Mann et al. |
| 7,819,843 B2 | 10/2010 | Mann et al. |
| 7,850,641 B2 | 12/2010 | Lebel et al. |
| 7,967,812 B2 | 6/2011 | Jasperson et al. |
| 7,976,492 B2 | 7/2011 | Brauker et al. |
| 8,062,249 B2 | 11/2011 | Wilinska et al. |
| 8,088,098 B2 | 1/2012 | Yodfat et al. |
| 8,105,268 B2 | 1/2012 | Lebel et al. |
| 8,152,789 B2 | 4/2012 | Starkweather et al. |
| 8,206,350 B2 | 6/2012 | Mann et al. |
| 8,208,984 B2 | 6/2012 | Blomquist et al. |
| 8,226,556 B2 | 7/2012 | Hayes et al. |
| 8,267,893 B2 | 9/2012 | Moberg et al. |
| 8,273,052 B2 | 9/2012 | Damiano et al. |
| 8,352,011 B2 | 1/2013 | Van et al. |
| 8,417,311 B2 | 4/2013 | Rule |
| 8,439,834 B2 | 5/2013 | Schmelzeisen-Redeker et al. |
| 8,439,897 B2 | 5/2013 | Yodfat et al. |
| 8,454,576 B2 | 6/2013 | Mastrototaro et al. |
| 8,460,231 B2 | 6/2013 | Brauker et al. |
| 8,480,655 B2 | 7/2013 | Jasperson et al. |
| 8,548,544 B2 | 10/2013 | Kircher et al. |
| 8,551,045 B2 | 10/2013 | Sie et al. |
| 8,560,082 B2 | 10/2013 | Wei |
| 8,560,131 B2 | 10/2013 | Haueter et al. |
| 8,562,587 B2 | 10/2013 | Kovatchev et al. |
| 8,579,879 B2 | 11/2013 | Palerm et al. |
| 8,585,591 B2 | 11/2013 | Sloan et al. |
| 8,585,637 B2 | 11/2013 | Wilinska et al. |
| 8,585,638 B2 | 11/2013 | Blomquist |
| 8,615,366 B2 | 12/2013 | Galley et al. |
| 8,694,115 B2 | 4/2014 | Goetz et al. |
| 8,706,691 B2 | 4/2014 | McDaniel et al. |
| 8,718,949 B2 | 5/2014 | Blomquist et al. |
| 8,721,585 B2 | 5/2014 | Brauker et al. |
| 8,727,982 B2 | 5/2014 | Jennewine |
| 8,734,428 B2 | 5/2014 | Blomquist |
| 8,747,315 B2 | 6/2014 | Brauker et al. |
| 8,777,896 B2 | 7/2014 | Starkweather et al. |
| 8,784,369 B2 | 7/2014 | Starkweather et al. |
| 8,784,370 B2 | 7/2014 | Lebel et al. |
| 8,795,224 B2 | 8/2014 | Starkweather et al. |
| 8,876,755 B2 | 11/2014 | Taub et al. |
| 8,945,094 B2 | 2/2015 | Nordh |
| 8,977,504 B2 | 3/2015 | Hovorka |
| 8,992,475 B2 | 3/2015 | Mann et al. |
| 9,056,165 B2 | 6/2015 | Steil et al. |
| 9,320,471 B2 | 4/2016 | Hayes et al. |
| 9,333,298 B2 | 5/2016 | Kim et al. |
| 9,415,157 B2 | 8/2016 | Mann et al. |
| 9,474,855 B2 | 10/2016 | McCann et al. |
| 9,480,796 B2 | 11/2016 | Starkweather et al. |
| 9,486,172 B2 | 11/2016 | Cobelli et al. |
| 9,486,578 B2 | 11/2016 | Finan et al. |
| 2003/0060765 A1 | 3/2003 | Campbell et al. |
| 2003/0114836 A1 | 6/2003 | Estes et al. |
| 2003/0181852 A1 | 9/2003 | Mann et al. |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0212364 A1 | 11/2003 | Mann et al. |
| 2005/0171513 A1 | 8/2005 | Mann et al. |
| 2006/0253067 A1 | 11/2006 | Staib et al. |
| 2008/0033357 A1 | 2/2008 | Mann et al. |
| 2008/0097289 A1 | 4/2008 | Steil et al. |
| 2008/0147004 A1 | 6/2008 | Mann et al. |
| 2008/0147050 A1 | 6/2008 | Mann et al. |
| 2008/0183060 A1 | 7/2008 | Steil et al. |
| 2008/0208113 A1 | 8/2008 | Damiano et al. |
| 2008/0269714 A1 | 10/2008 | Mastrototaro et al. |
| 2008/0319384 A1 | 12/2008 | Yodfat et al. |
| 2009/0149728 A1 | 6/2009 | Van et al. |
| 2009/0164239 A1 | 6/2009 | Hayter et al. |
| 2009/0164251 A1 | 6/2009 | Hayter |
| 2010/0082167 A1 | 4/2010 | Haueter et al. |
| 2010/0125241 A1 | 5/2010 | Prud et al. |
| 2010/0137788 A1 | 6/2010 | Braithwaite et al. |
| 2010/0138197 A1 | 6/2010 | Sher |
| 2010/0249561 A1 | 9/2010 | Patek et al. |
| 2010/0256466 A1 | 10/2010 | Shekalim et al. |
| 2010/0262117 A1 | 10/2010 | Magni et al. |
| 2011/0015511 A1 | 1/2011 | Bousamra et al. |
| 2011/0208156 A1 | 8/2011 | Doyle et al. |
| 2012/0123234 A1 | 5/2012 | Atlas et al. |
| 2012/0172694 A1 | 7/2012 | Desborough et al. |
| 2012/0227737 A1 | 9/2012 | Mastrototaro et al. |
| 2012/0245556 A1 | 9/2012 | Kovatchev et al. |
| 2012/0246106 A1 | 9/2012 | Atlas et al. |
| 2013/0102867 A1 | 4/2013 | Desborough et al. |

(56) References Cited

U.S. PATENT DOCUMENTS

| | | |
|---|---|---|
| 2013/0231642 A1 | 9/2013 | Doyle et al. |
| 2013/0245547 A1 | 9/2013 | El-Khatib et al. |
| 2013/0338629 A1 | 12/2013 | Agrawal et al. |
| 2013/0338630 A1 | 12/2013 | Agrawal et al. |
| 2013/0345663 A1 | 12/2013 | Agrawal et al. |
| 2014/0005633 A1 | 1/2014 | Finan |
| 2014/0066884 A1 | 3/2014 | Keenan et al. |
| 2014/0066887 A1 | 3/2014 | Mastrototaro et al. |
| 2014/0066888 A1 | 3/2014 | Parikh et al. |
| 2014/0066889 A1 | 3/2014 | Grosman et al. |
| 2014/0180240 A1 | 6/2014 | Finan et al. |
| 2014/0276553 A1 | 9/2014 | Rosinko et al. |
| 2014/0276554 A1 | 9/2014 | Finan et al. |
| 2014/0276555 A1 | 9/2014 | Morales |
| 2014/0309615 A1 | 10/2014 | Mazlish |
| 2014/0350369 A1 | 11/2014 | Budiman et al. |
| 2015/0045767 A1 | 2/2015 | Kamen et al. |
| 2015/0073337 A1 | 3/2015 | Saint et al. |
| 2015/0164343 A1 | 6/2015 | Huang et al. |
| 2015/0238694 A1 | 8/2015 | Steil et al. |
| 2015/0289823 A1 | 10/2015 | Rack-Gomer et al. |
| 2015/0314062 A1 | 11/2015 | Blomquist et al. |
| 2015/0328402 A1 | 11/2015 | Nogueira et al. |
| 2016/0030669 A1 | 2/2016 | Harris et al. |
| 2016/0038673 A1 | 2/2016 | Morales |
| 2016/0082187 A1 | 3/2016 | Schaible et al. |
| 2016/0082188 A1 | 3/2016 | Blomquist et al. |
| 2016/0158438 A1 | 6/2016 | Monirabbasi et al. |
| 2016/0162662 A1 | 6/2016 | Monirabbasi et al. |
| 2016/0213841 A1 | 7/2016 | Geismar et al. |
| 2016/0256629 A1 | 9/2016 | Grosman et al. |
| 2016/0317743 A1 | 11/2016 | Estes |
| 2017/0049386 A1 | 2/2017 | Abraham et al. |
| 2017/0182248 A1 | 6/2017 | Rosinko |
| 2017/0332952 A1 | 11/2017 | Desborough et al. |

FOREIGN PATENT DOCUMENTS

| | | |
|---|---|---|
| WO | 2006/124716 A3 | 3/2007 |
| WO | 2008/057384 A3 | 9/2008 |
| WO | 2008/157780 A1 | 12/2008 |
| WO | 2010/089307 A1 | 8/2010 |
| WO | 2011/030343 A1 | 3/2011 |
| WO | 2015/187738 A1 | 12/2015 |
| WO | 2017/027459 A1 | 2/2017 |

OTHER PUBLICATIONS

Dassau and Associates, 12-Week 24/7 Ambulatory Artificial Pancreas With Weekly Adaptation of Insulin Delivery Settings: Effect on Hemoglobin A1C and Hypoglycemia, Diabetes Care, Oct. 13, 2017.

Guy A. Dumont, Feedback Control for Clinicians, Springer Science+ Media, Apr. 12, 2013, New York.

Fischer et al., In Vivo Comparison of Different Algorithms for the Artificial Beta-Cell, Artificial Organs, 9(2), International Society for Artificial Organs, May 1985, New York.

E. Salzsieder, G. Albrecht, E. Jutzi, and U. Fischer, Estimation of Individually Adapted Control Parameters or an Artificial Beta Cell, Biomedica Biochimica Acta. 43(5) pp. 585-596, May 1984.

Michele Schiavon, Chiara Dalla Man, Yogish C. Kudva, Ananda Basu, and Claudio Cobelli, Quantitative Estimation of Insulin Sensitivity in Type 1 Diabetic Subjects Wearing a Sensor-Augmented Insulin Pump, Diabetes Care, vol. 37, pp. 1216-1223, May 2014.

Samuel Vozeh and Jean-Louis Steimer, Feedback Control Methods for Drug Dosage Optimisation, Concepts, Classification and Clinical Application, Clinical Pharmacokinetics, 10(6), pp. 457-476, Nov.-Dec. 1985.

Written Opinion of the International Searching Authority for PCT Application No. PCT/US2018/013639 dated Apr. 20, 2018, 6 pages.

International Search Report for PCT Application No. PCT/US2018/013639 dated Apr. 20, 2018, 3 pages.

*FIG. 9A*

- 900a
- Enter carbs for food
- 5
- 10
- 15
- 20 grams = 2 units
- 25
- 30
- 35
- Adjust total
- Total insulin = 3.5 units — 910
- (recommended insulin including meal)
- Continue

*FIG. 9B*

- 900b
- Enter carbs for food
- 20 grams = 2 units — 920
- Total insulin
- 3.3
- 3.4
- 3.5
- + 3.6 units
- 3.7
- 3.8
- 3.9
- Recommended total insulin including meal = 3.5 units — 912
- Continue

SYSTEM AND METHOD FOR ADJUSTING INSULIN DELIVERY

CROSS-REFERENCE TO RELATED APPLICATION

This application claims the benefit under 35 U.S.C. § 119(e) of U.S. Provisional Patent Application Ser. No. 62/446,244, filed Jan. 13, 2017, the disclosure of which is hereby incorporated herein in its entirety by this reference.

TECHNICAL FIELD

This document relates to systems and methods for adjusting insulin delivery.

BACKGROUND

Diabetes mellitus is a chronic metabolic disorder caused by an inability of a person's pancreas to produce sufficient amounts of the hormone, insulin, such that the person's metabolism is unable to provide for the proper absorption of sugar and starch. This failure leads to hyperglycemia, i.e., the presence of an excessive amount of glucose within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Because healing is not yet possible, a permanent therapy is necessary that provides constant glycemic control in order to constantly maintain the level of blood glucose within normal limits. Such glycemic control is achieved by regularly supplying external drugs to the body of the patient to thereby reduce the elevated levels of blood glucose.

Historically, diabetes is treated with multiple, daily injections of rapid and long acting insulin via a hypodermic syringe. One or two injections per day of a long acting insulin is administered to provide a basal level of insulin and additional injections of a rapidly acting insulin is administered before or with each meal in an amount proportional to the size of the meal. Insulin therapy can also be administered using an insulin pump that provides periodic or continuous release of the rapidly acting insulin to provide for a basal level of insulin and larger doses of that same insulin at the time of meals. Insulin pumps allow for the delivery of insulin in a manner that bears greater similarity to the naturally occurring physiological processes and can be controlled to follow standard or individually modified protocols to give the patient better glycemic control. In some circumstances, an insulin pump device can store (via input from a clinician or a user) a number of settings (e.g., dosage parameters or other settings) that are customized by the physician for the particular user.

People with diabetes, their caregivers, and their health care providers (HCPs) bear a great deal of cognitive burden in managing intensive medicine therapy. Delivering the correct amount of the medicine at the correct time is an extremely challenging endeavor. Such delivery requires the patient to make dosing determinations multiple times per day and also requires a combination of the patient and the HCP to recalibrate the therapeutic parameters of the therapy on an episodic time frame that varies from individual to individual, and within individuals based on age and/or behavior (e.g., change in exercise, change in diet).

In light of the many deficiencies and problems associated with current systems and methods for maintaining proper glycemic control, enormous resources have been put into finding better solutions. A number of new technologies promise to mitigate some of the cognitive burden that intensive insulin therapy now requires. Developing workable solutions to the problem that are simple, safe, reliable and able to gain regulatory approval has, however, proved to be elusive. For years, researchers have contemplated coupling a continuous glucose monitoring system with an insulin delivery device to provide an "artificial pancreas" to assist people living with diabetes. Their efforts have yet to result in a commercial product. What has been needed is a system and method that provides a level of automatic control of drug delivery devices for improved medicine delivery and glycemic control that is simple, safe, and reliable in a real world setting.

BRIEF SUMMARY

One or more embodiments of the present disclosure may include a method. The method may include determining available insulin delivery segments for a back-fill time based on a correction bolus; determining a cumulative insulin on board (IOB) based on all the available insulin delivery segments being back-filled; back-filling a number of the available insulin delivery segments; adjusting the number of the available insulin delivery segments that are back-filled until one of the cumulative IOB based on the number of back-filled insulin delivery segments is equal to or less than the correction bolus, or the cumulative insulin of the number of back-filled insulin delivery segments is less than the correction bolus; and adjusting a baseline basal rate based on the back-filled insulin delivery segments, the baseline basal rate used for a diurnal time block related to at least a portion of the back-fill time.

One or more other embodiments of the present disclosure include a system. The system may include an insulin delivery device and a control device. The insulin delivery device may be configured to deliver insulin via a plurality of insulin delivery actions over a back-fill time prior to a correction bolus, and deliver the correction bolus. The control device may be in communication with the insulin delivery device. The control device may be configured to: obtain an amount of insulin delivered in the correction bolus; determine available insulin delivery segments for the back-fill time based on which of the plurality of insulin delivery actions delivered less than a maximum amount of insulin relative to a baseline basal rate; back-fill a number of the available insulin delivery segments based on an amount of insulin in the correction bolus; and adjust a baseline basal rate based on the back-filled insulin delivery segments, the baseline basal rate used for a diurnal time block related to at least a portion of the back-fill time.

BRIEF DESCRIPTION OF THE DRAWINGS

Example embodiments will be described and explained with additional specificity and detail through the use of the accompanying drawings in which:

FIGS. 9A and 9B illustrate example user interfaces for entering a bolus dose;

DETAILED DESCRIPTION

Figure 1:
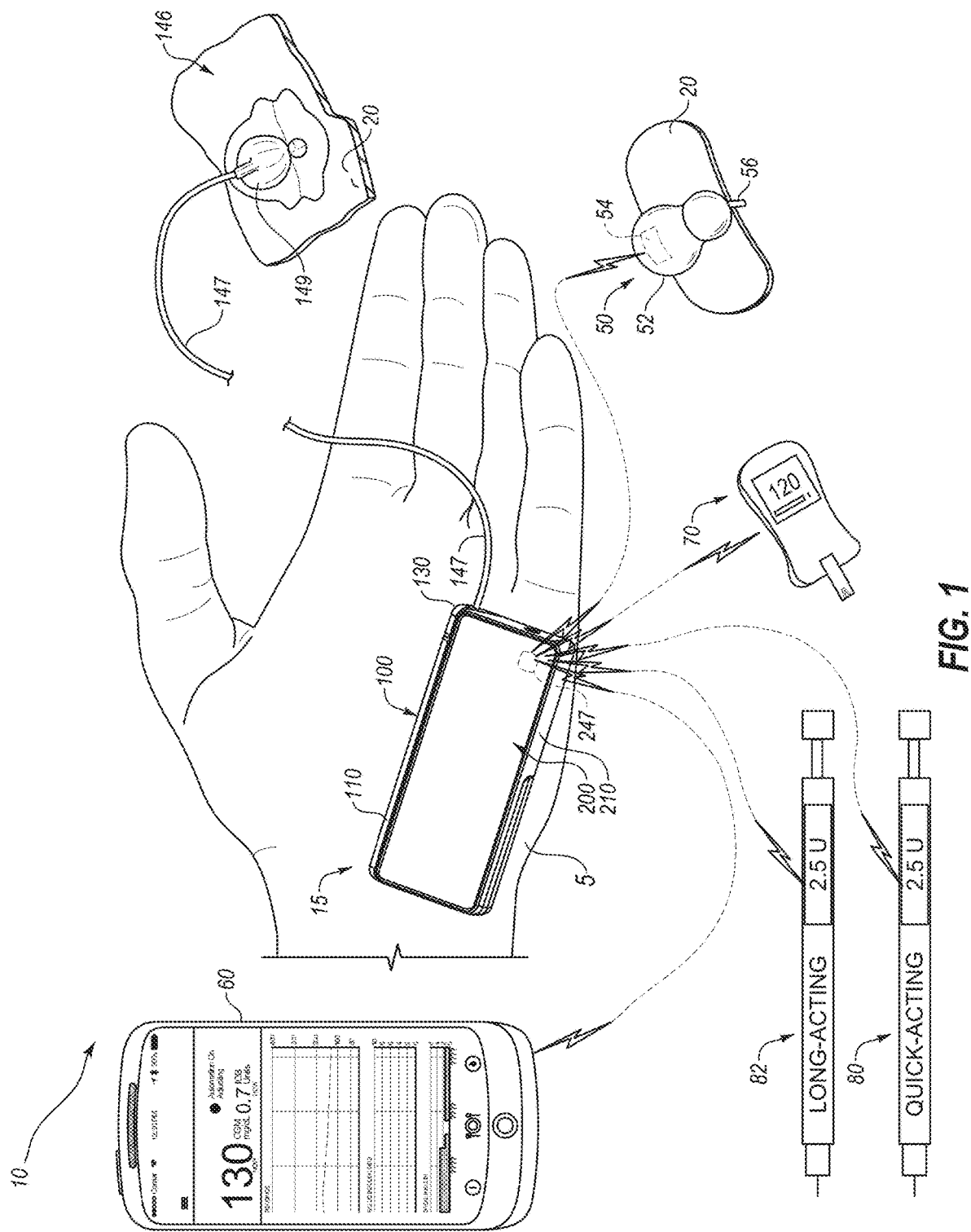
FIG. 1 illustrates an example diabetes management system.

Methods and systems provided herein may simplify the selection and personalizing of therapeutic parameters, such as basal rate (BR), carbohydrate-to-insulin ratio (CR), and insulin sensitivity factor (ISF), used when making insulin dosage decisions for a person with diabetes (PWD). Various examples of personalizing therapeutic parameters are described herein. Methods and systems provided herein can use a personalized BR to determine an appropriate basal rate if using an insulin pump, an appropriate injection of long acting insulin (e.g., if treating diabetes with multiple daily injections), an appropriate CR, or an appropriate ISF. In some cases, methods and systems provided herein can use a personalized CR to determine an appropriate insulin bolus (using a pump, pen, or syringe to deliver quick acting insulin) to address an amount of carbohydrates consumed for a meal. In some cases, methods and systems provided herein can use a personalized ISF to determine an appropriate correction bolus (using a pump, pen, or syringe to deliver quick acting insulin) to address an elevated blood glucose level.

In some cases, methods and systems of the present disclosure may include receiving one or more manually input therapeutic parameters for a PWD and comparing the manually input therapeutic parameters to a typical probability distribution. For example, the combination of therapeutic parameters may be compared to a probability distribution of a general combination of therapeutic parameters or a distribution of therapeutic parameters of a large diabetic population. After such a comparison has been performed, the result of such a comparison may be presented to a user (such as the PWD or a caregiver of the PWD). Additionally or alternatively, a recommended modification to the therapeutic parameters may be provided to the user.

In some cases, methods and systems of the present disclosure may include disabling personalization or certain aspects of personalization if a PWD receives a bolus dose or if the PWD receives a bolus dose different than a recommended bolus dose of insulin. For example, a user may request a bolus dose of insulin based on an upcoming meal or a high blood glucose level. A control device may provide a recommended bolus dose based on one or more therapeutic parameters of the PWD. If the user overrides the recommended bolus dose to deliver more or less insulin than recommended, the control device may disable any personalization for a certain amount of time after the user override such that the personalization is not based on a bolus dose that is too large or too small. Such a lockout feature may prevent the control device from delivering a varying ratio of the baseline basal rate (e.g., prevent the control device from delivering 0×, 1×, or 2× the baseline basal rate), and/or may prevent the control device from considering the blood glucose levels while affected by the overridden bolus dose in personalizing the baseline basal rate for diurnal time periods.

Example Diabetes Management System

FIG. 1 depicts an example diabetes management system 10, in accordance with one or more embodiments of the present disclosure. The diabetes management system 10 may include a pump assembly 15 for insulin and a continuous glucose monitor 50. As shown, the continuous glucose monitor 50 is in wireless communication with pump assembly 15. In some cases, a continuous glucose monitor can be in wired communication with pump assembly 15. In some cases, not shown, a continuous glucose monitor can be incorporated into an insulin pump assembly. As shown, pump assembly 15 can include a reusable pump controller 200 that forms part of the pump assembly 15. In some cases, reusable pump controller 200 is adapted to determine one or more basal delivery rates. In some cases, continuous glucose monitor 50 can act as a controller adapted to communicate basal delivery rates to pump assembly 15.

Pump assembly 15, as shown, can include reusable pump controller 200 and a disposable pump 100, which can contain a reservoir for retaining insulin. A drive system for pushing insulin out of the reservoir can be included in either the disposable pump 100 or the reusable pump controller 200 in a controller housing 210. Reusable pump controller 200 can include a wireless communication device 247, which can be adapted to communicate with a wireless communication device 54 of continuous glucose monitor 50 and other diabetes devices in the system, such as those discussed below. In some cases, pump assembly 15 can be sized to fit within a palm of a hand 5. Pump assembly 15 can include an infusion set 146. Infusion set 146 can include a flexible tube 147 that extends from the disposable pump 100 to a subcutaneous cannula 149 that may be retained by a skin adhesive patch (not shown) that secures the subcutaneous cannula 149 to the infusion site. The skin adhesive patch can retain the cannula 149 in fluid communication with the tissue or vasculature of the PWD so that the medicine dispensed through tube 147 passes through the cannula 149 and into the PWD's body. The cap device 130 can provide fluid communication between an output end of an insulin cartridge (not shown) and tube 147 of infusion set 146. Although pump assembly 15 is depicted as a two-part insulin pump, one piece insulin pumps are also contemplated. Additionally, insulin pump assemblies used in methods and systems provided herein can alternatively be a patch pump.

Continuous glucose monitor 50 (e.g., a glucose sensor) can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of the PWD's blood glucose level or the like. In some cases, the sensor shaft 56 can measure glucose or another analyte in interstitial fluid or in another fluid and correlate that to blood glucose levels. In response to the measurements made by the sensor shaft 56, the continuous glucose monitor 50 can employ the wireless communication device 54 to transmit data to a corresponding wireless communication device 247 housed in the pump assembly 15. In some cases, the continuous glucose monitor 50 may include a circuit that permits sensor signals (e.g., data from the sensor shaft 56) to be communicated to the wireless communication device 54. The wireless communication device 54 can transfer the collected data to reusable pump controller 200 (e.g., by wireless communication to the wireless communication device 247). Additionally or alternatively, the system 10 may include another glucose monitoring device that may utilize any of a variety of methods of obtaining information indicative of a PWD's blood glucose levels and transferring that information to reusable pump controller 200. For example, an alternative monitoring device may employ a micropore system in which a laser porator creates tiny holes in the uppermost layer of a PWD's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. In other examples, the monitoring device can include detect glucose levels using equilibrium fluorescence detectors (e.g., sensors including a diboronic acid receptor attached to a fluorophore). Furthermore, it should be understood that in some alternative implementations, continuous glucose monitor 50 can be in communication with reusable pump controller 200 or another computing device via a wired connection. In some cases, continuous glucose monitor 50 can be adapted to provide blood glucose measurements for a PWD when in use for the PWD at regular or irregular time intervals. In some cases, continuous glucose monitor 50 can detect blood glucose measurements at least every thirty minutes, at least every fifteen minutes, at least every ten minutes, at least every five minutes, or about every minute. In some cases, continuous glucose monitor 50 can itself determine a basal delivery rate using methods provided herein and communicate that basal rate to the pump assembly 15. In some cases, continuous glucose monitor 50 can transmit blood glucose measurement data to reusable pump controller 200 and reusable pump controller 200 can use methods provided herein to determine a basal delivery rate. In some cases, a remote controller can receive glucose data from continuous glucose monitor 50, determine a basal delivery rate using methods provided herein, and communicate the basal rate to pump assembly 15.

Diabetes management system 10 may optionally include a blood glucose meter 70 (e.g., a glucose sensor). In some cases, blood glucose meter 70 can be in wireless communication with reusable pump controller 200. Blood glucose meter 70 can take a blood glucose measurement using one or more test strips (e.g., blood test strips). A test strip can be inserted into a strip reader portion of the blood glucose meter 70 and then receive the PWD's blood to determine a blood glucose level for the PWD. In some cases, the blood glucose meter 70 is configured to analyze the characteristics of the PWD's blood and communicate (e.g., via a BLUETOOTH® wireless communication connection) the information to reusable pump controller 200. In some cases, a user can manually input a glucose meter reading. The blood glucose meter 70 can be manually operated by a user and may include an output subsystem (e.g., display, speaker) that can provide the user with blood glucose readings that can be subsequently entered into the controller or user interface to collect the data from an unconnected BGM into the system. The blood glucose meter 70 may be configured to communicate data (e.g., blood glucose readings) obtained to reusable pump controller 200 and/or other devices, such as the mobile computing device 60 (e.g., a control device). Such communication can be over a wired and/or wireless connection, and the data can be used by system 10 for a number of functions (e.g., calibrating the continuous glucose monitor 50, confirming a reading from the continuous glucose monitor 50, determining a more accurate blood glucose reading for a bolus calculation, detecting a blood glucose level when the continuous glucose monitor 50 is malfunctioning).

In some cases, the system 10 can further include a mobile computing device 60 that can communicate with the reusable pump controller 200 through a wireless and/or wired connection with the reusable pump controller 200 (e.g., via a BLUETOOTH® wireless communication connection or a near-field communication connection). In some cases, the mobile computing device 60 communicates wirelessly with other diabetes devices of system 10. The mobile computing device 60 can be any of a variety of appropriate computing devices, such as a smartphone, a tablet computing device, a wearable computing device, a smartwatch, a fitness tracker, a laptop computer, a desktop computer, and/or other appropriate computing devices. In some cases (for example, where the reusable pump controller 200 does not determine a basal delivery rate), the mobile computing device 60 can receive and log data from other elements of the system 10 and determine basal delivery rates using methods provided herein. In some cases, a user can input relevant data into the mobile computing device 60. In some cases, the mobile computing device 60 can be used to transfer data from the reusable pump controller 200 to another computing device (e.g., a back-end server or cloud-based device). In some cases, one or more methods provided herein can be performed or partially performed by the other computing device. In some cases, the mobile computing device 60 provides a user interface (e.g., graphical user interface (GUI), speech-based user interface, motion-controlled user interface) through which users can provide information to control operation of the reusable pump controller 200 and the system 10. For example, the mobile computing device 60 can be a mobile computing device running a mobile app that communicates with reusable pump controller 200 over short-range wireless connections (e.g., BLUETOOTH® connection, Wi-Fi Direct connection, near-field communication connection, etc.) to provide status information for the system 10 and allow a user to control operation of the system 10 (e.g., toggle between delivery modes, adjust settings, log food intake, change a fear of hypoglycemia index (FHI), confirm/modify/cancel bolus dosages, and the like).

Optionally, system 10 may include a bolus administering device 80 (e.g., a syringe, an insulin pen, a smart syringe with device communication capabilities, or the like) through which bolus dosages can be manually administered to a PWD. In some cases, a suggested dosage for a bolus to be administered using the bolus administering device 80 can be output to a user via the user interface of reusable pump controller 200 and/or the user interface of the mobile computing device 60. In some cases, the bolus administering device 80 can communicate through a wired and/or wireless connection with reusable pump controller 200 and/or the mobile computing device 60. In some cases, system 10 can allow users to input insulin deliveries made using a syringe or insulin pen.

In some cases, methods and systems of treating diabetes can include the use of an insulin pump assembly 15, which can be used to deliver both a continuous (or semi-continuous) supply of quick acting insulin at a personalized BR and to delivery boluses of the quick acting insulin to make corrections for elevated blood glucose levels or to address consumed carbohydrates. In some cases, methods and systems of treating diabetes can include the use of a continuous blood glucose monitor 50 (CGM) that can communicate blood glucose data to a controller such as the mobile computing device 60 and/or the pump controller 200 that can automate insulin delivery dynamically to address current or anticipated high or low blood glucose levels. In some cases, methods and systems provided herein can make adjustments to therapeutic parameters based upon the automated insulin deliveries determined using continuous (or semi-continuous) blood glucose data.

In some cases, methods and systems of treating diabetes can include the use of multiple daily injections (MDIs) of different types of insulin. For example, MDIs can include the injection of long acting insulin at least once a day to cover a baseline insulin requirement and the injection of a quick acting insulin to make corrections or to address consumed carbohydrates.

In some embodiments, the system 10 may include a bolus administering device 80 (e.g., a syringe, an insulin pen, a smart syringe with device communication capabilities using quick acting insulin, or the like) through which bolus dosages can be manually administered to a PWD. As illustrated in FIG. 1, such a bolus administering device may be referred to as an injection based delivery device. In some cases, a suggested dosage for a bolus to be administered using the bolus administering device 80 can be output to a user via the user interface of reusable pump controller 200 and/or the user interface of the mobile computing device 60. In some cases, the bolus administering device 80 can communicate through a wired and/or wireless connection with reusable pump controller 200 and/or the mobile computing device 60. In some cases, system 10 can allow users to input insulin deliveries made using a syringe or insulin pen.

In some embodiments, the system 10 may include a basal administering device 82 (e.g., a syringe, an insulin pen, a smart syringe with device communication capabilities using long acting insulin, or the like) through which basal insulin can be manually administered to a PWD, such as a once per day dose or a twice per day dose. As illustrated in FIG. 1, such a basal administering device may be referred to as an injection based delivery device. In some cases, the amount of basal insulin for a given dose may be determined by the mobile computing device 60. For example, the mobile computing device 60 may display an amount of insulin to be delivered as a daily basal dose. Additionally or alternatively, if the basal administering device 82 includes communication capabilities, the mobile computing device 60 may transmit a message to the basal administering device 82 indicating the amount of basal insulin to be delivered in the dose.

Additional Details About Example Pump Assembly

Figure 2A:
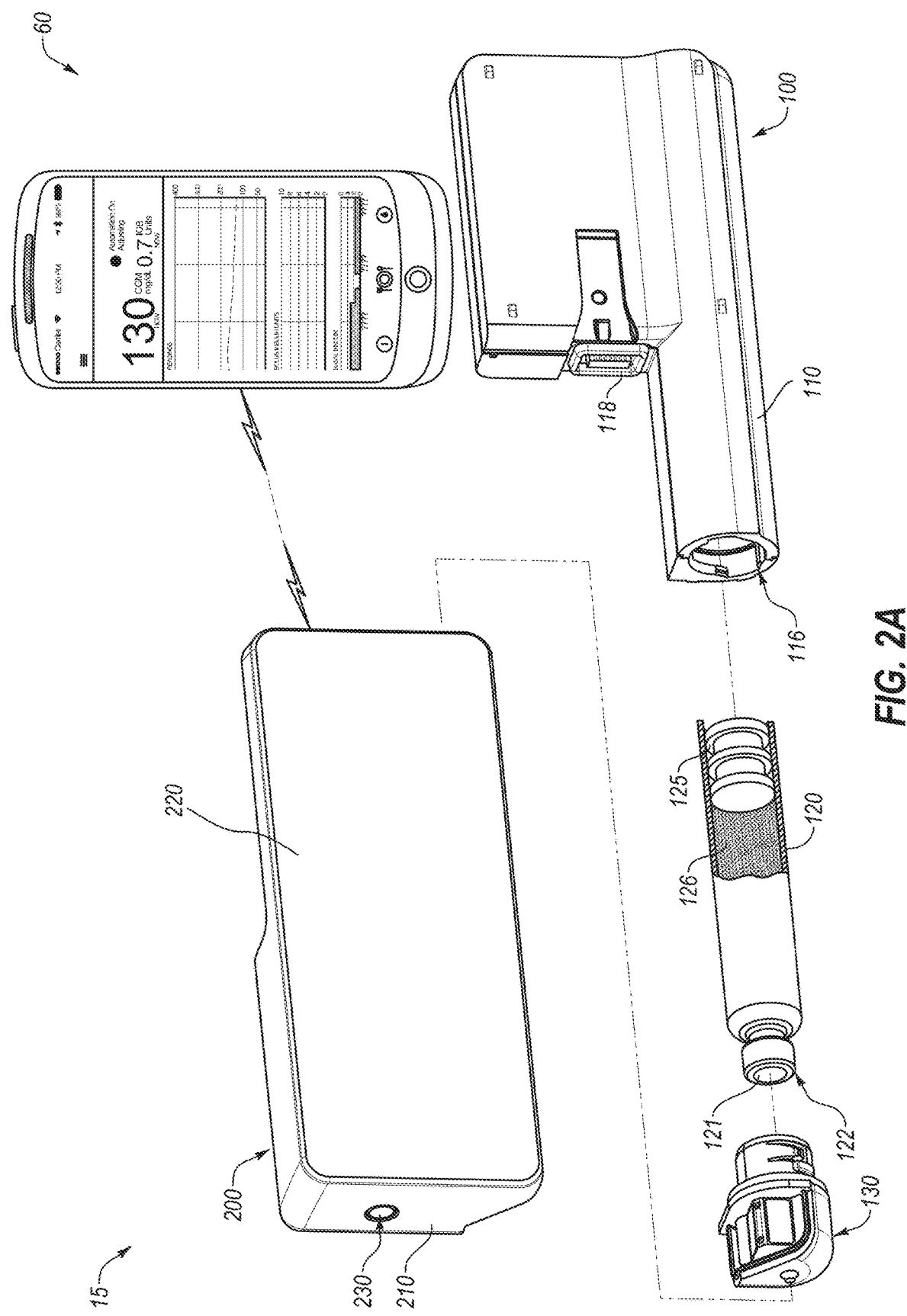
FIGS. 2A and 2B illustrate additional details of the example system of FIG. 1.
Figure 2B:
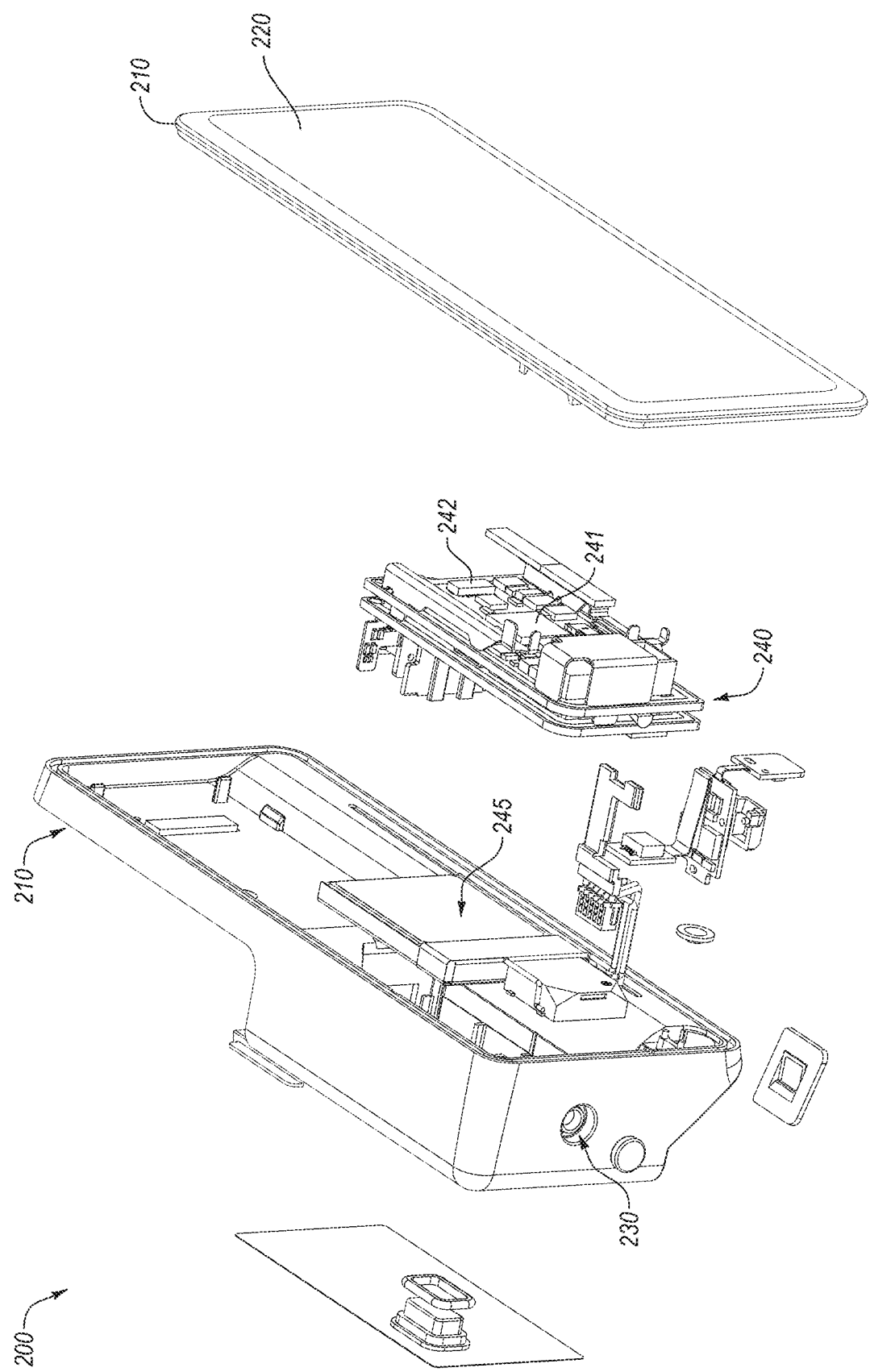

FIGS. 2A and 2B illustrate additional details of the example system 10 of FIG. 1.

FIGS. 2A and 2B provide additional details about example pump assembly 15 as discussed above in regards to FIG. 1. FIG. 2B depicts the details of example reusable pump controller 200.

Referring now to FIG. 2A, disposable pump 100 in this embodiment includes a pump housing structure 110 that defines a cavity 116 in which a fluid cartridge 120 can be received. Disposable pump 100 also can include a cap device 130 to retain the fluid cartridge 120 in the cavity 116 of the pump housing structure 110. Disposable pump 100 can include a drive system (e.g., including a battery powered actuator, a gear system, a drive rod, and other items that are not shown in FIG. 2A) that advances a plunger 125 in the fluid cartridge 120 so as to dispense fluid therefrom. In this embodiment, reusable pump controller 200 communicates with disposable pump 100 to control the operation of the drive system. For example, in some cases, the reusable pump controller 200 can generate a message for the disposable pump 100 directing the disposable pump 100 to deliver a certain amount of insulin or deliver insulin at a certain rate. In some cases, such a message may direct the disposable pump 100 to advance the plunger 125 a certain distance. In some cases, not depicted, reusable pump controller 200 may include a user interface to control the operation of disposable pump 100. In some cases, disposable pump 100 can be disposed of after a single use. For example, disposable pump 100 can be a "one-time-use" component that is thrown away after the fluid cartridge 120 therein is exhausted. Thereafter, the user can removably attach a new disposable pump 100 (having a new fluid cartridge) to the reusable pump controller 200 for the dispensation of fluid from a new fluid cartridge. Accordingly, the user is permitted to reuse reusable pump controller 200 (which may include complex or valuable electronics, as well as a rechargeable battery) while disposing of the relatively low-cost disposable pump 100 after each use. Such a pump assembly 15 can provide enhanced user safety as a new pump device (and drive system therein) is employed with each new fluid cartridge.

The pump assembly 15 can be a medical infusion pump assembly that is configured to controllably dispense a medicine from the fluid cartridge 120. As such, the fluid cartridge 120 can contain a medicine 126 to be infused into the tissue or vasculature of a targeted individual, such as a human or animal patient. For example, disposable pump 100 can be adapted to receive a fluid cartridge 120 in the form of a carpule that is preloaded with insulin or another medicine for use in the treatment of diabetes (e.g., Exenatide (BYETTA®, BYDUREON®) and liraglutide (VICTOZA®)

SYMLIN®, or others). Such a fluid cartridge 120 may be supplied, for example, by Eli Lilly and Co. of Indianapolis, Ind. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, disposable pump 100 can include one or more structures that interfere with the removal of the fluid cartridge 120 after the fluid cartridge 120 is inserted into the cavity 116. For example, the pump housing structure 110 can include one or more retainer wings (not shown) that at least partially extend into the cavity 116 to engage a portion of the fluid cartridge 120 when the fluid cartridge 120 is installed therein. Such a configuration may facilitate the "one-time-use" feature of disposable pump 100. In some embodiments, the retainer wings can interfere with attempts to remove the fluid cartridge 120 from disposable pump 100, thus ensuring that disposable pump 100 will be discarded along with the fluid cartridge 120 after the fluid cartridge 120 is emptied, expired, or otherwise exhausted. In another example, the cap device 130 can be configured to irreversibly attach to the pump housing structure 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, disposable pump 100 can operate in a tamper-resistant and safe manner because disposable pump 100 can be designed with a predetermined life expectancy (e.g., the "one-time-use" feature in which the pump device is discarded after the fluid cartridge 120 is emptied, expired, or otherwise exhausted).

Still referring to FIG. 2A, reusable pump controller 200 can be removably attached to disposable pump 100 so that the two components are mechanically mounted to one another in a fixed relationship. In some embodiments, such a mechanical mounting can also form an electrical connection between the reusable pump controller 200 and disposable pump 100 (for example, at electrical connector 118 of disposable pump 100). For example, reusable pump controller 200 can be in electrical communication with a portion of the drive system (not shown) of disposable pump 100. In some embodiments, disposable pump 100 can include a drive system that causes controlled dispensation of the medicine or other fluid from the fluid cartridge 120. In some embodiments, the drive system incrementally advances a piston rod (not shown) longitudinally into the fluid cartridge 120 so that the fluid is forced out of an output end 122. A septum 121 at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device 130 to the pump housing structure 110. Thus, when disposable pump 100 and reusable pump controller 200 are mechanically attached and thereby electrically connected, reusable pump controller 200 communicates electronic control signals via a hardwire-connection (e.g., electrical contacts along electrical connector 118 or the like) to the drive system or other components of disposable pump 100. In response to the electrical control signals from reusable pump controller 200, the drive system of disposable pump 100 causes medicine to incrementally dispense from the fluid cartridge 120. Power signals, such as signals from a battery (not shown) of reusable pump controller 200 and from the power source (not shown) of disposable pump 100, may also be passed between reusable pump controller 200 and disposable pump 100.

Referring again to FIGS. 1 and 2A, the pump assembly 15 can be configured to be portable and can be wearable and concealable. For example, a PWD can conveniently wear the pump assembly 15 on the PWD's skin (e.g., skin adhesive) underneath the PWD's clothing or carry disposable pump 100 in the PWD's pocket (or other portable location) while receiving the medicine dispensed from disposable pump 100. The pump assembly 15 is depicted in FIG. 1 as being held in a PWD's hand 5 so as to illustrate the size of the pump assembly 15 in accordance with some embodiments. This embodiment of the pump assembly 15 is compact so that the PWD can wear the pump assembly 15 (e.g., in the PWD's pocket, connected to a belt clip, adhered to the PWD's skin, or the like) without the need for carrying and operating a separate module. In such embodiments, the cap device 130 of disposable pump 100 can be configured to mate with an infusion set 146. In general, the infusion set 146 can be a tubing system that connects the pump assembly 15 to the tissue or vasculature of the PWD (e.g., to deliver medicine into the tissue or vasculature under the PWD's skin). The infusion set 146 can include a tube 147 that is flexible and that extends from disposable pump 100 to a subcutaneous cannula 149 that may be retained by a skin adhesive patch (not shown) that secures the subcutaneous cannula 149 to the infusion site. The skin adhesive patch can retain the cannula 149 in fluid communication with the tissue or vasculature of the PWD so that the medicine dispensed through the tube 147 passes through the cannula 149 and into the PWD's body. The cap device 130 can provide fluid communication between the output end 122 (FIG. 2A) of the fluid cartridge 120 and the tube 147 of the infusion set 146.

In some embodiments, the pump assembly 15 can be pocket-sized so that disposable pump 100 and reusable pump controller 200 can be worn in the PWD's pocket or in another portion of the PWD's clothing. In some circumstances, the PWD may desire to wear the pump assembly 15 in a more discrete manner. Accordingly, the PWD can pass the tube 147 from the pocket, under the PWD's clothing, and to the infusion site where the adhesive patch can be positioned. As such, the pump assembly 15 can be used to deliver medicine to the tissues or vasculature of the PWD in a portable, concealable, and discrete manner.

In some embodiments, the pump assembly 15 can be configured to adhere to the PWD's skin directly at the location in which the skin is penetrated for medicine infusion. For example, a rear surface of disposable pump 100 can include a skin adhesive patch so that disposable pump 100 can be physically adhered to the skin of the PWD at a particular location. In these embodiments, the cap device 130 can have a configuration in which medicine passes directly from the cap device 130 into an infusion set 146 that is penetrated into the PWD's skin. In some examples, the PWD can temporarily detach reusable pump controller 200 (while disposable pump 100 remains adhered to the skin) so as to view and interact with the user interface 220.

In some embodiments, the pump assembly 15 can operate during an automated mode to deliver basal insulin according the methods provided herein. In some cases, pump assembly 15 can operate in an open loop mode to deliver insulin at the BBR. A basal rate of insulin can be delivered in an incremental manner (e.g., dispense 0.10 U every five minutes for a rate of 1.2 U per hour) according to a selected basal insulin delivery profile. A user can use the user interface on mobile computing device 60 to select one or more bolus deliveries, for example, to offset the blood glucose effects caused by food intake, to correct for an undesirably high blood glucose level, to correct for a rapidly increasing blood glucose level, or the like. In some circumstances, the basal rate delivery pattern may remain at a substantially constant rate for a long period of time (e.g., a first basal dispensation rate for a period of hours in the morning, and a second basal dispensation rate for a period of hours in the afternoon and evening). In contrast, the bolus dosages can be more frequently dispensed based on calculations made by reusable pump controller 200 or the mobile computing device 60 (which then communicates to reusable pump controller 200). For example, reusable pump controller 200 can determine that the PWD's blood glucose level is rapidly increasing (e.g., by interpreting data received from the continuous glucose monitor 50), and can provide an alert to the user (via the user interface 220 or via the mobile computing device 60) so that the user can manually initiate the administration of a selected bolus dosage of insulin to correct for the rapid increase in blood glucose level. In one example, the user can request (via the user interface of mobile computing device 60) a calculation of a suggested bolus dosage (e.g., calculated at the mobile computing device 60 based upon information received from the user and from reusable pump controller 200, or alternatively calculated at reusable pump controller 200 and communicated back the mobile computing device 60 for display to the user) based, at least in part, on a proposed meal that the PWD plans to consume.

Referring now to FIG. 2B, reusable pump controller 200 (shown in an exploded view) houses a number of components that can be reused with a series of successive disposable pumps 100. In particular, reusable pump controller 200 can include control circuitry 240 (e.g., a control device) and a rechargeable battery pack 245, each arranged in the controller housing 210. The rechargeable battery pack 245 may provide electrical energy to components of the control circuitry 240, other components of the controller device (e.g., a display device and other user interface components, sensors, or the like), or to components of disposable pump 100. The control circuitry 240 may be configured to communicate control or power signals to the drive system of disposable pump 100, or to receive power or feedback signals from disposable pump 100.

The control circuitry 240 of reusable pump controller 200 can include one or more microprocessors 241 configured to execute computer-readable instructions stored on one or more memory devices 242 so as to achieve any of the control operations described herein. At least one memory device 242 of the control circuitry 240 may be configured to store a number of user-specific dosage parameters. One or more user-specific dosage parameters may be input by a user via the user interface 220. Further, as described below in connection with FIG. 2A, various user-specific dosage parameters can be automatically determined and/or updated by control operations implemented by the control circuitry 240 of reusable pump controller 200. For example, the control circuitry 240 can implement a secondary feedback loop to determine and/or update one or more user-specific dosage parameters in parallel with the infusion pump system 10 operating in a closed-loop delivery mode. Whether determined automatically or received via the mobile computing device 60 (or via the user interface 220 of reusable pump controller 200), the control circuitry 240 can cause the memory device 242 to store the user-specific dosage parameters for future use during operations according to multiple delivery modes, such as closed-loop and open-loop delivery modes. Additionally, the control circuitry 240 can cause reusable pump controller 200 to periodically communicate the user-specific dosage parameters to the mobile computing device 60 for future use during operations by the mobile computing device 60 or for subsequent communication to a cloud-based computer network.

Such user-specific dosage parameters may include, but are not limited to, one or more of the following: total daily basal dosage limits (e.g., in a maximum number of units/day), various other periodic basal dosage limits (e.g., maximum basal dosage/hour, maximum basal dosage/six hour period), insulin sensitivity (e.g., in units of mg/dL/insulin unit), carbohydrate ratio (e.g., in units of g/insulin unit), insulin onset time (e.g., in units of minutes and/or seconds), insulin on board duration (e.g., in units of minutes and/or seconds), and basal rate profile (e.g., an average basal rate or one or more segments of a basal rate profile expressed in units of insulin unit/hour). Also, the control circuitry 240 can cause the memory device 242 to store (and can cause reusable pump controller 200 to periodically communicate out to the mobile computing device 60) any of the following parameters derived from the historical pump usage information: dosage logs, average total daily dose, average total basal dose per day, average total bolus dose per day, a ratio of correction bolus amount per day to food bolus amount per day, amount of correction boluses per day, a ratio of a correction bolus amount per day to the average total daily dose, a ratio of the average total basal dose to the average total bolus dose, average maximum bolus per day, and a frequency of cannula and tube primes per day. To the extent these aforementioned dosage parameters or historical parameters are not stored in the memory device 242, the control circuitry 240 can be configured to calculate any of these aforementioned dosage parameters or historical parameters from other data stored in the memory device 242 or otherwise input via communication with the mobile computing device 60.

Additionally or alternatively, an indicator light 230 may be illustrated. The indicator light 230 may include one or more lights or icons that can indicate one or more pieces of information relative to the operation of the reusable pump controller 200. For example, the indicator light 230 may indicate whether the reusable pump controller 200 is operating in a mode in which it is adjusting or modifying insulin delivery, or is delivering insulin according to a preprogrammed schedule. Additionally or alternatively, the indicator lights 230 may indicate that a user has a message, or that the disposable pump 100 is out of insulin, or the like.

Modifications, additions, or omissions may be made to the system 10 without departing from the scope of the present disclosure. For example, the system 10 may have more or fewer elements than those illustrated or described in the present disclosure. Additionally, the system 10 may include any of the components or arrangements consistent with the present disclosure. For example, the system 10 may be implemented without the use of the pump assembly 15 and instead be implemented with the basal delivery device 82 and the bolus delivery device 80. As another example, the system 10 may be implemented with the blood glucose meter (BGM) 70 and the continuous glucose meter (CGM) 50 may be omitted.

Relationship Between BR, ISF, and CR

Methods and systems provided herein can use predetermined relationships between therapeutic parameters. For example, methods and systems provided herein can utilize a general probabilistic relationship between BR, CR, and/or ISF to determine what one or more therapeutic parameters are when starting with another therapeutic parameter.

In some cases, methods and systems provided herein can estimate an initial ISF and CR based on an initial BR. For example, it may be that a PWD or their caregivers might know a total daily basal (TDB) amount, but not know the CR or ISF of the PWD. In some cases, an initial ISF setting can be set by the following equation:

$$ISF = x*BR^{-y} \quad \text{Equation (1)}$$

where BR is the total amount of number of units of basal insulin (or total number of units of long acting insulin) per day, x is a number between 1115 and 1140, and y is a number between 1.00 and 1.06. In some cases, x can be a number between 1120 and 1135 and y can be a number between 1.03 and 1.06. In some cases, x can be a number between 1125 and 1135 and y can be a number of about 1.05. In some cases, an ISF calculation provided above can be rounded to the nearest tenth of an integer or the nearest integer.

Figure 3A:
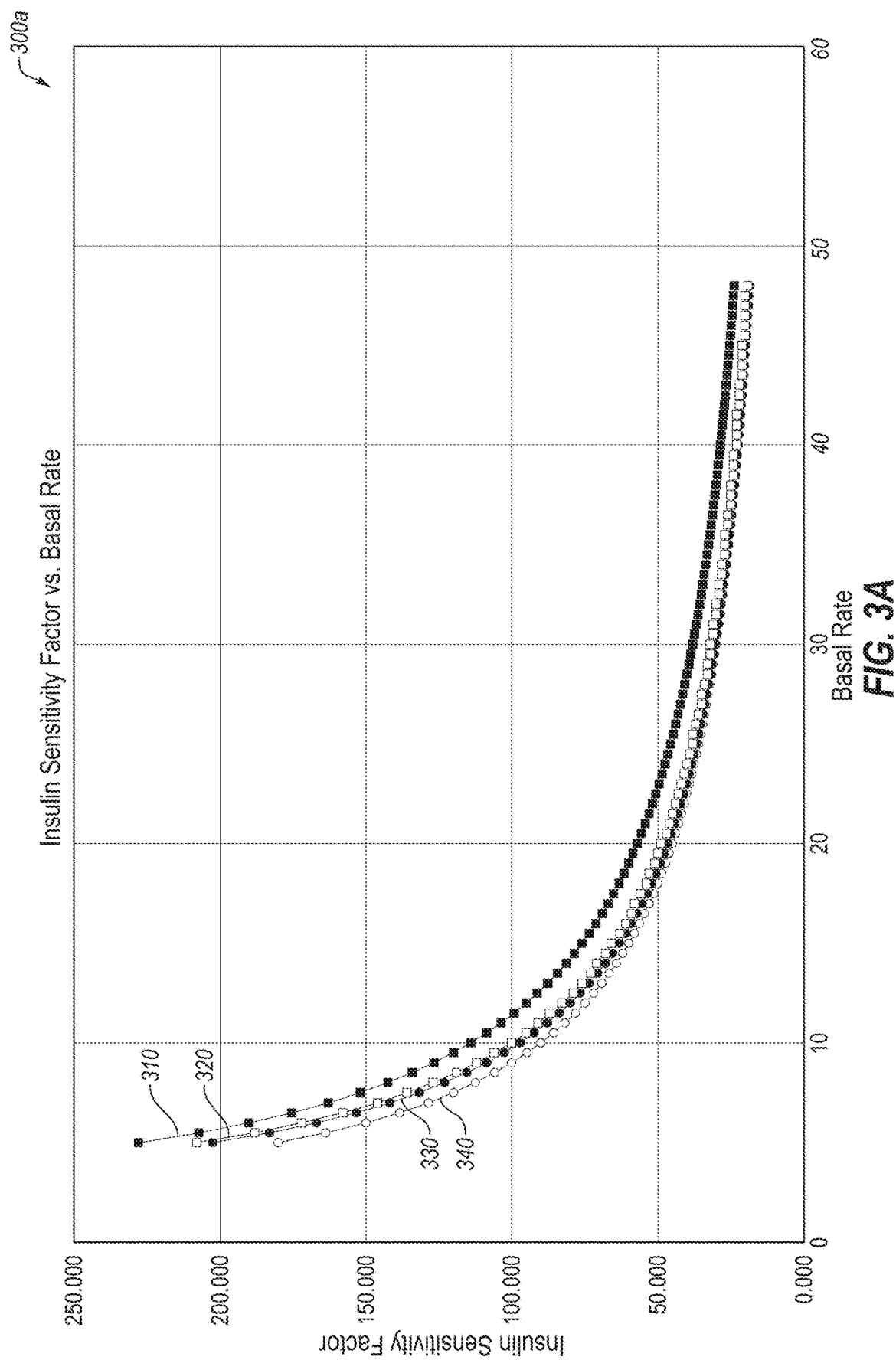
FIG. 3A illustrates an example set of curves illustrating potential insulin sensitivity factors (ISFs) based on a basal rate (BR)

FIG. 3A illustrates an example set of curves 300a illustrating potential ISFs based on a BR, in accordance with one or more embodiments of the present disclosure. Each of the curves 310, 320, and 330 may illustrate an alternative approach to determining a relationship between ISF and BR.

The first curve 310 illustrates an embodiment in which ISF is based on Equation 1 above, with x equal to 1140 and y equal to 1.00.

In some embodiments, one or more values used in determining ISF from BR may be rounded to a certain number of significant digits. For example, as illustrated in FIG. 3A, the second curve 320 illustrates an embodiment in which the ISF may be rounded to a whole number. For example, the second curve 320 is based on Equation 1, with x equal to 1127 and y equal to 1.05.

The third curve 330 illustrates an embodiment in which ISF is based on Equation 1, with x equal to 1115 and y equal to 1.06.

The fourth curve 340 illustrates the rule of 1800 as a reference for comparison to the first, second, and third curves 310, 320, and 330. The rule of 1800 is, for quick acting insulin, a PWD's ISF is determined by dividing 1800 by the total daily insulin dose, including basal insulin and bolus insulin. For example, if a PWD had basal insulin of 30 units of insulin and typically have boluses of 30 units per day, the PWD's ISF would be 1800/(30+30)=50.

In some embodiments, one or more curves comparable or similar to those illustrated in FIG. 3A may be stored in a control device (such as the mobile computing device 60 of FIG. 1) such that the one or more of the curves may function as a look-up table. For example, a user may input a BR and a corresponding ISF may be observed along the curve.

In some cases, an initial CR setting can be set by the following equation:

$$CR = a*BR^{-b} \quad \text{Equation (2)}$$

where BR is the total amount of number of units of basal insulin (or total number of units of long acting insulin) per day, a is a number between 114 and 126, and b is a number between 0.785 and 0.815. In some cases, a can be a number between 117 and 123 and b can be a number between 0.79 and 0.81. In some cases, a can be a number between 119 and 121 and b can be a number of about 0.8. In some cases, a CR calculation provided above can be rounded to the nearest tenth of an integer or the nearest integer.

Figure 3B:
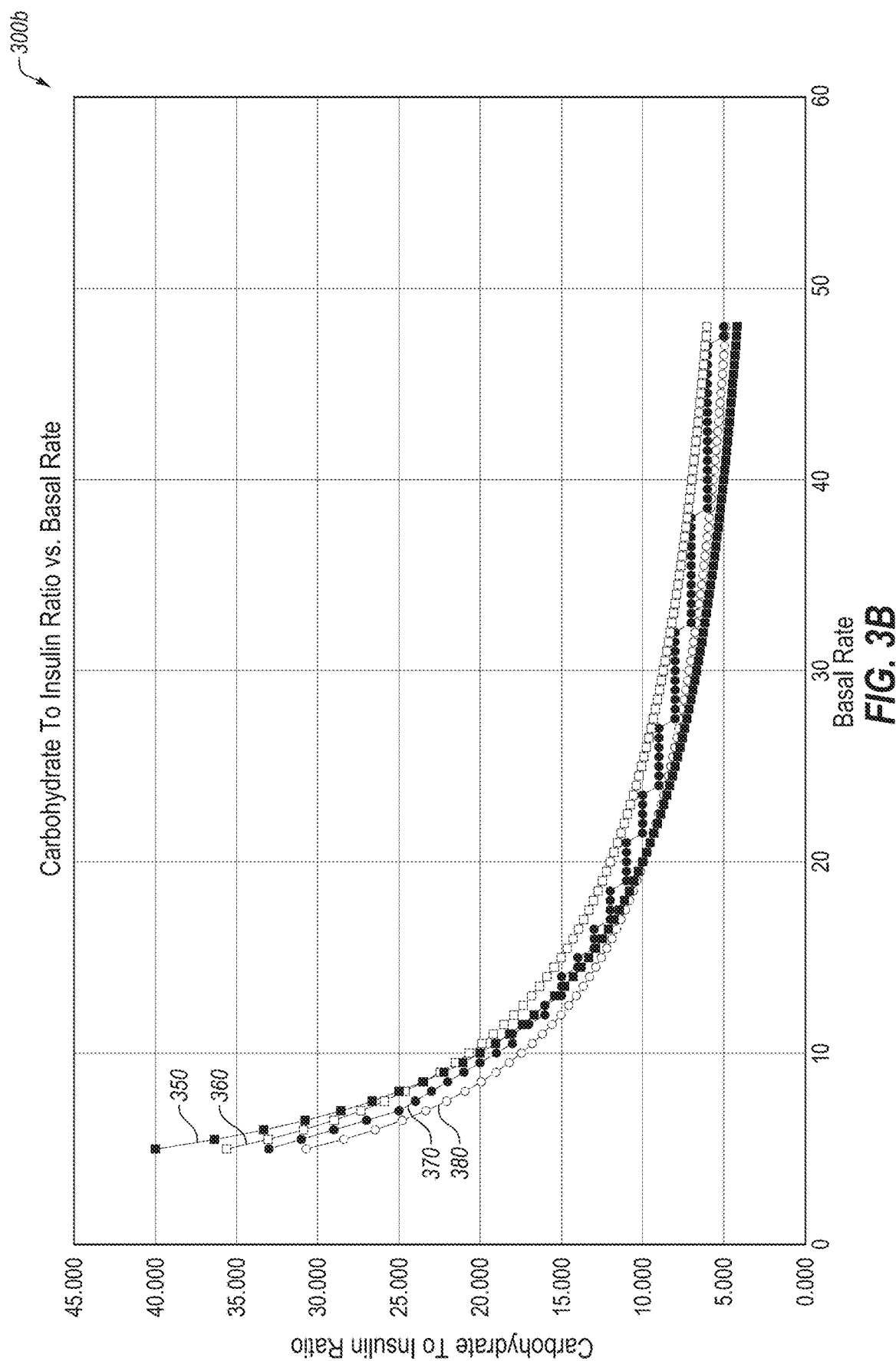
FIG. 3B illustrates an example set of curves illustrating potential carbohydrate-to-insulin ratio (CR) based on BR.

FIG. 3B illustrates an example set of curves 300b illustrating potential CRs based on a BR, in accordance with one or more embodiments of the present disclosure. Each of the curves 360, 370, and 380 may illustrate an alternative approach to determining a relationship between CR and BR.

The first curve 360 illustrates an embodiment in which CR is based on Equation 2 above, with a equal to 126 and b equal to 0.785.

In some embodiments, one or more values used in determining ISF from BR may be rounded to a certain number of significant digits. For example, as illustrated in FIG. 3B, the second curve 370 illustrates an embodiment in which the CR may be rounded to a whole number. For example, the second curve 370 is based on Equation 2, with a equal to 120 and b equal to 0.8.

The third curve 380 illustrates an embodiment in which CR is based on Equation 2, with a equal to 114 and b equal to 0.815.

The fourth curve 350 illustrates the rule of 500 as a reference for comparison to the first, second, and third curves 360, 370, and 380. The rule of 500 is, for quick acting insulin, a PWD's CR is determined by dividing 500 by the total daily insulin dose, including basal insulin and bolus insulin. For example, if a PWD had basal insulin of 30 units of insulin and typically have boluses of 30 units per day, the PWD's ISF would be 500/(30+30)=8.33.

In some embodiments, one or more curves comparable or similar to those illustrated in FIG. 3B may be stored in a control device (such as the mobile computing device 60 of FIG. 1) such that the one or more of the curves may function as a look-up table. For example, a user may input a BR and a corresponding CR may be observed along the curve.

Modifications, additions, or omissions may be made to the sets of curves 300a and 300b without departing from the scope of the present disclosure. For example, the sets of curves 300a and 300b may have more or fewer elements than those illustrated or described in the present disclosure. For example, the sets of curves 300a and 300b may include any number of curves as multiple approaches to determining therapeutic parameters.

Variation from General Probability

In some cases, a user (e.g., a PWD or caregiver) may know, or believe they know, their personalized BR, CR, and ISF (or two out of the three). Methods and systems provided herein, however, can store a probability distribution for relationships between BR, CR, and ISF for the general population. In some cases, methods and systems provided herein can alert a user to the presence of a mismatch between entered BR, CR, and ISF values (e.g., based on a distance between the entered therapeutic values and the general probability distributions exceeding a threshold) and provide a recommendation of an adjusted CR, ISF, BR, or combination thereof based on the probability distribution. For example, the recommended CR, ISF, BR, or combinations thereof may move the combination of therapeutic parameters such that the combination is closer to the general probability distribution of parameters.

Figure 4A:
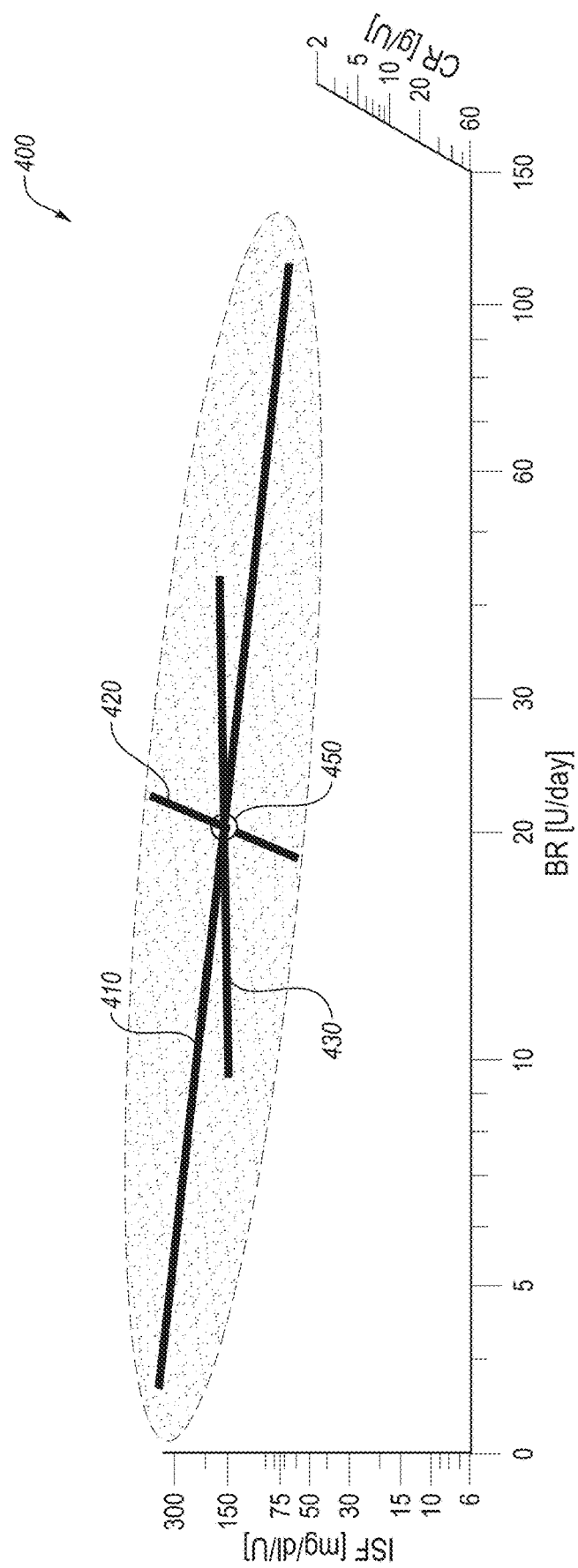
FIGS. 4A and 4B illustrate an example visualization of a probability distribution of a general BR, general CR, and general ISF.
Figure 4B:
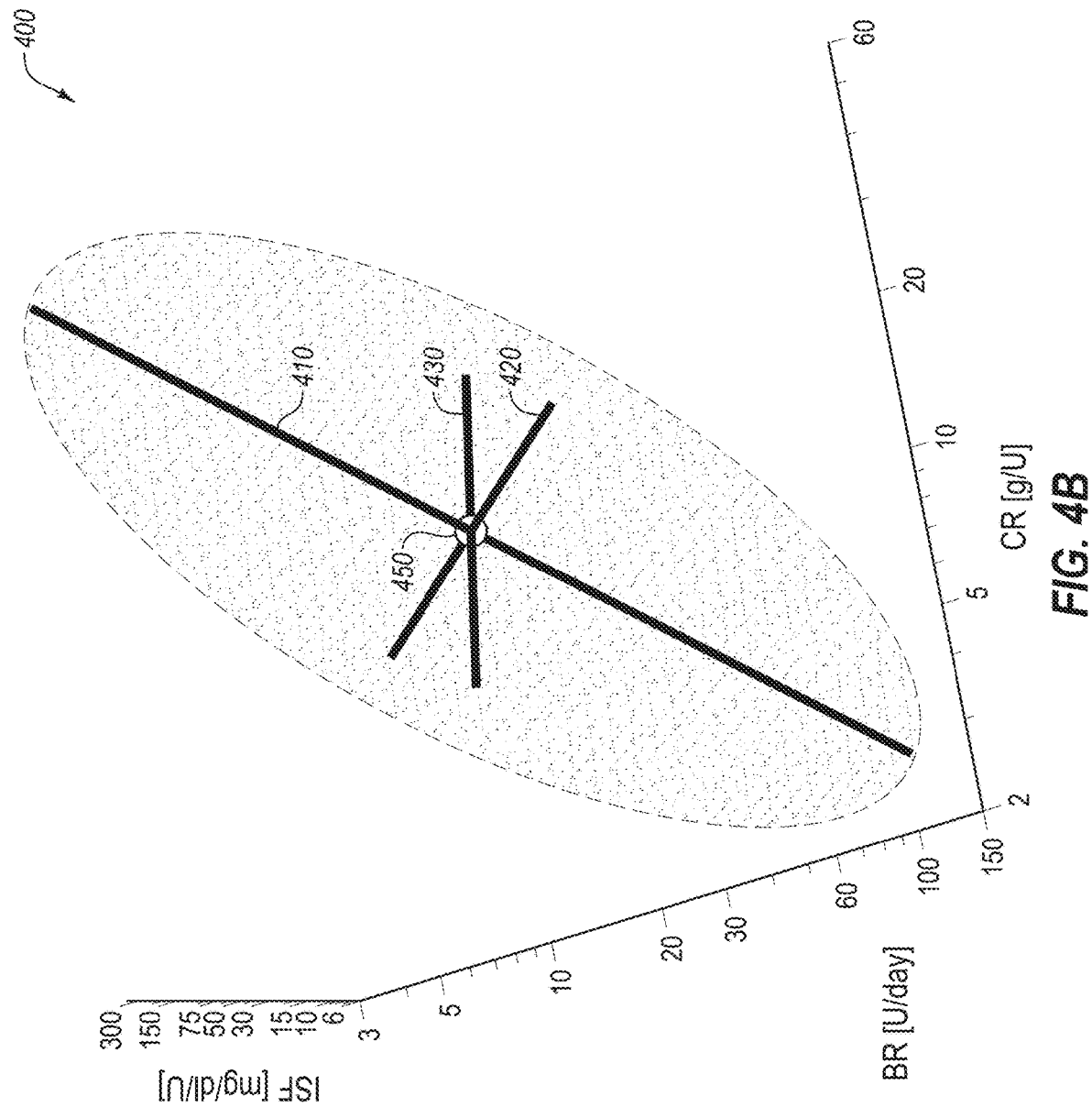

FIGS. 4A and 4B illustrate an example visualization 400 of a probability distribution of a general BR, general CR, and general ISF, in accordance with one or more embodiments of the present disclosure. As illustrated in FIGS. 4A and 4B, the probability distribution includes a generally ellipsoidal distribution with a major axis 410, and first minor axis 420 and second minor axis 430. The distribution also has a midpoint 450. The closer a combination of BR, CR, and ISF are to the midpoint 450, the closer the combination is to the middle of the distribution. In particular, the visualization 400 of FIGS. 4A and 4B represents a multivariate normal distribution of the logarithms of BR, CR, and ISF.

The multivariate normal distribution illustrated in FIGS. 4A and 4B may include a mean μ that is approximately $$\mu = \begin{bmatrix} 3.0111 \\ 2.3757 \\ 3.8645 \end{bmatrix}$$

and a covariation matrix Σ that is approximately $$\sum = \begin{bmatrix} 0.2843 & -0.1657 & -0.2216 \\ -0.1657 & 0.1978 & 0.1863 \\ -0.2216 & 0.1863 & 0.2968 \end{bmatrix}.$$

In some embodiments, a distance of a combination of BR, CR, and ISF from the probability distribution may be determined mathematically. For example, the Mahalanobis Distance, $D_m$ of an observed relationship of BR, CR, and ISF (e.g., the combination of entered therapeutic values as a matrix) may be determined by:

$$D_m = \sqrt{(x-\mu)^T \Sigma^{-1}(x-\mu)} \quad \text{Equation (3)}$$

The probability accumulated in the region bounded by the ellipsoid of FIGS. 4A and 4B with Mahalanobis Distance, $D_m$ may be determined by:

$$P(\|x-\mu\|_\Sigma \leq D_m) = \frac{\gamma\left(\frac{3}{2}, \frac{D_m^2}{2}\right)}{\Gamma\left(\frac{3}{2}\right)} \quad \text{Equation (4)}$$

Where 3 is used as the number of dimensions (e.g., the values of BR, CR, and ISF), $$\gamma\left(\frac{3}{2}, \frac{D_m^2}{2}\right)$$

is the lower incomplete Gamma Function, and $$\Gamma\left(\frac{3}{2}\right)$$

is the Gamma Function. The result of Equation (4) may yield a number between 0 (close to the midpoint 450) and 1 (far from the midpoint 450).

Using the approach above, the following example determines how uncommon the relationship between BR, CR, and ISF is if a user enters BR=16, CR=12, and ISF=130.

$$x = \ln[16 \quad 12 \quad 130]^T = [2.77 \quad 2.48 \quad 4.87]^T$$

$$D_m^2 = (x-\mu)^T \sum\nolimits^{-1}(x-\mu) =$$

$$\begin{bmatrix} -0.2384 \\ 0.1092 \\ 1.0030 \end{bmatrix}^T \begin{bmatrix} 9.0831 & 2.9883 & 4.9060 \\ 2.9883 & 13.3501 & -6.1487 \\ 4.9060 & -6.1487 & 10.8917 \end{bmatrix} \begin{bmatrix} -0.2834 \\ 0.1092 \\ 1.0030 \end{bmatrix} = 7.78$$

-continued $$P(\|x-\mu\|_\Sigma \leq D_m) = \frac{\gamma\left(\frac{3}{2}, \frac{D_m^2}{2}\right)}{\Gamma\left(\frac{3}{2}\right)} = \frac{\gamma\left(\frac{3}{2}, \frac{7.78}{2}\right)}{\Gamma\left(\frac{3}{2}\right)} = \frac{0.8412}{0.8862} = 0.949$$

$$(1 - 0.949) \times 100\% = 5.1\%$$

Thus, with the combination of therapeutic parameters of BR=16, CR=12, and ISF=130, only 5.1% of the population lies further from the midpoint 450 of the ellipsoid of FIGS. 4A and 4B.

Additionally or alternatively, in some embodiments a determination may be made as to how far from the major axis 410 a particular combination of therapeutic parameters falls. For example, a determination may be made as to the closest point on the major axis 410 from the particular combination of therapeutic parameters. A Mahalanobis Distance from the closest point on the major axis 410 to the midpoint 450 of the ellipsoid may be determined, yielding a value between 0 (at the midpoint 450) and 1 (very far from the midpoint 450). A numerical value of the distance from the major axis may be determined by Equation (5):

$$\text{PrDist}_{MajAx} = ((1-\text{Distance to midpoint})/(1-\text{Distance to major axis})) \quad \text{Equation (5)}$$

where $\text{PrDist}_{MajAx}$ is a numerical value between 0 (close to the major axis 410) and 1 (far from the major axis 410), Distance to midpoint is the result from Equation (4), and Distance to major axis is the Mahalanobis Distance from the closest point on the major axis 410 to the midpoint 450 of the ellipsoid.

Figure 5:
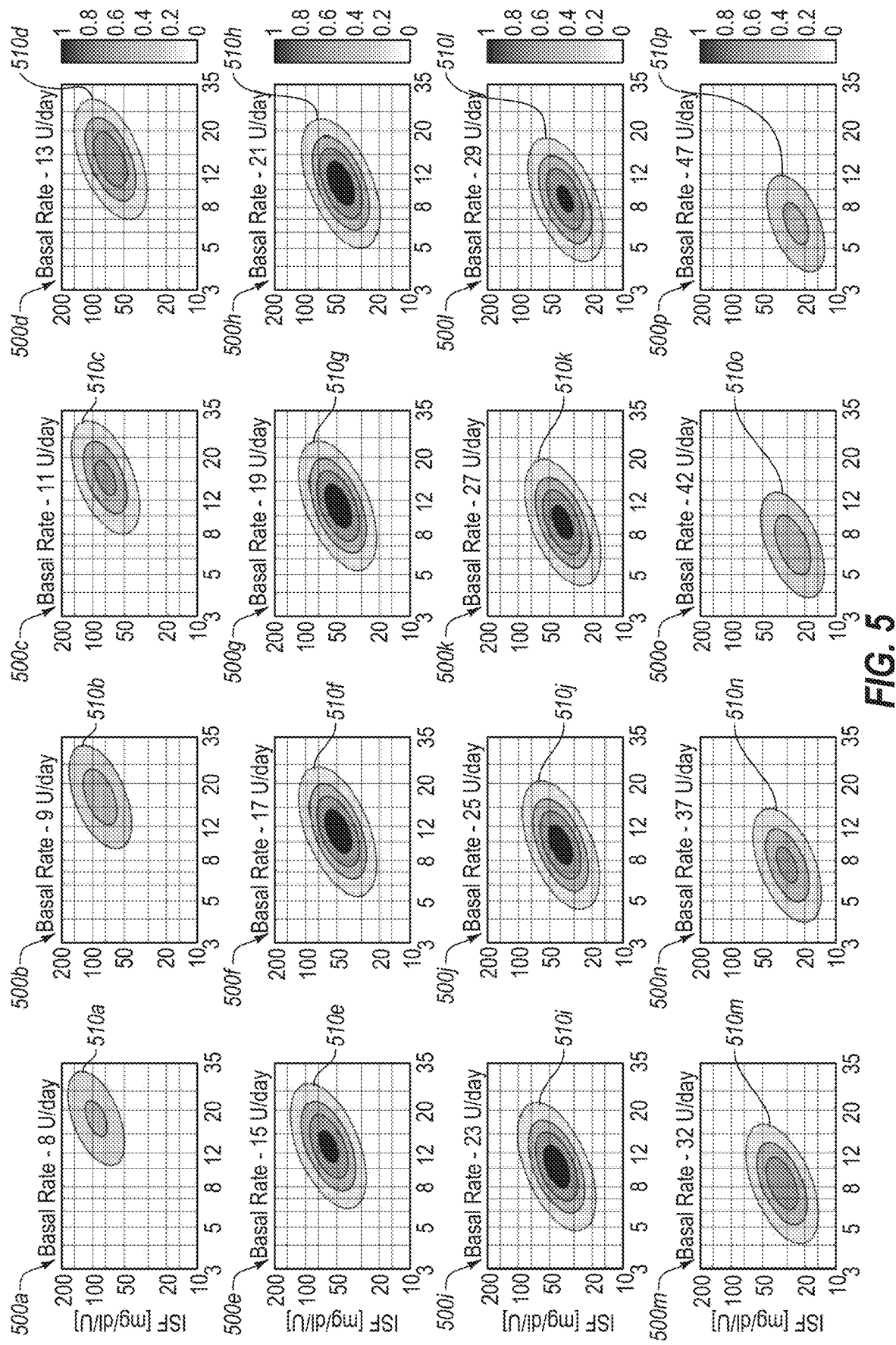
FIG. 5 illustrates example visualizations of probability distributions of CR and ISF for a given BR.

FIG. 5 illustrates example visualizations 500 of probability distributions 510 of CR and ISF for a given BR. For example, the visualizations 500 may represent slices of the ellipsoid of FIGS. 4A and 4B at various values of BR.

The visualization 500a illustrates a visualization of a probability distribution 510a of CR and ISF for a BR of 8 U/day. For example, for a BR of 8 U/day, the highest probability of ISF/CR is approximately 75-100/15-20. However, the probability of these values is still low as compared to other values of BR, such as the visualization 500g of a BR of 19 U/day with a much higher probability with ISF/CR of approximately 40-65/9-13.

In some embodiments the visualizations 500a-500p may include color gradations or other methods to illustrate variations in probability. Additionally or alternatively, the probability distributions 510a-510p may include one or more bands of one or more thresholds of probabilities. For example, the visualization 500g may include four concentric bands of probabilities. For the given BR of 19 U/day, as the combination of ISF/CR associated with the given BR moves closer to the center of the concentric band, the closer the combination comes to the most probable combinations of therapeutic parameters.

In some cases, methods and systems provided herein can display a visualization showing a probability distribution of ISFs and CRs for an entered BR with concentric bands of constant probability. Additionally or alternatively, the visualization may include an indicator of the input combination of ISF and/or CR. Additionally or alternatively, a suggestion can be given to the user that the ISF and/or CR be adjusted to place the PWD's therapeutic parameters at a position on the visualization closer to the increased probability of the general distribution.

Figure 6:
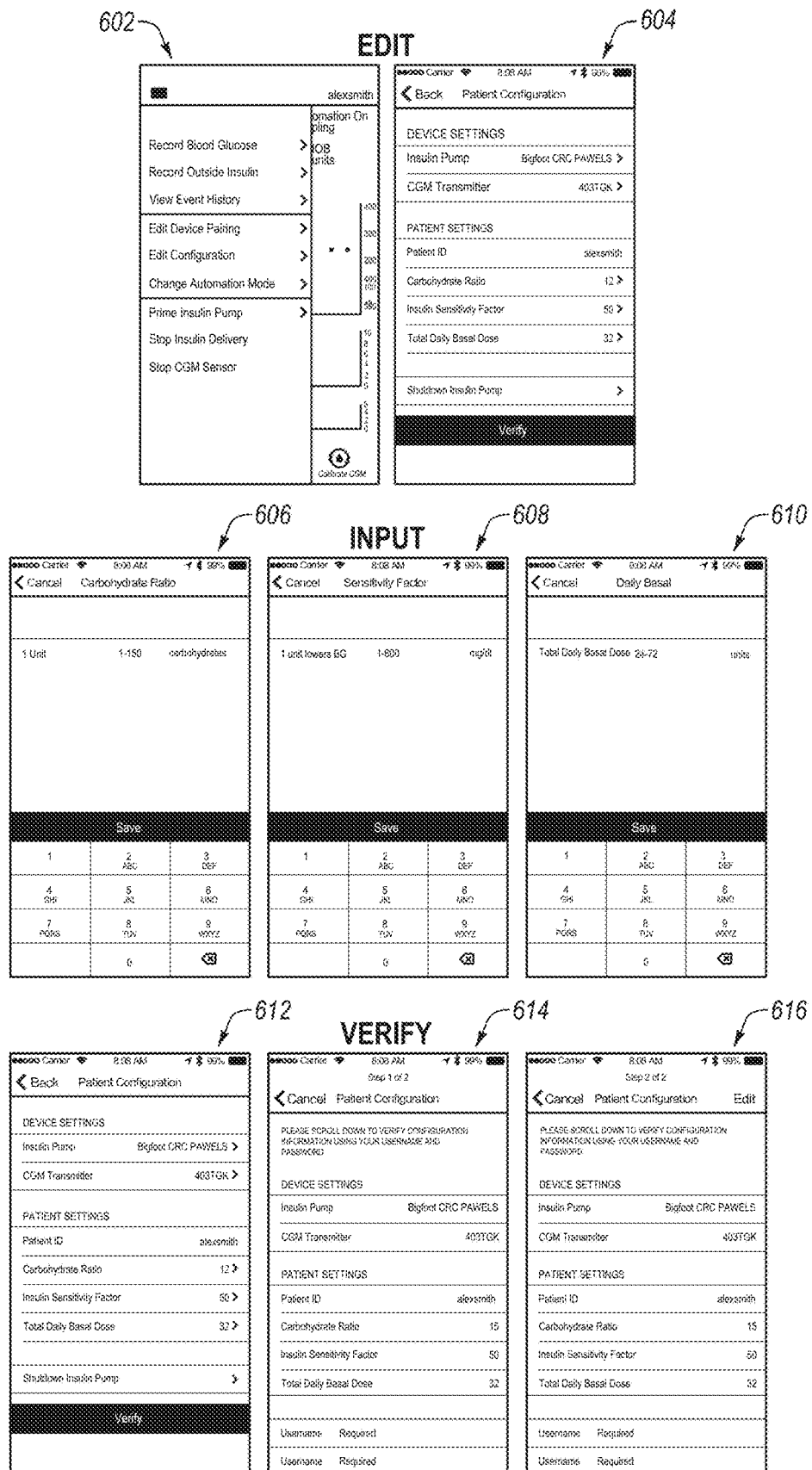
FIG. 6 illustrates an example view of various user interfaces that may facilitate entering one or more therapeutic parameters.

FIG. 6 illustrates an example view of various user interfaces that may facilitate entering one or more therapeutic parameters, in accordance with one or more embodiments of the present disclosure. The various user interfaces may be used to edit, input, and/or verify various therapeutic parameters.

As illustrated in user interfaces 602 and 604, a user may select a menu option to edit one or more therapeutic parameters associated with a diabetes management system (such as the diabetes management system 10 of FIG. 1). For example, the user interface 602 may illustrate an option to edit various parameters of a diabetes management system and with the user interface 604, a user may select one or more therapeutic parameters to modify or edit.

As illustrated in the user interfaces 606, 608, and 610, a user may manually input numerical values for one or more therapeutic parameters. For example, via the user interface 606, a user may input a CR, via the user interface 608, a user may input an ISF, and via the user interface 610, a user may input a BR.

As illustrated in the user interfaces 612, 614, and 616, a user may verify one or more therapeutic parameters. For example, via the user interface 612 a user may review one or more manually input therapeutic parameters, via the user interface 614, the user may input authenticating credentials to verify that the user is authorized to modify therapeutic parameters, and the user interface 616 may be a confirmation of the modified parameters.

Figure 7:
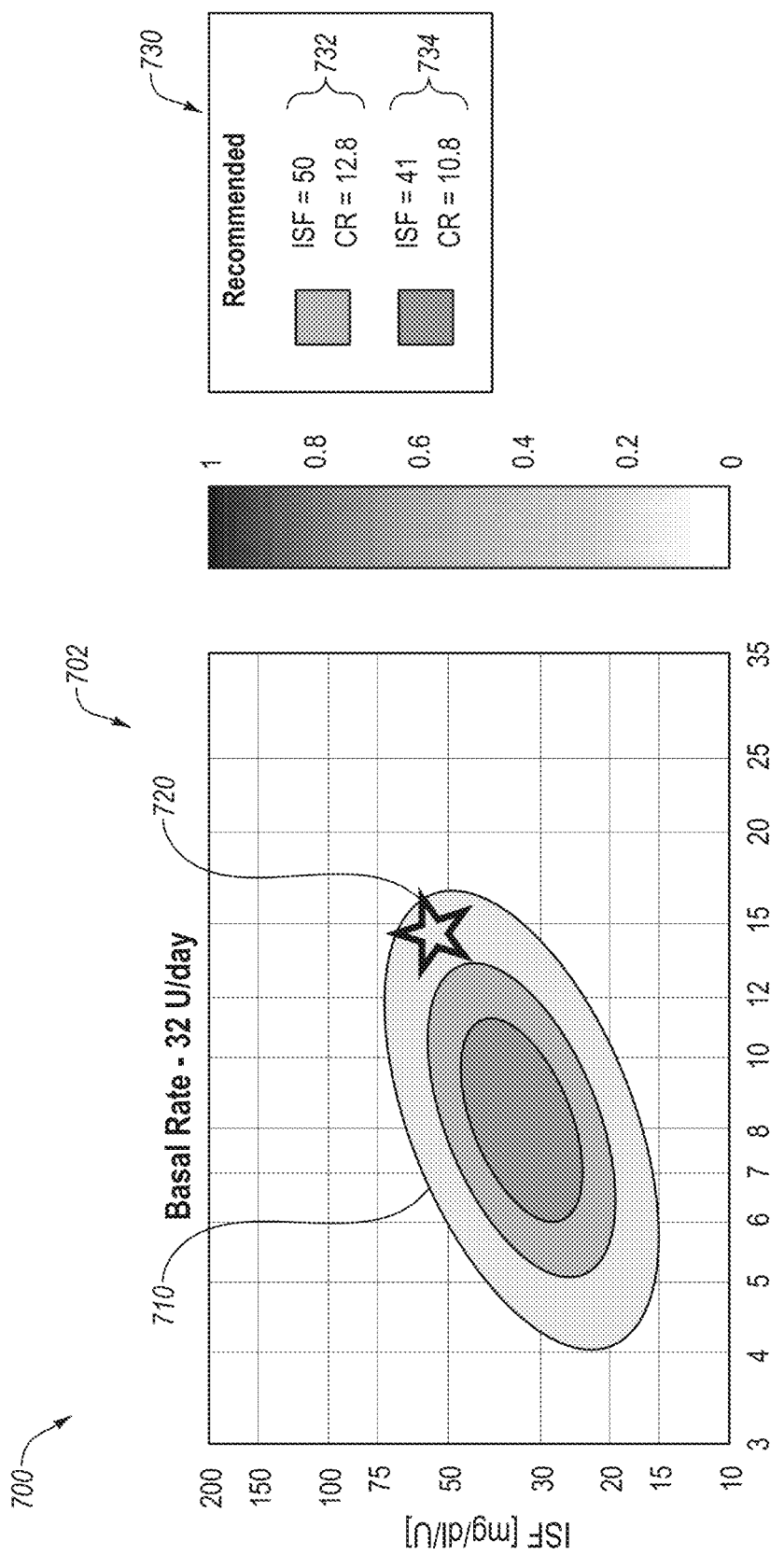
FIG. 7 illustrates an example user interface providing a recommendation of one or more therapeutic parameters.

FIG. 7 illustrates an example user interface 700 providing a recommendation of one or more therapeutic parameters, in accordance with one or more embodiments of the present disclosure. For example, the user interface 700 includes a visualization 702 that may include a probability distribution 710 for an entered BR. Additionally or alternatively, the visualization 702 of the user interface 700 may include an indicator 720 indicating where in the probability distribution 710 the entered combination falls. For example, as illustrated in the visualization 702, the indicator 720 corresponding to the entered combination of therapeutic parameters falls toward the outside of the outer-most band of the probability distribution 710.

In some embodiments, the user interface 700 may additionally include a recommendation window 730. The recommendation window 730 may include one or more recommendations for variations in ISF and/or CR to move the combination of therapeutic parameters into a lower band of the probability distribution 710. For example, the recommendation window 730 may include a first recommendation 732 of ISF and/or CR to move the therapeutic parameter combination within the next band, and a second recommendation 734 of ISF and/or CR to move the therapeutic parameter combination within the most central band of probabilities. In these and other embodiments, the recommendations of the recommendation window 730 may be color-coded or otherwise matched to the corresponding bands of probability such that a visual indicator of a region or band of probability is associated with a recommendation.

Modifications, additions, or omissions may be made to any of the visualizations and/or user interfaces of FIGS. 5-7. For example, any determinations or comparisons may be used to generate the various visualizations and/or user interfaces. As another example, the visualizations may be modified such that rather than slices based on a particular BR, the visualizations may be slices based on ISF and/or CR. As another example, any style or format of user interface may be utilized. As another example, embodiments illustrated in FIGS. 5-7 may have more or fewer elements than those illustrated or described in the present disclosure. For example, any number of the user interfaces of FIG. 6 may be omitted. Additionally, any number of recommendations may be provided in FIG. 7, including at the midpoint, at the edge of each band, etc. As another example, a line from the manually entered combination of therapeutic parameters and the midpoint may be illustrated with a slider along the line such that a user may select any point between the entered therapeutic parameter combination and the midpoint. As another example, the user may be able to select any point in the visualization 702 of FIG. 7 and be provided a numerical indication of the combination of therapeutic parameters for the selected point.

Personalization Modifications

In some cases, methods and systems provided herein automate the delivery of insulin based on continuous or semi-continuous blood glucose data and make adjustments to one or more therapeutic parameters based on the automation of insulin delivery. For example, if a system or method provided herein increases a basal rate or provides an automatic correction bolus, methods and systems provided herein can also increase the BR for a subsequent day (or the BR for a subsequent day for that time of the day). In some cases, ISF and CR can also be adjusted for future time periods in response to the automation of insulin delivery.

Figure 8:
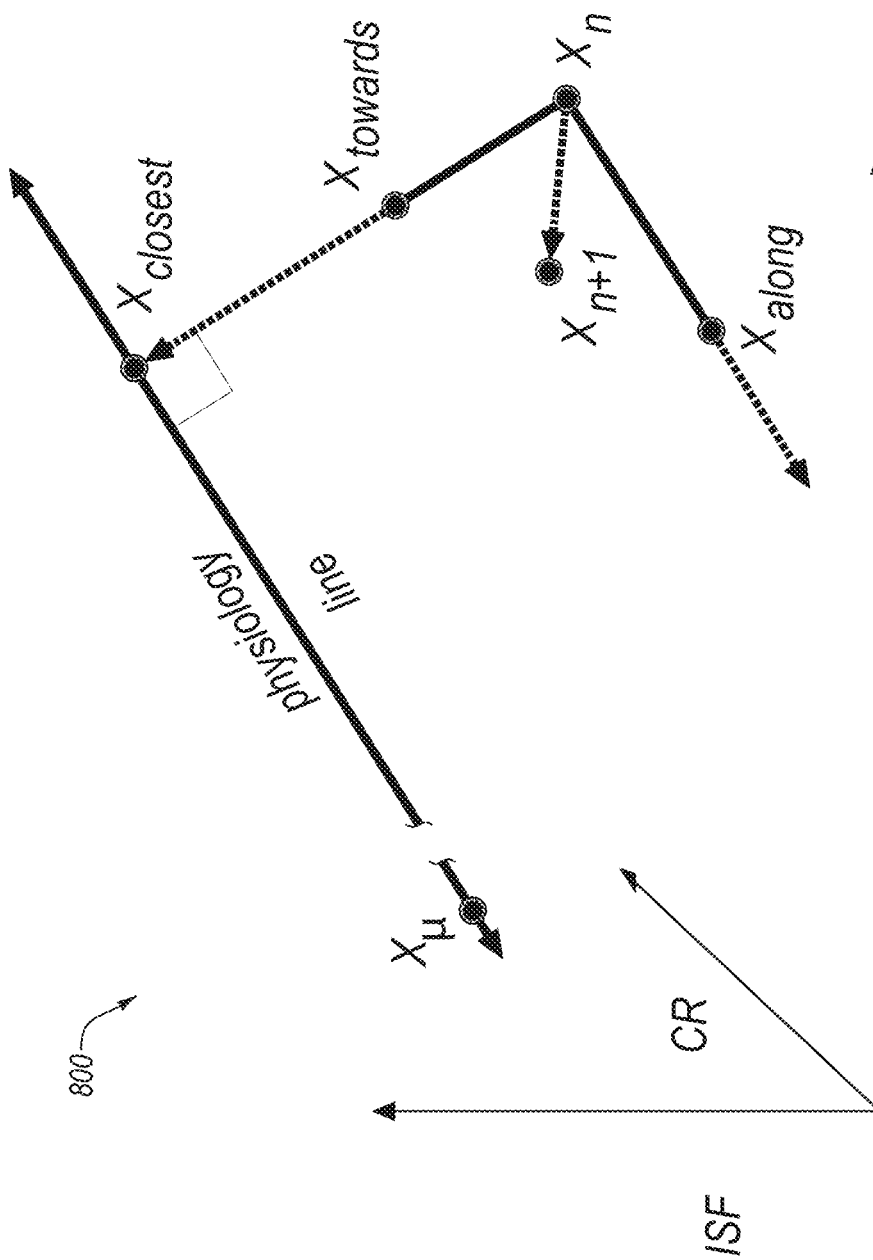
FIG. 8 illustrates an example visualization of adjusting one or more therapeutic parameters.

FIG. 8 illustrates an example visualization 800 of adjusting one or more therapeutic parameters, in accordance with one or more embodiments of the present disclosure. The physiology line may be similar or comparable to the major axis 410 of FIGS. 4A and 4B. The point $X_n$ may represent a given combination of therapeutic parameters, including ISF, CR, and/or BR. In some embodiments, the personalization of therapeutic parameters for a PWD may include a combination of adjusting with a partial step toward the closest point along the physiology line and a partial step along the physiology line, yielding a new set of therapeutic parameters $X_{n+1}$. For example, methods and systems of the present disclosure may determine that after a given day the BR should be adjusted based on repeatedly delivering 2× a baseline basal rate for multiple consecutive diurnal time blocks during that given day. Methods and systems of the present disclosure may also adjust CR and/or ISF such that the combination of BR, CR, and ISF may move partially toward the physiology line and partially parallel to the physiology line.

In some cases, adjustments to ISF, CR, and/or BR can be made in lockstep along a predetermined mathematical relationship between ISF, CR, and BR established when those settings are entered. Such relationships may be similar or comparable to those described in the present disclosure with respect to the relationship between the various therapeutic parameters. In some cases, each of ISF, CR, and BR can be adjusted by a fixed percentage up or down in response to automated insulin deliveries. In other cases, ISF, CR, and BR can be independently adjusted with or without automated insulin deliveries.

In some cases, methods and systems using automated insulin delivery can purposefully add noise to the system in order to observe a reaction to make fine-tuned adjustments to a relationship between BR, ISF, and CR.

Modification Associated with Bolus Doses

In some cases, methods and systems provided herein can automate insulin delivery, but also provide recommended bolus insulin amounts that a user can manually adjust. A recommended bolus insulin amount may have a correction bolus component (calculated by dividing the current blood glucose level minus the target blood glucose value by the ISF) and a meal bolus component (carbohydrates divided by CR).

FIGS. 9A and 9B illustrate example user interfaces for entering a bolus dose, in accordance with one or more embodiments of the present disclosure. For example in FIG. 9A, the user interface 900a illustrates a data entry field where a user may enter the amount of carbohydrates that a PWD will be consuming. The user interface 900a may include an indication 910 of the total insulin that is recommended that may account for both any correction bolus and/or a meal bolus. In some embodiments, the recommended dose of the indication 910 may be delivered without any user modification. For example, a message may be sent from the device displaying the user interface 900a to an insulin pump or an insulin pen to deliver the recommended bolus dose. In some cases, the user may manually adjust the recommended dose.

The user interface 900b of FIG. 9B illustrates an ability of the user to manually adjust or override the recommended dose. The user interface 900b may include an indication 912 of the recommended dose that may be similar or comparable to the indication 910 of FIG. 9A. The user interface 900b may additionally include a data entry feature 920 via which the user may manually adjust the bolus dose. In these and other embodiments, a visual indicator (for example, "+," "−," or colored in red or green) may indicate whether the user is increasing or decreasing the recommended dose. In some cases, a safeguard may prevent the user from adjusting the bolus dose beyond a threshold distance from the recommended dose, such as 15%, 25%, 50%, etc.

In methods and systems that automate insulin delivery, a manual change to a bolus may typically result in an adjustment to subsequent basal insulin deliveries. For example, a manual increase from a recommended bolus may typically result in a reduction or stopping of the delivery of basal insulin and a manual decrease from a recommended bolus may typically result in an increase in the delivery of basal insulin or the automatic delivery of a correction bolus. In some cases, methods and systems provided herein can lockout the personalization of BR subsequent to a bolus where the user manually changes the bolus amount for a predetermined or variable amount of time. For example, if a user were to adjust a bolus dose higher, the automated system may deliver 0× the baseline basal rate for one or more next delivery actions according to a delivery profile as described herein. In some cases, the adjustment to a ratio of the baseline basal rate may be disabled such that the baseline basal rate is delivered for one or more delivery actions following the bolus dose. As another example, at the end of a given day one or more baseline basal rates for diurnal time blocks during the day may be analyzed and modified for future days as described herein (such as for the same diurnal time block but on another day, or a diurnal time block one or two segments earlier than the particular diurnal time block, or a diurnal time block at least 20 hours in the future). In some cases, a certain amount of time following the bolus dose may be excluded from the analysis to determine if the baseline basal rate is to be modified. In some cases, ISF and/or CR may be adjusted while BR may be locked out. Additionally or alternatively, ISF and/or CR may also be locked out from modification.

In some cases, ISF and CR can be personalized in response to a user manually adjusting a recommended bolus to align the ISF and CR to the user's subjective expectation of how much insulin should be delivered for a bolus, with the amount of adjustment being in relationship to the amount of the bolus being attributable to a correction and the amount of the bolus being attributable to a meal.

For example, for a given PWD with a CR of 15, ISF of 50, a target blood glucose level of 120, a current blood glucose level of 170 and an upcoming meal of 30 carbs, the recommended bolus may be determined by the correction bolus (170−120)/50=1 Unit and the meal bolus (30/15)=2 Units, or 3 Units total. If the user were to adjust the bolus dose to 4 units, the ratio of correction to meal bolus is 1:2, and the proportional adjustment to equal 4 units would be the correction dose is 1.33 Units and the meal bolus is 2.67 Units. To change the ISF and CR to more closely align with the subjective expectation of the user, an incremental step may be taken toward the subjective expectation. For example, the complete subjective expectation for ISF may be 50/1.33, or 37.5 and for CR may be 30/2.67 or 11.23. If the incremental step were 10% toward the subjective expectation, the adjusted ISF may be 48.75 and the adjusted CR may be 14.6 for the given diurnal time block. In some embodiments, such a modification may be adjusted and/or smoothed as compared to adjacent diurnal time blocks as described herein with reference to FIG. 22.

In some cases the override may be attributed entirely to one or more components of a bolus dose, e.g., a meal component or a correction component. For example, assuming the recommended bolus of 3 Units, above, if the user were to adjust the bolus dose to 4 units, the entire additional 1 Unit would be attributed to the meal component, or 1 Unit attributed to the correction component and 3 Units attributed to the meal component. In one embodiment, the entire change to the meal component may be attributed to carbohydrate intake. Various user specific dosage parameters may be determined and/or adjusted responsive to the assumption that the entire change to the meal component is attributed to carbohydrate intake. An amount of carbohydrate intake (typically in grams) may be calculated based on the meal component of 3 Units using the equation, meal component=carbohydrates divided by CR. In one embodiment, the amount of carbohydrates may be used to estimate the future blood glucose levels, and in further embodiments may be used to adjust a BR. In one embodiment, adjusting the BR may involve selecting and/or changing an insulin delivery profile for a given diurnal time block. Of course, one of ordinary skill in the will recognize cases where the meal component may not be entirely attributed to carbohydrate intake, and a determination of carbohydrate intake may be a fraction of the meal component, for example, a proportion attributed to a meal component.

In some cases, such a lockout of changes to BR and/or change of ISF and CR in response to manual changes to a recommended bolus can prevent the automated system from inappropriately adjusting therapeutic parameters in a hybrid closed-loop system for users who do not follow recommendations. Such a lockout and/or modification of therapeutic parameters may additionally adjust the system to more closely match the subjective expectations of the user such that an appropriate amount of insulin is being delivered despite the modification by the user. In some cases, methods and systems provided herein may provide such a lockout any time a bolus dose is delivered. Such an embodiment may provide a tradeoff of customizability for ease of calculation and reduction in processing requirements of a determining device.

In some cases, methods and systems can provide notices to users that consistently upwardly or downwardly adjust recommended boluses that the system is seeking to personalize the recommended bolus amounts to their individual physiology and that a routine upward or downward adjustment by the user to the recommended bolus may negatively impact the therapeutic decisions made by the system. For example, methods and systems of the present disclosure may monitor a number of times that a user has manually adjusted a recommended bolus dose and/or monitor the magnitude of an adjustment to a recommended bolus dose. If the number of times or magnitude of adjustment exceeds a threshold, a message may be generated regarding the user modification. In some cases, the threshold may include adjusting the recommended dose just one time, or the magnitude may include any change. Messages regarding a user overriding the recommended bolus dose may be provided to a PWD and/or to a caregiver of the PWD.

In some cases, methods and systems provided herein may notice or detect that there was an occlusion and that insulin believed to have been delivered was not actually delivered. In response to such undelivered insulin, methods and systems provided herein can change the method for personalizing therapeutic parameters. For example, the system may adjust the insulin on board calculation or other metrics to accurately track the amount of insulin actually delivered rather than the amount of insulin believed to be delivered. As another example, the ISF, CR, and/or BR may be locked out from adjustment for the time periods that were affected by the occlusion.

In some cases, a PWD may be transitioning from an injection based insulin delivery system (e.g., syringes, pens, or the like) to a pump based insulin delivery system. In these and other cases, methods and systems of the present disclosure may utilize a scaled back daily basal rate. For example, the scaled back daily rate may be between approximately 85% and 95% of a basal rate utilized in the injection based system. Such an adjustment may be based on shifting from long acting insulin delivered via an injection delivery system to supply the basal insulin, to utilizing quick acting insulin delivered via a pump delivery system to supply the basal insulin.

In some cases, methods and systems provided herein can personalize BR, CR, and ISF with blood glucose data taken using finger stick blood glucose tests. For example, personalization may occur based on any number of finger stick blood glucose tests, such as between 1 and 10 times a day.

In some cases, BR, one or more timestamped fingerstick blood glucose samples ($MBG_i$), and, optionally, bolus insulin ($bolus_j$) samples can be taken throughout the day. If boluses are used, the bolus Insulin on Board ($IOB_{bolus}$) is calculated at times i based on boluses at time j Basal Insulin on Board ($IOB_{basal}$) can also be calculated. The IOB may be determined as described herein. For personalization using mean blood glucose (MBG) data only, a metric of how much of the insulin is based on basal as opposed to bolus ($w_i$) may be utilized where $w_i=0.975$. For personalization using MBG and insulin data, let $w_i=IOB_{basal,i}/(IOB_{bolus,i}+IOB_{basal,i})$.

At the end of a day, the physiological values BR, CR, and ISF may be updated as follows. An assumption may be made that the physiological values for BR, CR, and ISF, lie along the "physiology line" illustrated in FIG. 8 and described by the equation:

$$\begin{bmatrix} \ln(BR) \\ \ln(CR) \\ \ln(ISF) \end{bmatrix} = x_\mu + tm = \begin{bmatrix} \ln(\mu_{BR}) \\ \ln(\mu_{CR}) \\ \ln(\mu_{ISF}) \end{bmatrix} + t\begin{bmatrix} m_{BR} \\ m_{CR} \\ m_{ISF} \end{bmatrix} = \begin{bmatrix} \ln(20.3) \\ \ln(10.8) \\ \ln(47.7) \end{bmatrix} + t\begin{bmatrix} 1.00 \\ -0.80 \\ -1.05 \end{bmatrix} = \begin{bmatrix} 3.01 \\ 2.38 \\ 3.86 \end{bmatrix} + t\begin{bmatrix} 1.00 \\ -0.80 \\ -1.05 \end{bmatrix}$$

where t is an arbitrary scalar.

$BR_0$, $CR_0$ and $ISF_0$ may be used to represent the starting values for personalizing the therapeutic parameters. As described in the present disclosure, if only $BR_0$ is known, one or both of ISF and/or CR may be determined. For example, if only $BR_0$ is known, $$\ln(CR_0)=4.79-0.80 \ln(BR_0) \text{ and}$$

$$\ln(ISF_0)=7.03-1.05 \ln(BR_0)$$

Personalizing one or more of the therapeutic parameters may include incrementally moving daily settings of the therapeutic parameters closer to the "physiology line" of FIG. 8. For example, the therapeutic parameters may be personalized by taking the average $x_{n+1}$ of a) a partial step toward the closest point $x_{closest}$ on the physiology line, $x_{towards}$, and b) a partial step along the physiology line, $x_{along}$.

$$x_{closest}=x_\mu+[(x_n-x_\mu)\cdot m][m\cdot m]^{-1}m$$

$$x_{towards}=x_n+\text{speed}_{towards}(x_{closest}-x_n)$$

where $\text{speed}_{towards}$ represents how quickly the system shifts the therapeutic parameters toward the physiology line. This value may take any numerical value between 0 and 1. For example, a value of 0.5 may be used, or some other numeric value may be used to adjust how quickly the system shifts the therapeutic parameters toward the physiology line. Additionally, m represents the line parallel to the physiology line along which $x_n$ lies.

$$x_{along}=x_n+\text{speed}_{along}m$$

where $\text{speed}_{along}$ represents how far the therapeutic parameters are modified along a direction parallel to the physiology line.

$$\text{speed}_{along}=0.1\frac{\text{mean}(w_i\ln(MBG_i/\text{setpoint}))}{\text{mean}(w_i)}$$

where setpoint may represent a target value of target blood glucose level. Thus, to find the new therapeutic parameter set personalized based on the previous data, the new set may be defined by:

$$x_{n+1}=(x_{towards}+x_{along})/2$$

Personalization Based on Bolus Doses

In some cases, the present disclosure may include personalization that may occur in the delivery of insulin that is further personalized based on the delivery of bolus doses. For example, as described herein, personalization may occur at a first level by adjusting the delivery of insulin to be a multiple or ratio of a baseline basal rate for a user, such as delivering 0×, 1×, or 2× of the baseline basal rate. Personalization may also occur at a second level by analyzing what multiple or ratio of the baseline basal is delivered for a diurnal time period and adjusting the baseline basal rate for that diurnal time period or a related diurnal time period based on what adjustments were made in the personalization at the first level. For example, if the user received 2× of the baseline basal rate for an entire diurnal time period, the baseline basal rate may be increased for that diurnal time period or a related diurnal time period in the future.

In some cases, a bolus that is delivered to a user may be treated as a series of rate increases for a given time period. For example, if a user was receiving 1× of the baseline basal rate for two hours and at the end of the two hours received a correction bolus, the correction bolus may be treated as a series of times that 2× of the baseline basal rate was delivered to the user. In such a case, such a system may personalize at the second level based on boluses, in addition to personalizations done at the first level.

Figure 10:
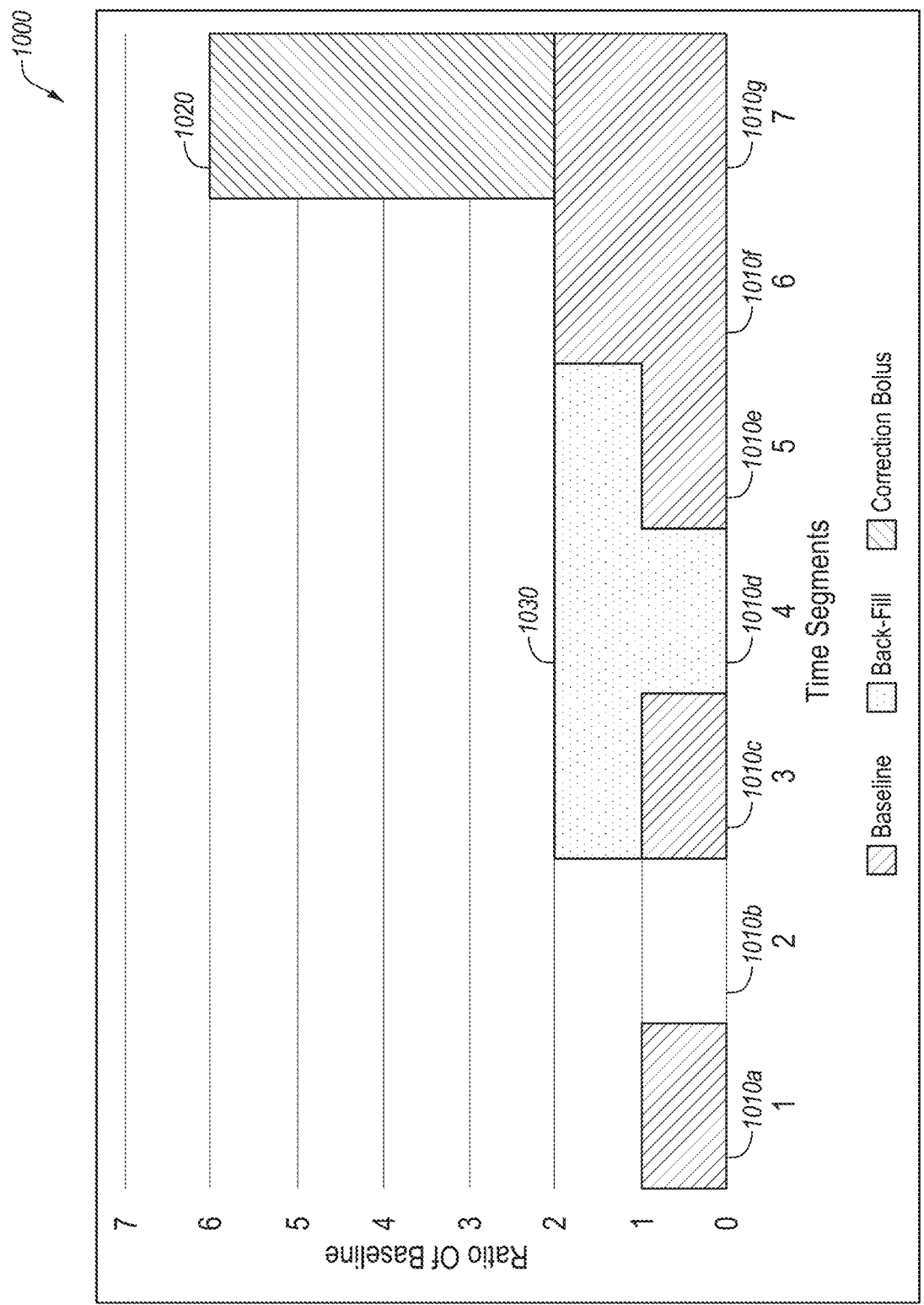
FIG. 10 illustrates an example graph illustrating a visualization of back-filling based on a correction bolus.

FIG. 10 illustrates an example graph 1000 illustrating a visualization of back-filling based on a correction bolus. Along the x-axis of the graph 1000 are time segments, and along the y-axis of the graph 1000 are ratios of a baseline basal rate. FIG. 10 illustrates an example series of delivery actions 1010 based on a ratio of the baseline basal rate, including the delivery actions 1010a-1010g. FIG. 10 additionally illustrates an example correction bolus 1020.

As illustrated in FIG. 10, during the first time segment, a user may receive 1× of the baseline basal rate as the delivery action 1010a. Similarly, the user may receive 0× during the second time segment for the delivery action 1010b, 1× during the third time segment for the delivery action 1010c, 0× during the fourth time segment for the delivery action 1010d, 1× during the fifth time segment for the delivery action 1010e, 2× during the sixth time segment for the delivery action 1010f, and 2× during the seventh time segment for the delivery action 1010g. As illustrated, during the seventh time segment, the correction bolus 1020 may be delivered with an amount of insulin comparable to approximately 4× of the baseline basal rate in addition to the baseline basal insulin delivered at 2× the baseline basal rate.

After receiving the correction bolus 1020, a control device may back fill one or more of the time segments in which the first level of personalization had availability to deliver a higher amount of insulin. For example, with reference to FIG. 10, the delivery action 1010e during the fifth time segment delivered 1× the baseline basal rate, and the control device may change the delivery amount to 2× such that as personalization at the second level is performed for a diurnal time block including the fifth time segment, the personalization at the second level will account for a 2× delivery during the fifth time segment rather than a 1× delivery. Thus, the historical delivery of basal insulin used in personalization at the second level may be adjusted such that the correction bolus is accounted for in the historical delivery information.

In some embodiments, the control device may obtain the maximum baseline basal rate available for personalization at the first level. For example, the personalization at the first level may allow delivery of 0×, 1×, and 2×, or may allow any other ratio or multiple of the baseline basal rate, such as 3×, 5×, or others. In these and other embodiments, the control device may determine what time segments had potential insulin delivery segments. The term insulin delivery segments may refer to one delivery action of the baseline basal rate, or a 1× delivery action. For example, with reference to FIG. 10, the delivery action 1010a may fill one insulin delivery segment. In some embodiments, the insulin delivery segments identified as potential may be available over a back-fill time, or may be limited to insulin delivery segments within the back-fill time. The back-fill time may be a static time value, such as one hour, two hours, three hours, four hours, six hours, twelve hours, or others. Additionally or alternatively, the back-fill time may be based on one or more attributes of the user, such as ISF, CR, or others. For example, with reference to FIG. 10, the back-fill time may be the previous six time segments.

With reference to FIG. 10, based on a maximum delivery of 2× and the back-fill time including the previous six time segments and the delivery actions 1010, FIG. 10 illustrates one insulin delivery segment available in the first time segment, two insulin delivery segments available in the second time segment, one insulin delivery segment available in the third time segment, two insulin delivery segments available in the fourth time segment, and one insulin delivery segment available in the fifth time segment. Thus, with reference to FIG. 10, there may be seven insulin delivery segments potentially available to be back-filled during the back-fill time.

In some embodiments, the control device may determine the amount of cumulative IOB if all of the insulin delivery segments were filled. For example, with reference to FIG. 10, the control device may determine what the cumulative IOB would be at the time of the correction bolus if all seven insulin delivery segments were back filled such that 2× of the baseline basal insulin rate had been delivered for each of the time segments during the back-fill time. The IOB may be determined as described herein.

In some embodiments, the control device may determine how many insulin delivery segments to back fill based on one or more criteria. For example, the control device may determine how many insulin delivery segments to back-fill based on determining what the cumulative IOB would be right before delivery of the correction bolus based on back-filling one or more insulin delivery segments. For example, with reference to FIG. 10, the control device may determine that the correction bolus includes 1.2 U insulin. The control device may determine that back-filling all of the insulin delivery segments may result in an IOB of 1.8 U of insulin. The control device may then iteratively determine the IOB if fewer than all of the insulin delivery segments were back-filled, until the IOB is equal to or less than the correction bolus. In some embodiments, such an iterative process may proceed one insulin delivery segment at a time, or may follow any other algorithmic approach to identify the point at which the IOB is equal to or less than the correction bolus.

As another example, the control device may determine how many insulin delivery segments to back-fill based on the cumulative amount of insulin in the back-filled insulin delivery segments. For example, with reference to FIG. 10, the control device may determine that the correction bolus includes 1.2 U insulin. The control device may determine that back-filling all of the insulin delivery segments may include 2.1 U of insulin. The control device may then iteratively determine the cumulative amount of insulin if fewer than all of the insulin delivery segments were back-filled, until the cumulative amount of insulin is less than the correction bolus of 1.2 U of insulin. In some embodiments, such an iterative process may proceed one insulin delivery segment at a time, or may follow any other algorithmic approach to identify the first insulin delivery segment at which the cumulative insulin is less than the correction bolus.

In some embodiments, the control device may utilize more than one basis for determining the number of insulin delivery segments to back-fill. For example, for each iteration of back-filling an insulin delivery segment, the control device may check whether the IOB is equal to or less than the correction bolus and may also check whether the cumulative insulin of the back-filled insulin delivery segments is less than the correction bolus.

In some embodiments, after a number of the insulin delivery segments have been back-filled, the control device may perform a personalization at the second level (e.g., adjusting one or more of BR, CR, and ISF) based on the personalization that occurred at the first level and the back-filled insulin delivery time segments. For example, with reference to FIG. 10, after the back-filling, the historical insulin delivery information shows that 2× of the baseline basal insulin was delivered during the third, fourth, fifth, sixth, and seventh time segments. Thus, for a diurnal time period corresponding to those time segments, any personalization may occur, such as an increase of BR, decrease of CR, decrease of ISF, or any combinations thereof. In some embodiments, personalization at the second level may occur some time later than the back-filling. For example, the back-filling may occur concurrent with or within a short time (e.g., 5 minutes, 10 minutes, 30 minutes, 1 hour) of the correction bolus, and the personalization at the second level may occur a longer time later (e.g., 6 hours, 12 hours, 24 hours) after the correction bolus.

In some embodiments, a similar process of back-filling may occur for a negative correction bolus. For example, the control device may instruct a user that their blood glucose level is trending low and recommend that the user eat a certain number of carbohydrates to counteract the low blood glucose level. Additionally or alternatively, the control device may adjust a bolus during a meal or adjust the baseline basal insulin delivery to be below what is expected such that a negative correction bolus may be provided. For example, if a user has a certain CR and ISF such that a bolus calculator would normally recommend 2 U of insulin for a meal they are about to eat, the control device may instead recommend a bolus of only 1.2 U of insulin as a negative correction bolus. Based on the number of carbohydrates that a user indicates they have consumed, the number of carbohydrates recommended to be consumed, or the amount of insulin below the expected delivery, the control device may back-fill the insulin delivery segments to a lower historical delivery amount. For example, with reference to FIG. 10, if the control device had lowered a meal bolus rather than a correction bolus, one or more of the delivery actions 1010g and 1010f may be reduced from 2× to 1× or 0×, and one or more of the delivery actions 1010e, 1010c, and 1010a from 1× to 0×.

In some embodiments, back-filling to reduce the historical insulin delivery actions for a negative correction bolus may be based on the cumulative IOB. For example, the control device may readjust one or more of the insulin delivery actions and determine what a hypothetical IOB would have been based on the adjusted delivery actions. The control device may iteratively adjust the number of insulin delivery segments that are back-filled to reduce the insulin delivery actions until the reduction in IOB is equal to or less than the negative correction bolus, or the cumulative insulin reduction is less than the negative correction bolus.

In some embodiments, the basal adjustments may be represented mathematically by an equation correlating a correction bolus to a series of delivery actions:

$$\text{Correction Bolus}_t = \Sigma_{k=0}^{n} \alpha_i^k \text{action}_{t-k} \quad \text{Equation (6)}$$

where Correction Bolus$_t$ represents a correction bolus at time t, $BY_t = Y_{t-1}$, $B^2Y_t = Y_{t-2}$, $B^kY_t = Y_{t-k}$, $\alpha_i = e^{-ts/\tau_i}$, $\tau_i$ represents the insulin time constant (such as approximately 120 minutes), and action$_t$[U] represents an amount of insulin delivered for a time segment at the basal rate at time t.

Modifications, additions, or omissions may be made to FIG. 10 without departing from the scope of the present disclosure. For example, any number of time segments may be included in the back-fill time, such as one hour, two hour, three hours, four hours, five hours, or six hours. As another example, any number of correction boluses may be accounted for. As an additional example, any ratio of delivery may be included, such as 0×, 0.5×, 1×, 1.5×, 2×, 3×, 5×, or others.

Figure 11:
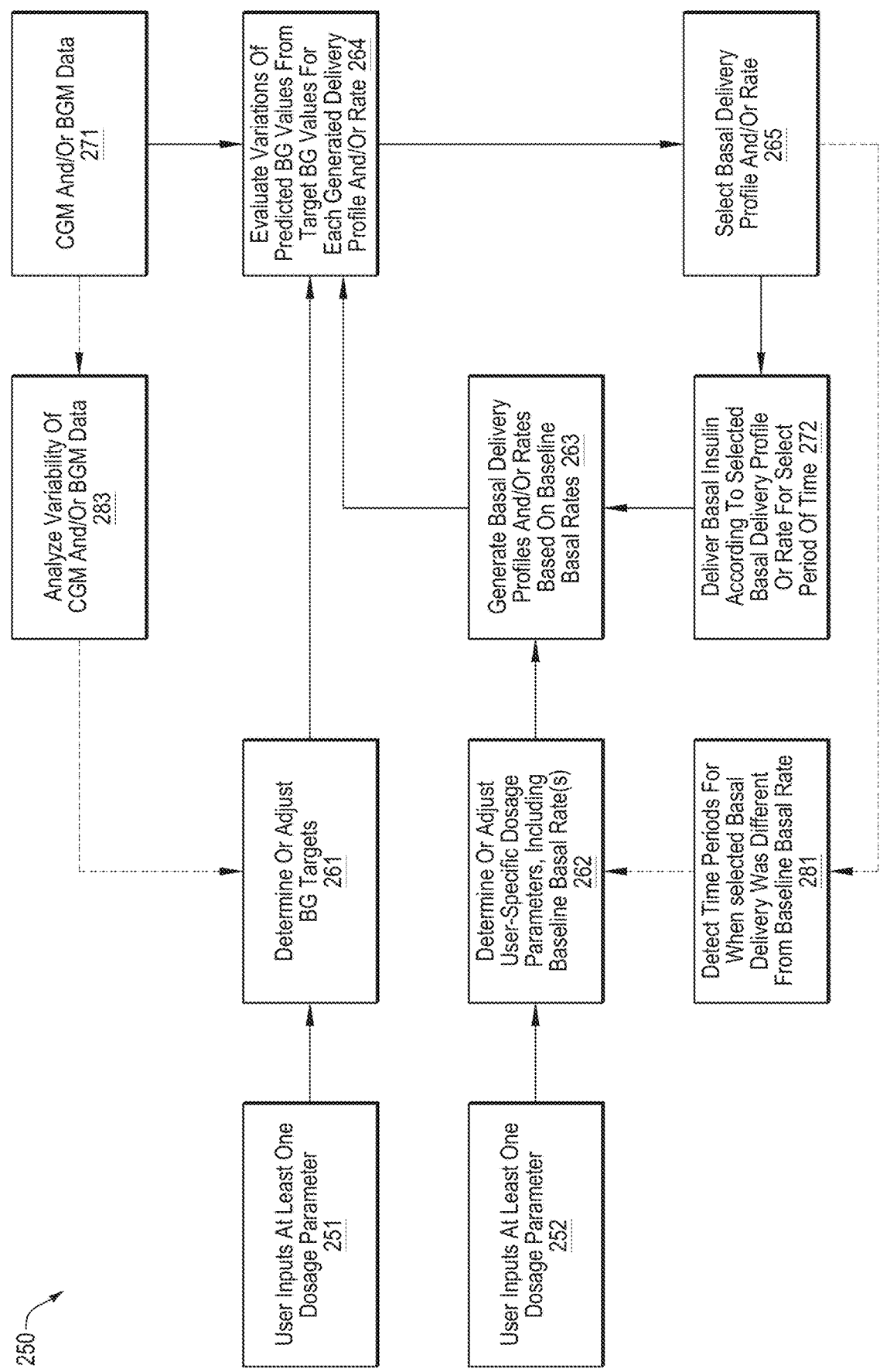
FIG. 11 is a flowchart of an example technique for adjusting basal insulin delivery rates.

FIG. 11 is a flowchart of an example technique for adjusting basal insulin delivery rates, in accordance with one or more embodiments of the present disclosure. FIG. 11 depicts an example method 250 for operation of a diabetes management system, such as system 10 depicted in FIG. 1. As shown in FIG. 11, a system can receive user inputs, such as user inputs at blocks 251 and 252, which can be used to provide initial settings, such as one or more target blood glucose values that may be used or determined at block 261 and/or one or more user-specific dosage parameters that may be used or determined at block 262. In some cases, user inputs at blocks 251 and 252 can be entered by a PWD, a caregiver for the PWD, or a healthcare professional. In some cases, user inputs at blocks 251 and 252 can be entered on a mobile computing device 60, such as a smartphone. Based on the user-specific dosage parameters, the method 250 can generate multiple basal insulin delivery profiles and/or rates at block 263. In some cases, the plurality of basal insulin delivery profiles and/or rates can be based upon one or more baseline basal rates. At block 264, the method 250 can analyze each basal delivery profile or rate generated at block 263 based on variations of predicted future blood glucose values from one or more target blood glucose values (such as the target blood glucose values from block 261) using blood glucose data from a continuous glucose monitor (CGM) or blood glucose meter (BGM), such as generated in block 271. In some cases, the blood glucose data can be from the continuous glucose monitor 50 from the system 10 of FIG. 1. As will be discussed below, predicted blood glucose values for each generated basal delivery profile or rate can use user-specific dosage parameters (for example, those determined or otherwise adjusted at block 262). Additionally, predicted blood glucose values can include inputs regarding previous dosages of insulin and/or food consumption (e.g., estimates of carbohydrates consumed). In some cases, predicted blood glucose values used at block 264 can consider data indicative of exercise, sickness, or any other physical state that might impact blood glucose levels in a PWD. Based on an analysis of a variation of predicted blood glucose levels performed at block 264, a basal delivery profile or rate generated at block 263 can be selected at block 265, and the system can deliver basal insulin according to that selected basal delivery profile or rate to the PWD for a select period of time at block 272. In some cases, the pump assembly 15 of system 10 of FIG. 1 can be used to deliver the insulin. In some cases, the blocks 263, 264, 265, and 272 can each be conducted by reusable pump controller 200 of system 10. In some cases, the blocks 271, 263, 264, and 265 can all be conducted by continuous glucose monitor 50 of system 10, with data regarding the selected delivery rate being sent to reusable pump controller 200. In some cases, the blocks 251, 252, 261, 262, 263, 264, and 265 can all be conducted on mobile computing device 60 of system 10 of FIG. 1, with data regarding the selected delivery rate being sent to reusable pump controller 200 from the mobile computing device 60.

Methods and systems provided herein can additionally update or adjust user-specific dosage parameters at block 262 and can update or adjust the blood glucose targets at block 261 based on the selected basal delivery profiles and/or rates selected at block 265 or based on blood glucose data obtained at block 271. In some cases, at block 281, periods of time when a selected basal delivery was different from baseline basal rate for that period of time can be detected. For these select periods of time (e.g., diurnal time segments), at block 262 the user-specific dosage parameters can be adjusted for that period of time. For example, if the selected basal delivery for a time block exceeds the baseline basal rate for that time block, at block 262 the system 10 can increase the baseline basal rate for that time block (e.g., a diurnal period) or some other related time block (such as the preceding diurnal period). For example, if the selected basal delivery from 2 PM to 3 PM exceeded the baseline basal rate for that time, the system 10 may increase the baseline basal rate for 2 PM to 3 PM or may adjust the baseline basal rate for 1 PM to 2 PM, 12 PM to 1 PM and/or 11 AM to 12 PM. In some cases, each adjustment to a baseline basal rate is less than the difference between the baseline basal rate and the selected basal delivery. In some cases, each adjustment can be a predetermined amount (e.g., baseline basal rate adjusted up or down by 0.5 units/hour, 0.3 units/hour, 0.1 units per hour) or percentage (e.g., 5%, 3%, 1%), which can limit the change to the user-specific dosage parameters due to an irregular event. At block 283, the variability of blood glucose data can be analyzed to make adjustments to the blood glucose target(s) at block 261. For example, at block 283, a blood glucose data distribution can be determined for a diurnal period (e.g., between 1 AM and 2 AM) to determine a measure of dispersion of blood glucose values for the PWD during that diurnal period, and at block 261 adjustments can be made to the blood glucose target for that diurnal period, and/or adjacent periods, based on the measure of dispersion.

Each of the processes discussed in regards to FIG. 11 are discussed at further length below.

In some cases, a diabetes management system may have a threshold beyond which it ceases personalizing BR, CSF, and/or CR for various diurnal time blocks. For example, if the system monitors variations in these therapeutic parameters and determines that no modification has been performed in a certain amount of time (e.g., one week, two weeks, a month, etc.), the system may stop monitoring for and performing daily updates, and may revert to a periodic check to verify that the therapeutic parameters are still at the optimal parameters for the PWD. In these and other cases, as the system shifts away from modifying the therapeutic parameters for the various diurnal time blocks, the system may provide a notification of how close the therapeutic parameters are for the PWD as compared to the general probability distribution for the therapeutic parameters. For example, in a manner similar to that described above with respect to determining the Mahalanobis Distance with respect to initial values, the system may perform a similar analysis and inform a user (such as the PWD or a caregiver of the PWD) of the score of the optimal therapeutic parameters for the PWD. In some cases, these optimal values and/or the associated score may be provided to a manufacturer of diabetes management systems to update and/or modify the general probability distributions.

Figure 12:
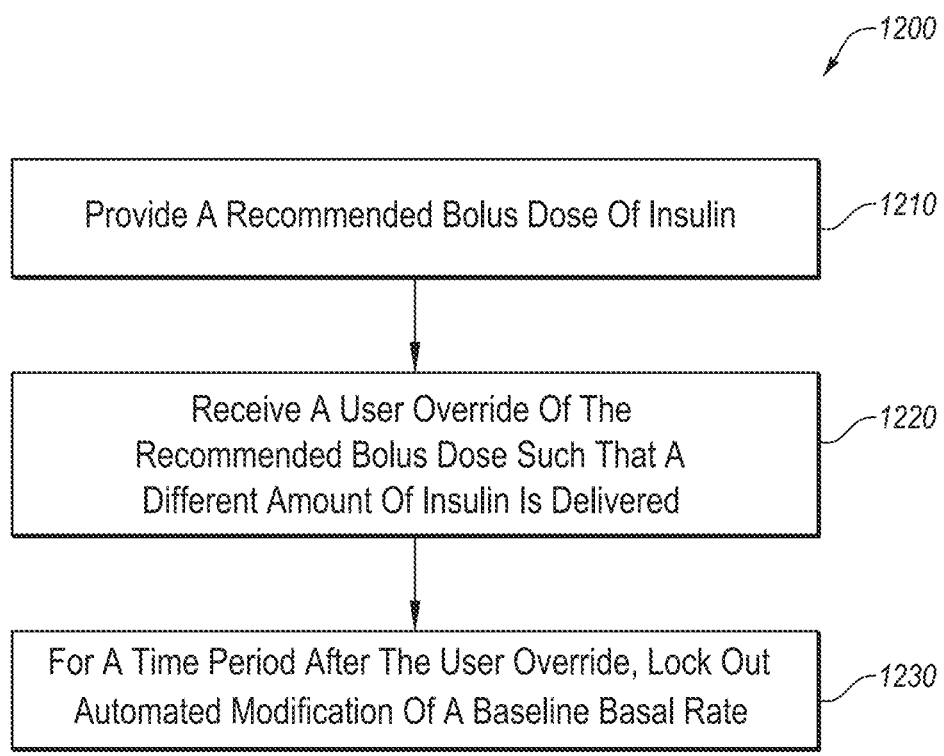
FIG. 12 is a flowchart of an example method of adjusting a basal insulin rate.

FIG. 12 illustrates a flowchart of an example method 1200 of adjusting a basal insulin rate. The method 1200 may be performed by any suitable system, apparatus, or device. For example, the system 10, the pump assembly 15, the mobile computing device 60 of FIG. 1, and/or a remote server may perform one or more of the operations associated with the method 1200. Although illustrated with discrete blocks, the steps and operations associated with one or more of the blocks of the method 1200 may be divided into additional blocks, combined into fewer blocks, or eliminated, depending on the desired implementation.

At block 1210, a recommended bolus dose of insulin for a PWD may be provided. For example, a user interface of a mobile electronic device or an insulin pump may display a recommended bolus dose based on a high blood glucose level or an input regarding an upcoming meal.

At block 1220, a user override of the recommended bolus dose may be received such that a different amount of insulin is delivered. For example, a user of an input device may adjust the recommended bolus dose to a larger dose such that more insulin than recommended is delivered to the PWD.

At block 1230, for a time period after the user override, the automated modification of a baseline basal rate may be locked out. For example, the lockout may prevent a diabetes management system from delivering a ratio of the baseline basal rate during one or more diurnal time periods. As another example, the lockout may prevent the system from considering blood glucose levels during one or more of the diurnal time blocks affected by the manually modified bolus dose in adjusting the baseline basal rate for future diurnal time blocks.

Modifications, additions, or omissions may be made to the method 1200 without departing from the scope of the present disclosure. For example, the operations of the method 1200 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 13:
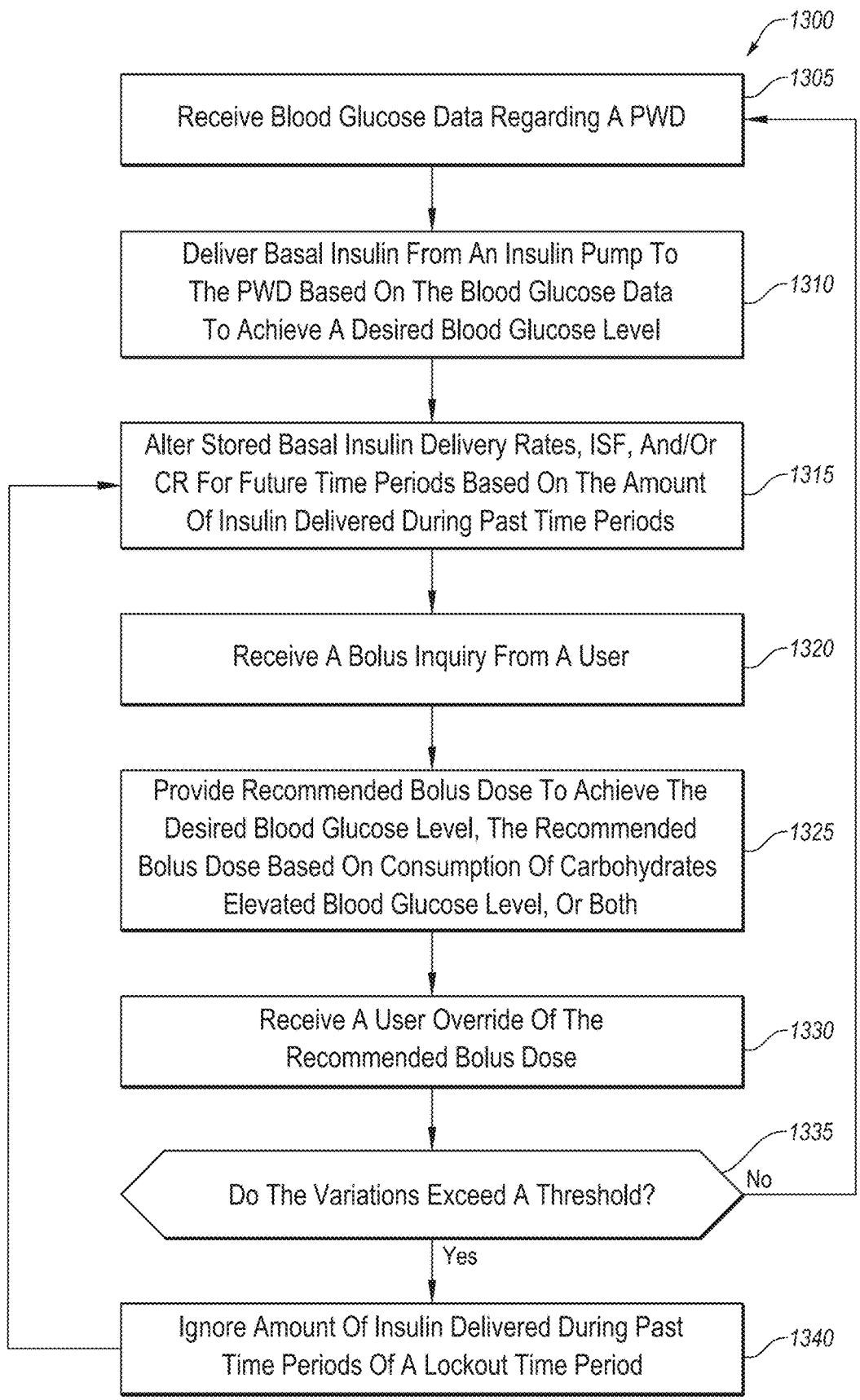
FIG. 13 is a flowchart of another example method of adjusting a basal insulin rate.

FIG. 13 illustrates a flowchart of an example method 1300 of adjusting a basal insulin rate. The method 1300 may be performed by any suitable system, apparatus, or device. For example, the system 10, the pump assembly 15, the mobile computing device 60 of FIG. 1, and/or a remote server may perform one or more of the operations associated with the method 1300. Although illustrated with discrete blocks, the steps and operations associated with one or more of the blocks of the method 1300 may be divided into additional blocks, combined into fewer blocks, or eliminated, depending on the desired implementation.

At block 1305, blood glucose data may be received regarding a PWD. For example, a CGM or a BGM may measure a blood glucose level and may provide that reading to a control device.

At block 1310, basal insulin may be delivered to the PWD from an insulin pump based on the blood glucose data to achieve a desired blood glucose level. For example, as described herein, the insulin pump may receive a message to deliver a ratio of a baseline basal rate of insulin based on the blood glucose data.

At block 1315, the stored basal insulin deliver rates, ISF, and/or CR for future time periods may be altered based on the amount of insulin delivered during past time periods. For example, as described herein, if a diabetes management system delivered 2× the baseline basal rate for a diurnal time period, the system may increase the baseline basal rate for that diurnal time period.

At block 1320, a bolus inquiry may be received from a user. For example, a PWD may interact with an electronic device to indicate that the PWD feels as though their blood sugar is high. As another example, a PWD may indicate that they are preparing to eat a meal and input the number of grams of carbohydrates that the PWD intends to eat at the meal.

At block 1325, a recommended bolus dose to achieve the desired blood glucose level may be provided. The recommended bolus dose may be based on consumption of carbohydrates, an elevated blood glucose level, or both. In some embodiments, the recommended bolus dose may be presented to a user of an electronic device.

At block 1330, a user override of the recommended bolus dose may be received from a user. For example, a user may manually adjust the bolus dose to be larger or smaller.

At block 1335, a determination may be made as to whether there has been a recent user override. If there have been no recent user overrides, the method 1300 may return to block 1305 to start over. If there has been a recent user override, the method 1300 may proceed to block 1340.

At block 1340, an amount of insulin delivered during past time periods may be ignored for a lockout time period. For example, in determining whether to deliver a ratio of a baseline basal rate to a PWD, a system may normally consider basal and/or bolus insulin delivered in determining what ratio of a baseline basal rate to deliver. However, after a lockout, such information may be ignored or given less weight. The method 1300 may then proceed to block 1315.

After returning to block 1315, the alteration of one or more of the therapeutic parameters may ignore the amount of insulin delivered per the block 1340. For example, the alteration may be based only on diurnal time blocks unaffected by the overridden bolus dose, and/or may default to only delivering the baseline basal rate rather than a ratio of the baseline base rate.

Modifications, additions, or omissions may be made to the method 1300 without departing from the scope of the present disclosure. For example, the operations of the method 1300 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 14:
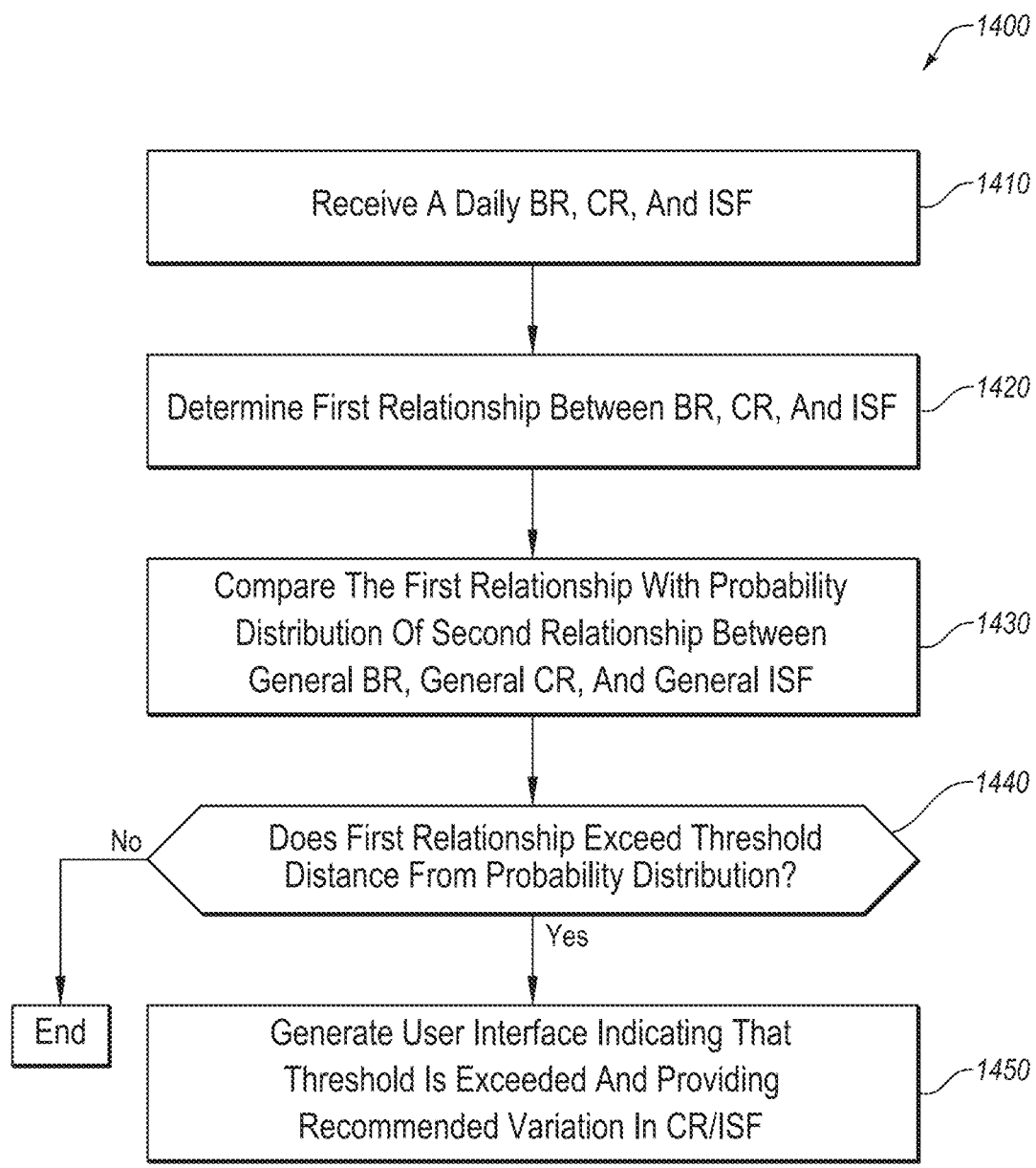
FIG. 14 is a flowchart of an example method of providing a recommendation of one or more therapeutic parameters.

FIG. 14 illustrates a flowchart of an example method 1400 of providing a recommendation of one or more therapeutic parameters. The method 1400 may be performed by any suitable system, apparatus, or device. For example, the system 10, the pump assembly 15, the mobile computing device 60 of FIG. 1, and/or a remote server may perform one or more of the operations associated with the method 1400. Although illustrated with discrete blocks, the steps and operations associated with one or more of the blocks of the method 1400 may be divided into additional blocks, combined into fewer blocks, or eliminated, depending on the desired implementation.

At block 1410, a daily BR, CR, and/or ISF may be received. For example, a user may manually input a BR, CR, and/or ISF for a PWD when beginning insulin treatment, or when setting up a new device or software feature associated with treating diabetes of the PWD. As another example, a user may manually modify an existing BR, CR, and/or ISF. In some cases, only one or two of the therapeutic parameters may be input and one or more other therapeutic parameters may be derived from mathematical relationships between the therapeutic parameters.

At block 1420, a first relationship between the BR, CR, and/or ISF may be determined. For example, the values may be input into a matrix, or may be grouped together as an initial set of therapeutic values. As another example, for a received BR, the corresponding CR and ISF may be plotted in a chart.

At block 1430, the first relationship may be compared with a probability distribution of a second relationship between the general BR, general CR, and general ISF. For example, in some embodiments, a plot of a slice of the probability distribution of the general CR and general ISF for the BR received at block 1410 may be provided and the first relationship may be plotted on the same figure. Additionally or alternatively, the first relationship may be numerically analyzed relative to the general probability distribution such as using a Mahalanobis Distance.

At block 1440, a determination may be made as to whether the distance between the first relationship and the probability distribution exceeds a threshold. If it is determined that the distance does not exceed the threshold, the method 1400 may finish. If it is determined that the distance does exceed a threshold, the method 1400 may proceed to block 1450.

At block 1450, a user interface may be generated indicating that the distance exceeds the threshold and providing a recommended variation in one or more of the therapeutic parameters. For example, a user interface (such as that illustrated in FIG. 6) may illustrate a chart of the location of the first relationship and a recommendation of variation to one or both of CR and ISF. For example, the recommended variation may move the first relationship closer to the probability distribution.

Modifications, additions, or omissions may be made to the method 1400 without departing from the scope of the present disclosure. For example, the operations of the method 1400 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 15:
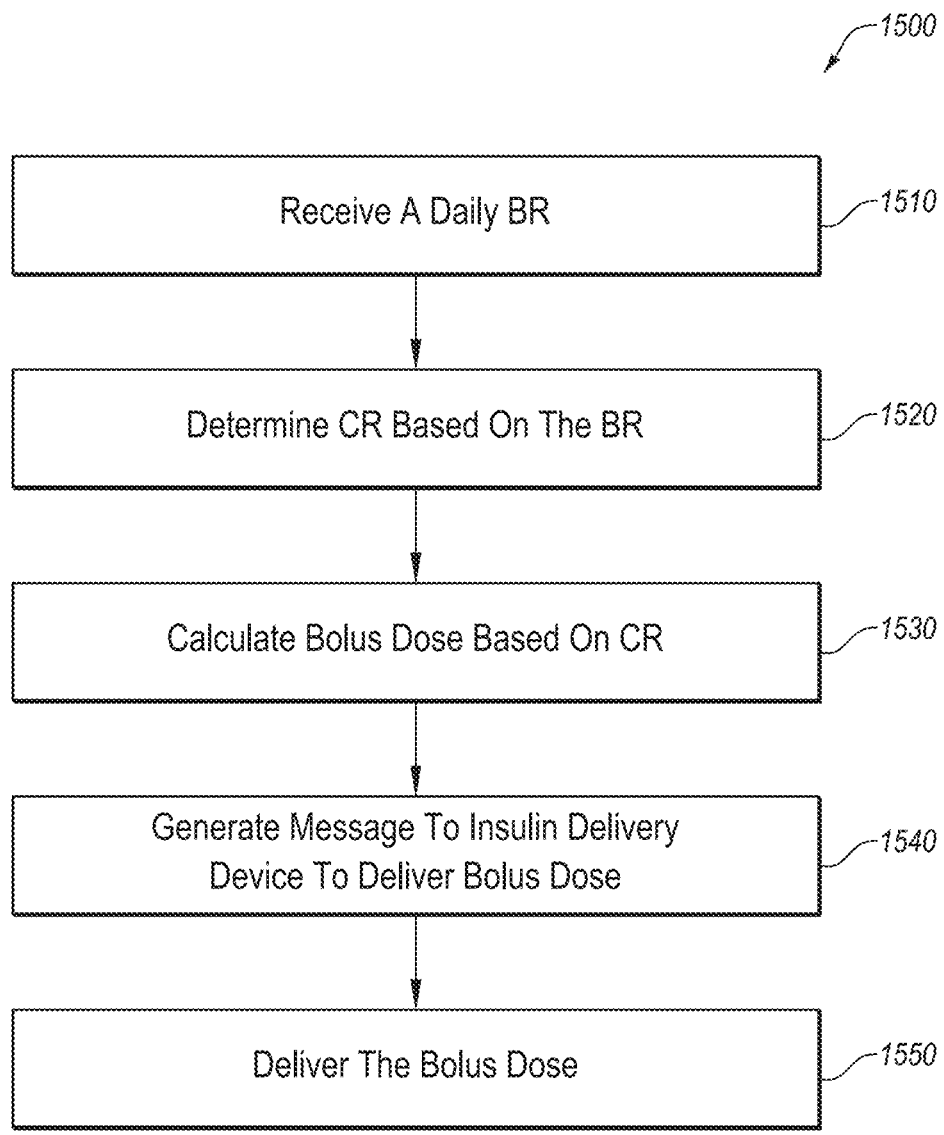
FIG. 15 is a flowchart of an example method of delivering insulin.

FIG. 15 illustrates a flowchart of an example method 1500 of delivering insulin. The method 1500 may be performed by any suitable system, apparatus, or device. For example, the system 10, the pump assembly 15, the mobile computing device 60 of FIG. 1, and/or a remote server may perform one or more of the operations associated with the method 1500. Although illustrated with discrete blocks, the steps and operations associated with one or more of the blocks of the method 1500 may be divided into additional blocks, combined into fewer blocks, or eliminated, depending on the desired implementation.

At block 1510, a daily BR may be received. For example, a user may input a BR for a PWD into an electronic device.

At block 1520, a CR may be determined based on the BR. For example, a diabetes management system may utilize a mathematical relationship to determine the CR from the BR. Such a relationship may include that expressed in Equation 2.

At block 1530, a bolus dose may be calculated based on the CR. For example, if a PWD is going to eat a meal and inputs an amount of carbohydrates to be consumed during the meal, the diabetes management system may use the CR determined at block 1520 to calculate the amount of bolus dose required.

At block 1540, a message may be generated for an insulin delivery device to deliver the bolus dose calculated at block

1530. Such a delivery device may include an insulin pump, or an injection based delivery mechanism such as a pen or syringe.

At block 1550, the bolus dose may be delivered by the insulin delivery device.

Modifications, additions, or omissions may be made to the method 1500 without departing from the scope of the present disclosure. For example, the operations of the method 1500 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 16:
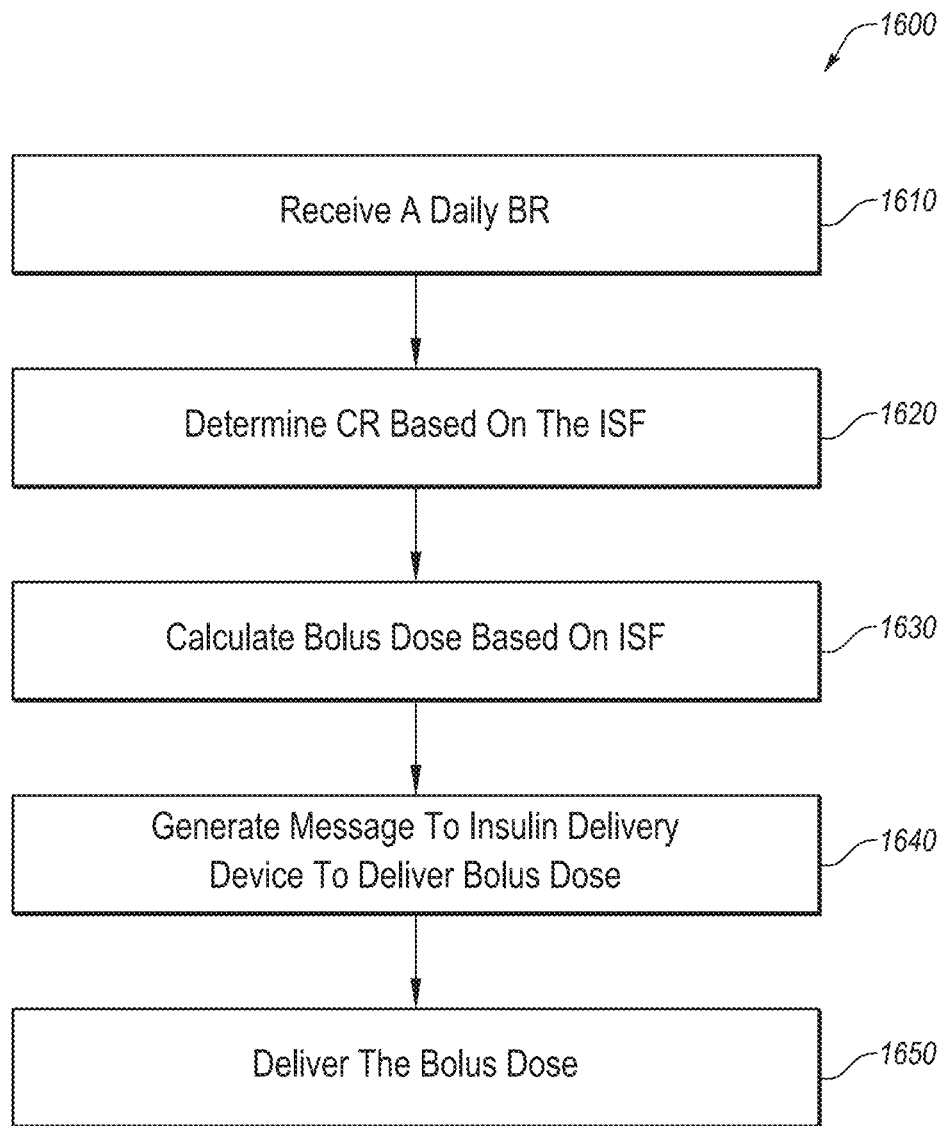
FIG. 16 is a flowchart of another example method of delivering insulin.

FIG. 16 illustrates a flowchart of an example method 1600 of delivering insulin. The method 1600 may be performed by any suitable system, apparatus, or device. For example, the system 10, the pump assembly 15, the mobile computing device 60 of FIG. 1, and/or a remote server may perform one or more of the operations associated with the method 1600. Although illustrated with discrete blocks, the steps and operations associated with one or more of the blocks of the method 1600 may be divided into additional blocks, combined into fewer blocks, or eliminated, depending on the desired implementation.

At block 1610, a daily BR may be received. For example, a user may input a BR for a PWD into an electronic device.

At block 1620, an ISF may be determined based on the BR. For example, a diabetes management system may utilize a mathematical relationship to determine the ISF from the BR. Such a relationship may include that expressed in Equation 1.

At block 1630, a bolus dose may be calculated based on the ISF. For example, if a PWD has a high blood glucose level, the diabetes management system may use the ISF determined at block 1620 to calculate the amount of bolus dose required.

At block 1640, a message may be generated for an insulin delivery device to deliver the bolus dose calculated at block 1630. Such a delivery device may include an insulin pump, or an injection based delivery mechanism such as a pen or syringe.

At block 1650, the bolus dose may be delivered by the insulin delivery device.

Modifications, additions, or omissions may be made to the method 1600 without departing from the scope of the present disclosure. For example, the operations of the method 1600 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 17:
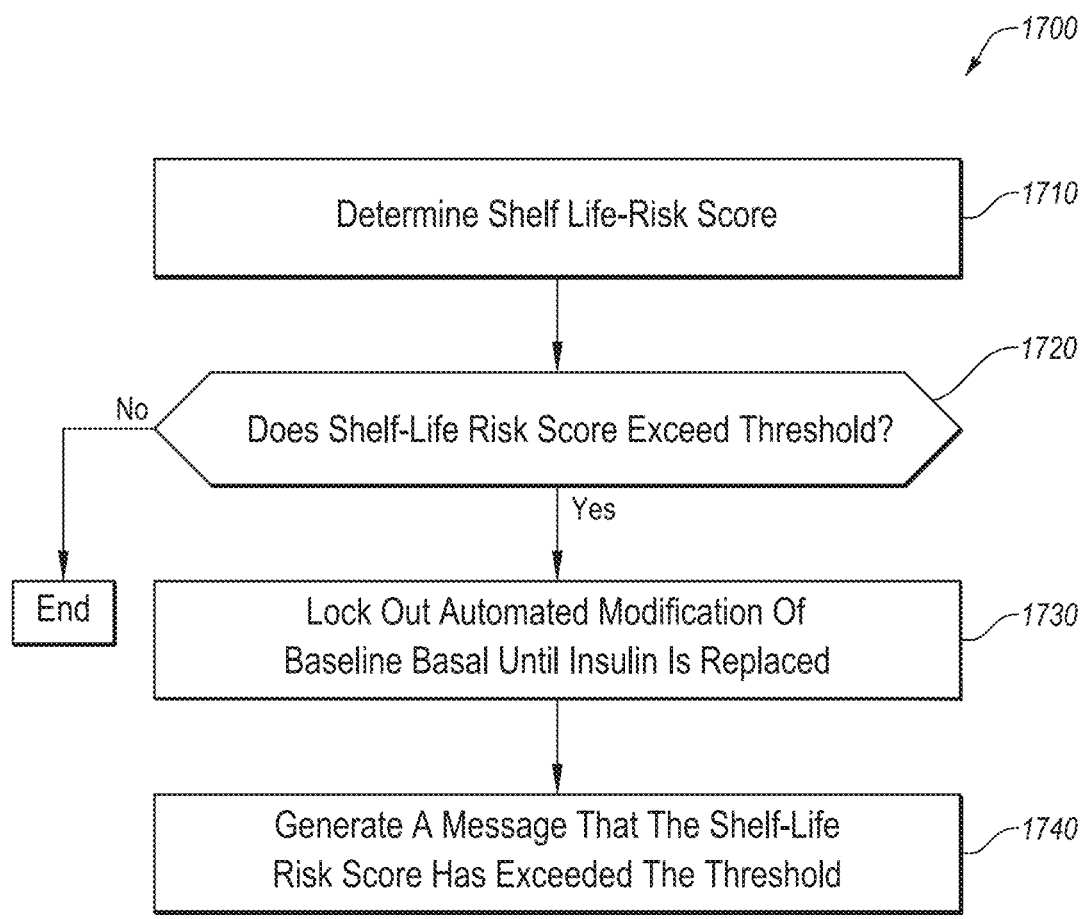
FIG. 17 is a flowchart of an example method of adjusting a basal insulin rate.

FIG. 17 illustrates a flowchart of an example method 1700 of adjusting a basal insulin rate. The method 1700 may be performed by any suitable system, apparatus, or device. For example, the system 10, the pump assembly 15, the mobile computing device 60 of FIG. 1, and/or a remote server may perform one or more of the operations associated with the method 1700. Although illustrated with discrete blocks, the steps and operations associated with one or more of the blocks of the method 1700 may be divided into additional blocks, combined into fewer blocks, or eliminated, depending on the desired implementation.

At block 1710, a shelf-life risk score may be determined. For example, a diabetes management system may track the age of an insulin cartridge associated with a pump and assign a certain shelf-life risk score based on the age of the insulin cartridge. As another example, the system may monitor the number of times the system has delivered an amount of insulin above the baseline basal rate. For example, if the system repeatedly delivers a ratio of 2× the baseline basal rate, the system may provide a shelf-life risk score based on how frequently the larger ratio is delivered. In some cases, the shelf-life risk score may be based on both age and number of times the larger dose is delivered.

At block 1720, a determination is made as to whether the shelf-life risk score exceeds a threshold. If it does not exceed a threshold, the method may end and the diabetes management system may proceed with normal operation. If it does exceed the threshold, the method 1700 may proceed to block 1730.

At block 1730, the automated modification of a baseline basal insulin rate may be locked out until the insulin is replaced. For example, similar to block 1230 of FIG. 12, the system may be prevented from modifying the baseline basal insulin rate for a certain period of time. In the method 1700, the period of time may be based on when the insulin is replaced. For example, if the threshold is crossed at a first diurnal time block and the insulin is replaced at a second diurnal time block later in time, the span of time between the first diurnal time block and the second diurnal time block may prevent lockout automated modification of the basal rate. Such lockout may prevent the system from delivering a ratio of the baseline basal rate and may default to delivering the baseline basal rate. Additionally or alternatively, such lockout may prevent the system from adjusting the baseline basal rate for the diurnal time block or a related diurnal time block in the future based on the amount of insulin delivered or the effectiveness of the delivered insulin during the time period when the shelf-life risk score threshold was exceeded.

At block 1740, a message may be generated that the shelf-life risk score has exceeded the threshold. For example, a message may be generated that the system may stop providing personalization until the insulin is replaced. As another example, the message may instruct a user to replace an insulin cartridge immediately with instructions of how to do so. As another example, the message may lockout certain interactive features of the system until the insulin has been replaced.

Modifications, additions, or omissions may be made to the method 1700 without departing from the scope of the present disclosure. For example, the operations of the method 1700 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 18:
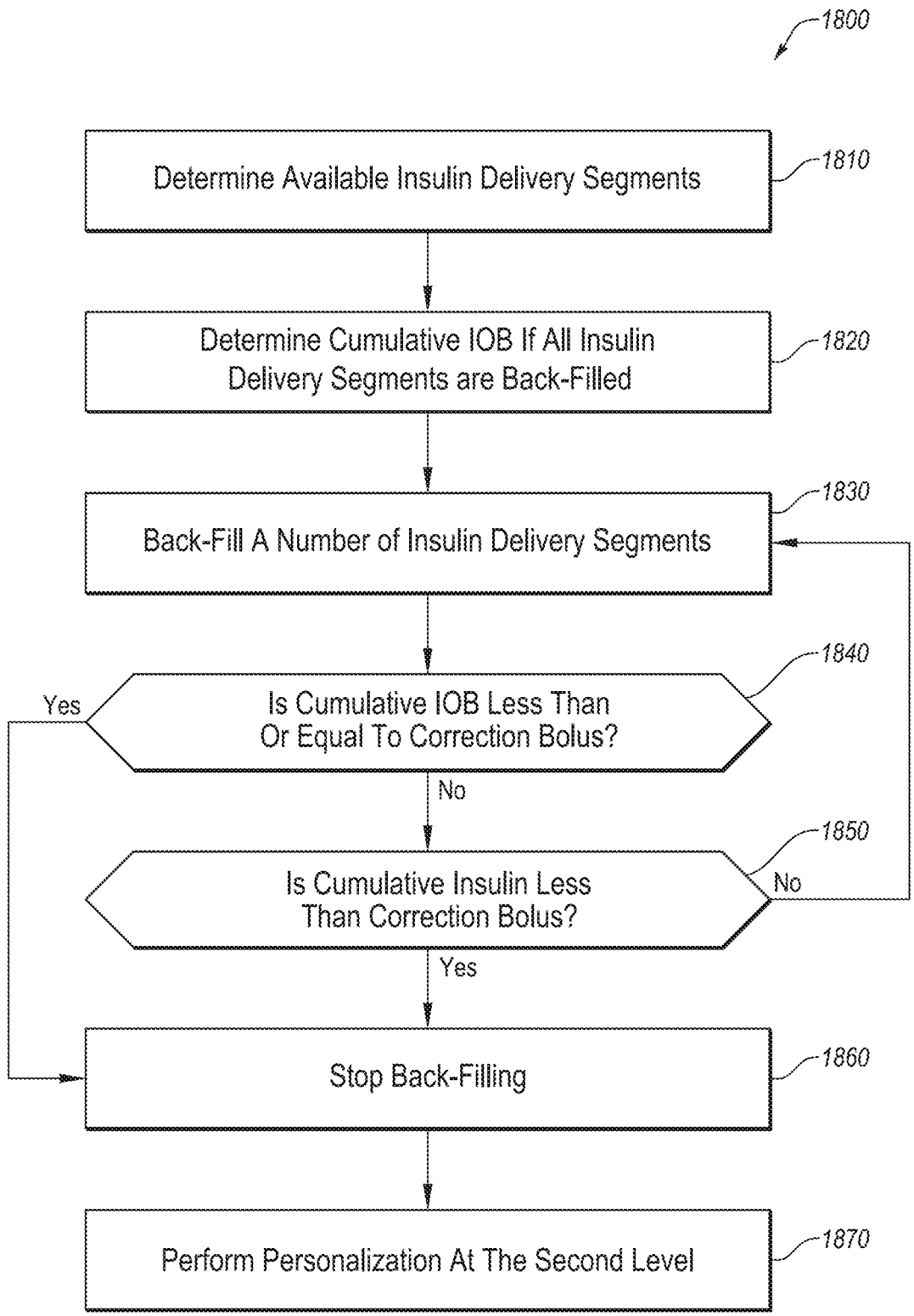
FIG. 18 is a flowchart of an example method of personalizing an insulin delivery rate based on a correction bolus.

FIG. 18 illustrates a flowchart of an example method 1800 of personalizing an insulin delivery rate based on a correction bolus. The method 1800 may be performed by any suitable system, apparatus, or device. For example, the system 10, the pump assembly 15, the mobile computing device 60 of FIG. 1, and/or a remote server may perform one or more of the operations associated with the method 1800.

For example, the mobile computing device 60 may operate as a control device. Although illustrated with discrete blocks, the steps and operations associated with one or more of the blocks of the method 1800 may be divided into additional blocks, combined into fewer blocks, or eliminated, depending on the desired implementation.

FIG. 18 may operate within the context of two layers of personalization. Personalization at a first level may occur as a user may be provided with insulin at a ratio or multiple of a baseline basal rate as described in herein. For example, based on a delivery profile, the user may be provided with 0×, 1×, or 2× of the baseline basal rate for each delivery action. Personalization at a second level may occur as a control device analyzes the delivery actions for a diurnal time period and adjusts one or more of the BR, CR, and ISF for a related diurnal time period based on the personalization that occurred at the first level, as described herein.

At block 1810, a determination may be made as to a number of available insulin delivery segments for a back-fill time. For example, a control device (such as the mobile computing device 60 of FIG. 1) may obtain an indication of a correction bolus, and may identify one or more delivery actions within the back-fill time relative to the correction bolus. For example, if the back-fill time is two hours, the control device may identify delivery actions within the two hours prior to the correction bolus where less than a maximum amount of allowed insulin was delivered based on personalization at the first level. For example, if two delivery actions delivered 1× insulin of a possible 2× delivery, both delivery actions would provide an available insulin delivery segment to increase to 2× delivery of insulin. In some embodiments, the block 1810 may be applied to available insulin delivery segments that may be back-filled to reduce the insulin delivered. For example, if two delivery actions delivered 1× insulin, both delivery actions would provide an available insulin delivery segment to be reduced to 0× insulin.

At block 1820, a determination may be made as to what the cumulative IOB would be if all available insulin delivery segments were back-filled. For example, with respect to increasing insulin delivery (such as when personalizing for a correction bolus), the control device may calculate the IOB if each delivery action delivered the maximum allowed ratio or multiple of the baseline basal insulin rate, such as 2×. As an additional example, with respect to decreasing insulin delivery (such as when personalizing for a negative correction bolus), the control device may calculate the reduction in IOB if each delivery action delivered the minimum allowed ratio or multiple of the baseline basal insulin rate, such as 0×.

At block 1830, one or more insulin delivery segments may be back-filled to adjust the historical delivery data. For example, the control device may back-fill all available segments, either to account for a correction bolus or a negative correction bolus. Additionally or alternatively, the method 1800 may iteratively return to the block 1830 such that the number of back-filled insulin delivery segments may be decreased or increased. In some embodiments, the number of insulin delivery segments back-filled may be adjusted one segment at a time, or may follow some other algorithm such as an optimization algorithm, a minimum-finding algorithm, a maximum-finding algorithm, or others.

At block 1840, a determination may be made as to whether the cumulative IOB is less than or equal to a correction bolus. For example, the cumulative IOB based on the number of insulin delivery segments back-filled at the block 1830 may be compared to a correction bolus delivered to a user, or requested to be delivered to a user. If the cumulative IOB is less than or equal to the correction bolus, the method 1800 may proceed to block 1860. If the cumulative IOB is greater than the correction bolus, the method 1800 may proceed to block 1850. In some embodiments, the inquiry may determine if the IOB reduction is less than or equal to a negative bolus.

At block 1850, a determination may be made as to whether the cumulative insulin of the back-filled insulin delivery segments is less than the correction bolus. For example, the control device may determine the cumulative amount of insulin from the number of back-filled insulin delivery segments back-filled at the block 1830. If the cumulative insulin that was back-filled is less than the correction bolus, the method 1800 may proceed to the block 1860. If the cumulative insulin that was back-filled is not less than the correction bolus, the method 1800 may return to the block 1830 to adjust the number of insulin delivery segments that are back-filled. In some embodiments, the inquiry may determine if the reduction in insulin is less than the negative bolus.

At block 1860, the back-filling process may be stopped. For example, the control device may cease adjusting the number of back-filled insulin delivery segments and may make the delivery actions adjusted by the back-filled insulin delivery segments the historical information regarding insulin delivery for the respective time segments.

At block 1870, personalization may be performed at the second level. For example, the control device may utilize the historical information regarding insulin delivery as adjusted using the back-filled insulin delivery segments to adjust one or more of the BR, CR, and ISF of a user for a diurnal time block related to the diurnal time block that includes the time segments with back-filled insulin delivery segments.

Modifications, additions, or omissions may be made to the method 1800 without departing from the scope of the present disclosure. For example, the operations of the method 1800 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

In some embodiments, the method 1800 may be modified as described to account for a negative bolus rather than a correction bolus. Additionally, the method 1800 has been described with a perspective of back-filling all available segments and then decreasing the number of back-filled segments until the cumulative IOB or the cumulative insulin is less than the correction bolus. In some embodiments, the perspective may be shifted such that additional insulin delivery segments may be back-filled until the cumulative IOB or the cumulative insulin is greater than the correction bolus.

In some embodiments, the method 1800 may be modified such that one or more of the blocks 1840-1860 are omitted and the number of insulin delivery segments of the block 1830 may be limited by the back-fill time. Additionally or alternatively, the method 1800 may be modified such that no back-fill time may be used as a constraint and the constraints on the number of insulin delivery segments that may be back-filled are based on the cumulative IOB and/or the cumulative insulin relative to the correction bolus.

The following description relates, generally, to medicine delivery systems and methods. Such systems and methods may be used and performed, respectively, by a user, for example, a person with diabetes (PWD). The PWD may live with type 1, type 2, or gestational diabetes. In some cases, a user can be a healthcare professional or caregiver for a PWD. In some embodiments, the systems and methods may be used to personalize insulin delivery to a PWD.

The drawings in FIGS. 19 through 24 may use reference labels that include the same reference numbers (e.g., "400," "900," etc.) or a similar range of reference numbers as other drawings. For clarity, an "X-" may be used herein to denote that a reference label relates to FIGS. 19 through 24, and not another figure that uses a similar reference number, for example, "X-400" or "X-970."

Methods and systems provided herein can use information from a glucose measurement device (e.g., a continuous glucose monitor) to have up-to-date blood glucose data (e.g., a plurality of blood glucose data points each hour) for the PWD in order to determine how to adjust basal insulin delivery rates. In some cases, methods and systems provided herein can use blood glucose data from both one or more continuous glucose monitors and one or more blood glucose meters. Methods and systems provided herein can be part of a hybrid closed-loop system (for example, where basal rates can be adjusted automatically and the PWD can manually enter or deliver a bolus). In some cases, methods and system provided herein can be part of a fully closed-loop system (for example, where basal rates can be adjusted automatically and boluses can be delivered automatically). In some cases, "up-to-date" may mean less than 1 hour old, less than 30 minutes old, or less than 15 minutes old.

Methods and systems provided herein can use a model to predict multiple future blood glucose levels for multiple different basal insulin delivery profiles or basal insulin delivery rates, and select one of the basal insulin delivery profiles or basal insulin delivery rates based on prediction of which profile or rate will approximate a target blood glucose level, or more specifically, select the profile that minimizes the differences between the predicted future blood glucose values and one or more target blood glucose values. In some cases, the profile that minimizes, lessons, or lowers variations from one or more target blood glucose levels in the future may be selected. The selected basal profile can then be delivered to the PWD at least until a process of evaluating different basal insulin delivery profiles or rates is repeated. In some cases, methods and systems provided herein can repeat a process of evaluating multiple different basal insulin delivery profiles or basal insulin delivery rates at a time interval that is less than the time interval for the plurality of future predicted blood glucose values. For example, in some cases, the time interval between evaluating and selecting from multiple different basal insulin delivery profiles or basal insulin delivery rates can be less than one hour while the plurality of future predicted blood glucose values can extend over a time interval of at least two hours into the future. In some cases of methods and systems provided herein, each of the evaluated basal insulin delivery profiles or rates can extend for a time interval greater than the time interval between evaluation processes. In some cases, methods and systems provided herein can evaluate insulin delivery profiles and rates that extend at least two hours into the future and predicted blood glucose values can also be predicted over a time interval that extends at least two hours into the future. In some cases, the profiles/rates and time interval of predicted future blood glucose values extends at least three hours into the future. In some cases, the profiles/rates and time interval of predicted future blood glucose values extends a period of time (e.g., at least four hours) into the future. In some cases, the profiles/rates and time interval of predicted future blood glucose values extends at least five hours into the future. As used herein, the term blood glucose level may include any measurement that estimates or correlates with blood glucose level, such as a detection of glucose levels in interstitial fluids, urine, or other bodily fluids or tissues.

The different basal insulin delivery profiles or rates for each evaluation process can be generated using any suitable techniques. In some cases, multiple profiles or delivery rates are generated using one or more user-specific dosage parameters. In some cases, one or more user-specific dosage parameters can be entered by a user, calculated by information entered by a user, and/or calculated by monitoring data generated from the PWD (e.g., monitoring insulin delivery rates and blood glucose data while the PWD is using a pump in an open loop mode). In some cases, methods and systems provided herein can modify user-specific dosage parameters over time based on one or more selected basal insulin delivery profiles or rates and/or other data obtained from the PWD. In some cases, the user-specific dosage parameters can be dosage parameters that are commonly used in the treatment of diabetes, such as average total daily insulin, total daily basal (TDB) insulin, average basal rate, insulin sensitivity factor (ISF), and carbohydrate-to-insulin ratio (CR). For example, in some cases, a PWD's average basal rate can be used to calculate multiple different basal insulin delivery profiles based on multiples or fractions of the average basal rate used over different intervals of time. In some cases, methods and systems provided herein can use time-interval-specific user-specific dosage parameters (e.g., a time-interval-specific baseline basal rate). In some cases, methods and systems provided herein can make adjustments to time-interval-specific user-specific dosage parameters for each time interval for where a delivered basal rate varies from a baseline basal rate for that time interval. In some cases, user-specific dosage parameters are specific for time intervals of two hours or less, one hour or less, thirty minutes or less, or fifteen minutes or less. For example, in some cases methods and systems provided herein can store a baseline basal rate for the hour between 1 PM and 2 PM, and can adjust the baseline basal rate for that hour up if the method or system delivers more basal insulin during that time period and adjust the baseline basal rate down if the method or system delivers less basal insulin during that time period. In some cases, adjustments to user-specific dosage parameters can be based on a threshold variation and/or can be limited to prevent excessive adjustments to user-specific dosage parameters. For example, in some cases, a daily adjustment to a user-specific dosage parameter can be limited to less than 10%, less than 5%, less than 3%, less than 2%, or to about 1%. In some cases, an adjustment to a baseline basal rate is less than a difference between the amount of basal insulin actually delivered and the baseline basal for a specific period of time (e.g., if a baseline basal rate is 1 U/hour and systems or methods provided herein actually delivered 2 U for the previous hour, the adjustment to any baseline basal rate based on that difference would be less than 1 U/hour).

Methods and systems provided herein can use any appropriate model to predict multiple future blood glucose values. In some cases, predictive models can use one or more current or recent blood glucose measurements (e.g., from blood glucose meter and/or a continuous glucose monitor), estimates of rates of change of blood glucose levels, an estimation of unacted carbohydrates, and/or an estimation of unacted insulin. In some cases, predictive models can use one or more user-specific dosage parameters in predicting multiple blood glucose values over a future time interval for multiple different basal insulin delivery profiles or rates over that same future time interval. As discussed above, that future time interval can be at least two hours, at least three hours, or at least four hours, at least five hours, etc. User-specific dosage parameters, which can be time-interval-specific, can also be used in determining an estimation of unacted carbohydrates and/or an estimation of unacted insulin. In some cases, an estimation of unacted carbohydrates and/or an estimation of unacted insulin can use a simple decay function. In some cases, an estimate of unacted insulin can be determined using an Insulin On Board (IOB) calculation, which are common in the art of treating diabetes. In some cases, an IOB calculation used in a predictive model used in methods and systems provided herein can consider insulin delivered to the PWD during the delivery of a bolus. In some cases, the IOB calculation can additionally add or subtract to the IOB based on changes to the basal insulin delivery rate from a baseline basal rate. In some cases, an estimate of unacted carbohydrates can be determined using a Carbohydrates On Board (COB) calculation, which can be based on a decay function and announced meals. In some cases, predictive models used in methods and systems provided herein can also consider the non-carbohydrate components of a meal. In some cases, methods and systems provided herein can infer an amount of carbohydrates from an unannounced meal due to a spike in up-to-date blood glucose data. In some cases, predictive models used in methods and systems provided herein can additionally consider additional health data or inputs, which may indicate that the PWD is sick, exercising, experiencing menses, or some other condition that may alter the PWD's reaction to insulin and/or carbohydrates. In some cases, at least an IOB, a COB, an insulin sensitivity factor (ISF), and a carbohydrate-to-insulin ratio (CR) are used to predict future blood glucose values for each evaluated basal insulin delivery profile or rate.

Methods and systems provided herein can set one or more blood glucose targets using any suitable technique. In some cases, a blood glucose target can be fixed, either by a user or preprogrammed into the system. In some cases, the target blood glucose level can be time interval specific (e.g., based on diurnal time segments). In some cases, a user can temporarily or permanently adjust the target blood glucose level. In some cases, methods and systems provided herein can analyze the variability of blood glucose data for specific days of the week and/or based on other physiological patterns and adjust the blood glucose targets for that individual based on the specific day of the week or based on other physiological patterns. For example, a PWD may have certain days of the week when they exercise and/or PWD may have different insulin needs based on a menses cycle.

Methods and systems provided herein can evaluate each basal insulin delivery profile or rate to select the profile or rate that minimizes a variation from the one or more blood glucose targets using any appropriate method. In some cases, methods and systems provided herein can use a cost function to evaluate differences between the predicted blood glucose values for each basal insulin delivery profile or rate and blood glucose targets, potentially specified for a diurnal time segment. Methods and systems provided herein can then select a basal profile or rate that produces the lowest cost function value. Methods and systems provided herein can use any suitable cost function. In some cases, cost functions can sum the absolute value of the difference between each predicted blood glucose value and each blood glucose target. In some cases, cost functions used in methods and systems provided herein can use square of the difference. In some cases, cost functions used in methods and systems provided herein can assign a higher cost to blood glucose values below the blood glucose target in order reduce the risk of a hypoglycemic event. In some cases, the cost function can include a summation of the absolute values of a plurality of predicted deviations, squared deviations, log squared deviations, or a combination thereof. In some cases, a cost function can include variables unrelated to the predicted blood glucose values. For example, a cost function can include a penalty for profiles that do not deliver 100% of the BBR, thus adding a slight preference to use 100% of BBR. In some cases, methods and systems provided herein can include a cost function that provides a slight preference to keep the existing basal modification for every other interval (e.g., a second 15 minute segment), which could reduce the variability in basal insulin delivery rates in typical situations, but allow for more critical adjustments.

Methods and systems provided herein can receive various inputs from a user related to the delivery of basal insulin. In some cases, a user may input a fear of hypoglycemia (FHI) index. The FHI may indicate the preference for or reticence to experience certain blood glucose levels by the PWD. For example, the FHI may indicate that the PWD prefers "high" blood glucose levels (e.g., blood glucose levels above a threshold); or as another example, the FHI may indicate that the PWD is concerned about "going low" (e.g., blood glucose levels below a threshold). In some cases, the FHI may correspond to a threshold and an acceptable probability of crossing the threshold, including using the threshold to signify going high or using the threshold to signify going low, or both. In some cases, a probability of the PWD crossing the threshold may be determined and a baseline basal insulin rate may be modified to more closely align the acceptable probability of crossing the threshold with the actual probability of crossing the threshold. Additionally or alternatively, the FHI may be used in other ways in methods and systems of the present disclosure. For example, modification of the baseline basal insulin rate for a diurnal period may be modified one way for a high FHI and another way for a low FHI. As another example, multiple profiles of insulin delivery steps may use one set of possible steps for a high FHI, and another set of possible steps for a low FHI.

Methods and systems provided herein can modify or alter an insulin delivery profile or rate in any number of ways. In some cases, a user may select a temporary override to indicate a user preference for a particular blood glucose level. For example, the PWD may indicate that they are going for a long drive and do not want to have their blood glucose levels drop below a certain level, and so may designate a target blood glucose level higher than their normal target blood glucose level, which may be set for a particular or indefinite length of time. In some cases, methods and systems provided herein may modify or otherwise select a new profile or rate from multiple profiles that corresponds to the blood glucose level from the temporary override. In some cases, methods and systems provided herein can permit a user to merely indicate a reduced tolerance for the risk of going low and can determine a temporary blood glucose level based on the variability of blood glucose data for that PWD for previous days (optionally for a particular diurnal time segment).

Methods and systems provided herein can store a plurality of user-specific dosage parameters (e.g., BBR, CR, and ISF) as different values for a plurality of different diurnal time segments. As used herein, "diurnal time segments" periods of time during each day, such that the methods and systems will repeat use of each diurnal-specific user-specific dosage parameter during the same time on subsequent days if a stored diurnal-specific user-specific dosage parameter is not modified or change, thus the use of the stored diurnal-specific user-specific dosage parameter will wrap each day. Methods and systems provided herein, however, can be adapted to make daily (or more or less frequent) adjustments to each diurnal-specific user-specific dosage parameter based on the operation of the system. Methods and systems provided herein may additionally store settings or adjustments for specific days of the week or for other repeating cycles.

After a basal insulin delivery profile or rate is selected, methods and systems provided herein can include the delivery of basal insulin to the PWD according to the selected basal insulin profile or rate for any suitable period of time. In some cases, methods and systems provided herein may supply basal insulin according to the selected basal insulin delivery profile or rate for a predetermined amount of time that may be less than the time interval of the evaluated basal insulin delivery profiles or rates. For example, methods and systems provided herein may analyze projected blood glucose values for basal insulin delivery profiles or rates that last over the next four hours but repeat the process of selecting a new basal insulin delivery profile or rate every fifteen minutes. In some cases, methods and systems provided herein can delay or suspend basal insulin delivery during the delivery of a bolus, which can be triggered by a user requesting a bolus.

As used herein, "basal insulin delivery" has its normal and customary meaning within the art of the treatment of diabetes. Although basal rates are expressed as a continuous supply of insulin over time, basal insulin delivery may constitute multiple discrete deliveries of insulin at regular or irregular intervals. In some cases, methods and systems provided herein may only be able to deliver insulin in discrete fractions of a unit. For example, some insulin delivery devices can only deliver insulin in a dose that are an integer multiple of 0.05 units or 0.1 units. In some cases, a delivery of basal insulin can include a delivery of insulin at predetermined time intervals less than or equal to fifteen minutes apart or less, ten minutes apart or less, or five minutes apart or less. In some cases, the time interval between discrete basal insulin deliveries can be determined based on the basal insulin delivery rate (e.g., a basal rate of 1.0 units/hour might result in the delivery of 0.1 units every six minutes). As used herein, the term "bolus" has its normal and customary meaning with the art of the treatment of diabetes, and can refer to a bolus delivered in order to counteract a meal (i.e., a meal-time bolus) and/or to correct for elevated blood glucose levels (i.e., a correction bolus).

Methods and systems provided herein can in some cases include multiple delivery modes. In some cases, methods and systems provided herein can monitor the presence of blood glucose using one or more blood glucose measuring devices or methods, control or monitor the dispensation of medicine, and determine and/or update the user-specific dosage parameters regardless of the operating mode. For example, possible operating modes could include closed-loop or hybrid closed-loop modes that automatically adjust basal rates based on continuous glucose monitoring data (CGM) and other user-specific dosage parameters (e.g., baseline basal rate (BBR), insulin sensitivity factor (ISF), and carbohydrate-to-insulin ratio (CR)), modes that can use blood glucose monitor (BGM) data to update user-specific dosage parameters (e.g., BBRs, ISFs, and CRs) for different time blocks over longer periods of time, manual modes that require a patient to manually control the therapy program using an insulin pump, and advisory modes that recommend dosages for a PWD to inject using an insulin pen or syringe. By determining optimized control parameters that work across delivery modes, systems and methods provided herein can provide superior analyte control even when a PWD switches to a different delivery mode. For example, methods and systems provided herein may be forced to switch away from a hybrid closed-loop delivery mode that adjusts basal insulin delivery away from a BBR if a continuous glucose monitor malfunctions or the system otherwise loses access to continuous data. In some cases, data can be collected when the system is in an advisory or manual mode to optimize control parameters in preparation for a PWD to switch to a hybrid closed-loop system (e.g., in preparation for a PWD to start use of a continuous glucose monitor (CGM) and/or an insulin pump).

Methods and systems provided herein can include an insulin pump and at least one blood glucose measurement device in communication with the insulin pump. In some cases, the blood glucose measurement device can be a CGM adapted to provide blood glucose measurements at least every fifteen minutes. In some cases, methods and systems provided herein include a CGM adapted to provide blood glucose measurements at least every ten minutes. In some cases, methods and systems provided herein include a CGM adapted to provide blood glucose measurements every five minutes. Methods and Systems provided herein additionally include a controller adapted to determine an amount of basal insulin for delivery to a PWD and memory to store multiple user-specific dosage parameters. In some cases, the controller can be part of an insulin pump. In some cases, a controller can be part of a remote device, which can communicate wirelessly with an insulin pump. In some cases, the controller can communicate wirelessly with a CGM. In some cases, methods and systems provided herein can additionally include a user interface for displaying data and/or receiving user commands, which can be included on any component of a system provided herein. In some cases, the user interface can be part of smartphone. In some cases, a user can input information on the user interface to trigger methods and systems provided herein to deliver a bolus of insulin. In some cases, methods and systems provided herein can use a blood glucose meter adapted to use test strip as a blood glucose measurement device. In some cases, methods and systems provided herein can additionally include an insulin pen, which can optionally communicate wirelessly with a controller.

Setting Initial User-Specific Dosage Parameters

Systems and methods provided herein can use multiple user-specific dosage parameters for a PWD in order to determine rates of basal insulin delivery and optionally amounts of bolus insulin delivery. In some cases, initial user-specific dosage parameters can be set by a healthcare professional. In some cases, data entered by a user (e.g., the PWD, the PWD's caregiver, or a health care professional) can be used to estimate one or more user-specific dosage parameters. For example, FIG. 11 depicts a method where a user enters at least one dosage parameter at block 252.

In some cases, multiple user-specific dosage parameters can be set for multiple diurnal time segments. In some cases, different user-specific dosage parameters can have diurnal time segments of the same length of time or different lengths of time. In some cases, an initial setting for each user-specific dosage parameter can be set at the same value for each diurnal time segment, but the user-specific dosage parameter for each diurnal time segment can be independently adjusted in the methods and systems provided herein. In some cases, users (e.g., health care professionals) can input different user-specific dosage parameter values for different diurnal time segments.

Methods and systems provided herein can, in some cases, use user-specific dosage parameters that are commonly used in the treatment of diabetes. For example, methods and systems provided herein can ask a user to input one or more of an average Total Daily Dose (TDD) of insulin, a total daily basal (TDB) dose of insulin, an average basal rate (ABR) (which can be used as an initial baseline basal rate (BBR) in methods and systems provided herein), an insulin sensitivity factor (ISF), and/or a carbohydrate-to-insulin ratio (CR). In some cases, methods and systems provided herein can ask for a weight, age, or combination thereof of a PWD to estimate one or more user-specific dosage parameters. In some cases, methods and systems will store a BBR, an ISF, and a CR, which can each be set for multiple different time blocks over a repeating period of time (e.g., fifteen, thirty, sixty, or one hundred and twenty minute diurnal periods). As will be discussed in further detail below, methods and systems provided herein can adjust user-specific dosage parameters for each of the diurnal periods in order to personalize the delivery of insulin for the PWD in order to minimize risks for the PWD.

Methods and systems provided herein can ask for or permit a user to input a variety of different user-specific dosage parameters or dosage proxies to determine values for the initial settings of one or more user-specific dosage parameters and/or blood glucose targets. In some cases, the inputs can be limited to a Total Daily Basal (TDB) amount of insulin and a Fear of Hypoglycemia Index (FHI). In some cases, the inputs can be limited to a Total Daily Dose (TDD) amount of insulin and a FHI. In some cases, the TDB or TDD can be used determine the initial baseline basal rate (BBR), the initial carbohydrate-to-insulin ratio (CR), and the initial insulin sensitivity factor (ISF) based on mathematical relationships among and between for BBR, CR, ISF, TDB, and TDD. In some cases, a user can also set an initial ISF and CR. In some cases, a user (e.g., a health care professional) can optionally input any combination of BBR, CR, ISF, TDB, and TDD, and at least the initial BBR, initial CR, and initial ISF can be based on the values entered. For example, in some cases, a relationship between initial TDB, TDD, BBR, CR, and ISF can be expressed as follows: TDD [u/day]=2×TDB [u/day]=1800/ISF [mg/dL/u or [mmol/u]=400/CR [g/u]=48 hours/day×BBR [u/hour]. In some cases, the mathematical equation used to estimate ISF, CR, and BBR can use non-linear relationships between BBR, ISF, and CR.

Methods and systems provided herein can also make adjustments to user-entered user-specific dosage parameters prior to initial use. In some cases, methods and systems provided herein adjust user entered initial BBR, CR, and/or ISF values based on mathematical relationships among and between the initial BBR, CR, and ISF values. In some cases, if an entered ISF and an entered CR are outside of a predefined relationship between BBR, CR, and ISF, methods and systems provided herein will calculate a CR and an ISF that meets a predetermined relationship between BBR, CR, and ISF while minimizing a total change from the entered values for ISF and CR. In some cases, the predetermined relationship permits a range of CR values for each ISF value, permits a range of ISF values for each CR value, and permits a range of ISF and CR values for each BBR value. In some cases, the predetermined relationship represents a confidence interval for empirical data regarding relationships between basal rates, ISF, and CR values for a population of PWDs. In some cases, if an entered ISF, BBR, and/or CR are outside of a predefined relationship between BBR, CR, and ISF, methods and systems of the present disclosure may notify the user of the deviation from the predefined relationship. Additionally or alternatively, a healthcare provider override may be required to include ISF, BBR, and/or CR values outside of the predefined relationship as the initial user-specific dosage parameters.

Setting Initial Blood Glucose Targets

Initial blood glucose targets can be set or determined using any suitable technique. In some cases, blood glucose targets can be preprogrammed on memory within a system or device provided herein. In some cases, there can be a single blood glucose target preprogrammed into the system that does not change. In some cases, the diurnal time segments can each have a preprogrammed blood glucose target. In some cases, a user can program one or more blood glucose targets, which can be set differently for different periods of time. In some cases, a user can program the typical sleeping schedule, exercise schedule, and/or meal schedule for a PWD, and methods and systems provided herein can select lower blood glucose targets for sleep times and higher blood glucose targets around meal times and/or exercise times. In some cases, historical continuous glucose monitor data for the PWD prior to the PWD using the system can be used to set initial blood glucose targets (either for specific diurnal periods or for an entire day). In some cases, methods provided herein can have a PWD wear a CGM for a preliminary period of time (e.g., at least twenty-four hours, at least forty-eight hours, at least five days, or at least ten days) prior to allowing the methods and systems provided herein from delivering insulin at rates other than the BBR to detect blood glucose variability data for the PWD to set one or more initial blood glucose targets.

In some cases, such as shown in FIG. 11 at block 251, a user can enter a fear of hypoglycemia index (FHI), which can be used to determine and/or adjust blood glucose targets. An FHI can be represented to the user in a number of ways. In some cases, the FHI can be represented to the user as an aggressiveness index, which could be set at "prefer high," "prefer low," or "prefer moderate." In some cases, the FHI can be represented to the user as a target blood glucose level or target average blood glucose level (e.g., 100 mg/dl, 120 mg/dl, or 140 mg/dl). In some cases, the FHI can be represented to the user as a target A1C level. In some cases, the FHI can be represented to the user as a probability of going above or below a certain threshold (e.g., a five percent chance of going below 80 mg/dl, or a three percent chance of going above 200 mg/dl). In these and other cases, a user interface may be generated with an interactive feature (e.g., radio buttons, check boxes, hyperlinked images/text, drop-down list, etc.) that a user can interact with to make a selection of the FHI. In some cases, the PWD may interact with the interface to select the FHI, and in some cases, the user can be a health care professional that selects the FHI.

In some cases, each possible FHI value can correspond to a preprogrammed initial blood glucose target. For example, an FHI of "prefer high" might correspond to a preprogrammed initial blood glucose target of 140 mg/dl, an FHI of "prefer moderate" might correspond to a preprogrammed initial blood glucose target of 120 mg/dl, and an FHI of "prefer low" might correspond to a preprogrammed initial blood glucose target of 100 mg/dl. As will be discussed below, initial blood glucose targets can be adjusted over time based on data collected in methods and systems provided herein.

Modes of Operation

Methods and systems provided herein can in some cases include multiple delivery modes. In some cases, methods and systems provided herein can monitor the presence of blood glucose using one or more blood glucose measuring devices or methods, control or monitor the dispensation of insulin, and determine and/or update the user-specific dosage parameters regardless of the operating mode. For example, possible operating modes could include closed-loop or hybrid closed-loop modes that automatically adjust basal rates based on continuous glucose monitoring data (CGM) and other user-specific dosage parameters (e.g., BBR, ISF, and CR), modes that can use blood glucose monitor (BGM) data to update user-specific dosage parameters (e.g., BBRs, ISFs, and CRs) for different time blocks over longer periods of time, manual modes that require a patient to manually control the therapy program using an insulin pump, and advisory modes that recommend dosages for a user to inject using an insulin pen or syringe. By determining optimized control parameters that work across delivery modes, systems and methods provided herein can provide superior blood glucose control even when a PWD switches to a different delivery mode. For example, methods and systems provided herein may be forced to switch away from a hybrid closed-loop delivery mode that adjusts basal insulin delivery away from a BBR if a continuous glucose monitor malfunctions or the system otherwise loses access to continuous data, yet still use a personalized ISF and CR for calculating correction and/or mealtime bolus amounts. In some cases, data can be collected when the system is in an advisory or manual mode to optimize control parameters in preparation for a PWD to switch to a hybrid closed-loop system (e.g., in preparation for a PWD to start use of a continuous glucose monitor (CGM) and/or an insulin pump). In some cases, the use of a closed-loop delivery mode that adjusts basal insulin delivery away from a BBR may be prevented until a sufficient amount of current blood glucose data is available (e.g., the insulin delivery according to multiple profiles that can occur at blocks 263, 264, 265, and 272 of FIG. 11 may not occur until sufficient CGM and/or BGM data is collected at the block 271 of FIG. 11). In some cases, systems and methods provided herein can deliver insulin at the BBR rate for each diurnal period when insufficient blood glucose data is available. In some cases, methods and systems provided herein can switch between open loop and closed-loop modes based on whether there are a predetermined number of authenticated blood glucose measurements from a continuous glucose monitor within a predetermined period of time (e.g., at least two authenticated blood glucose data points within the last twenty minutes).

Automating Basal Insulin Delivery

Systems and methods provided herein can automate basal insulin delivery based on one or more stored user-specific dosage parameters (e.g., BBR, ISF, CR), one or more blood glucose targets, and/or blood glucose data. The example method depicted in FIG. 11 depicts an example process of automating basal insulin delivery as blocks 263, 264, 265, and 272. Methods and systems provided herein can use a model predictive control system that projects multiple future blood glucose levels for a future time period for multiple possible basal insulin delivery profiles and/or rates over that future time period and determines which of the multiple possible basal insulin delivery profiles and/or rates will produce future blood glucose values that approximate one or more blood glucose targets. Methods and systems provided herein can produce improved control as compared to control algorithms that merely make adjustments to basal insulin delivery without evaluating multiple possible basal insulin delivery profiles or rates. In some cases, methods and systems provided herein can predict future blood glucose values at least two hours, or at least three hours, or at least four hours, or at least five hours into the future, which can adequately consider the long term impact of increasing or decreasing the basal insulin delivery relative to the BBR. After a rate or profile is selected, the rate or profile can be delivered for a predetermined delivery period of time (for example, the block 272 of FIG. 11) prior to repeating one or more of the steps in the process of selecting a new basal insulin delivery profile or rate. In some cases, this predetermined delivery period of time can be less than the length of time for the generated basal insulin delivery profiles and/or rates and less than the time period for which future blood glucose values were estimated, thus methods and systems provided herein can dynamically make changes to basal insulin delivery based on recent blood glucose data. For example, generating basal delivery profiles at block 263 may be repeated every fifteen minutes, and the period of time evaluated at block 264 may be a four hour window such that every fifteen minutes, a new four hour window of analysis for the basal delivery profiles is generated. In this way, each delivery action is based on a prediction not only of that action, but on how the prior delivery action is determined to impact blood glucose levels for four hours into the future.

Generating Possible Basal Delivery Profiles and/or Rates for Evaluation

Possible basal insulin delivery profiles and/or rates can be generated using any suitable technique. In some cases, each generated profile or rate can be based on user-specific dosage parameters. In some cases, each generated profile or rate can be based on one or more user-specific dosage parameters that are specific to a particular diurnal period. In some cases, each generated profile or rate is based on a predetermined relationship to a stored baseline basal rate (BBR), such as indicated at block 263 in FIG. 11. In some cases, generated profiles and/or rates for analysis extend for at least two hours, at least three hours, or for at least four hours. In some cases, the generated profiles may extend for a day (e.g., twenty-four hours) or less. In some cases, each generated profile or rate includes basal insulin delivery rates based on predetermined multiples or fractions of one or more stored BBRs. In some cases, multiple insulin delivery profiles and/or rates are based on multiple diurnal-time-block-specific BBRs. In some cases, generated basal insulin delivery profiles each deliver insulin at a ratio of a BBR, such as an integer multiple of one or more stored BBRs (e.g., 0×BBR, 1×BBR, 2×BBR, and 3×BBR). In some cases, insulin delivery profiles can delivery insulin at ratios that may include both fractions and multiples of one or more stored BBRs (e.g., 0×BBR, 0.5×BBR, 1×BBR, 1.5×BBR, and 2×BBR). In some cases, generated basal insulin delivery profiles each deliver insulin at only multiples or fractions of between 0 and 3. In some cases, generated basal insulin delivery profiles each deliver insulin at only multiples or fractions of between 0 and 2. In some cases, multiple generated basal delivery profiles can include only deliveries of basal insulin at 0% of BBR, 100% of BBR, or 200% of BBR. In some cases, each generated basal delivery profile permutation has fixed future time periods. In some cases, different future time periods for permutations can have different lengths. In some cases, the number of generated basal delivery profiles or rates for evaluation is less than 100, less than 50, less than 30, less than 25, or less than 20. By limiting the number of evaluated preset permutations based on stored BBRs, methods and systems provided herein can limit an energy expenditure used to run a controller determining a basal delivery rate.

In some cases, one or more of the profiles may include an inflection point between a first insulin delivery amount for a first portion of delivery actions and a second delivery amount for a second portion of delivery actions. For example, a profile may include an inflection point between 0% and 100% between 3.5 hours and 4 hours (e.g., for the portion before the inflection point, 0% of the BBR is delivered as the delivery action and for the portion after the inflection point, 100% of the BBR is delivered as the delivery action). As another example, another profile may include an inflection point between 100% and 200% between 1 hour and 1.5 hours (e.g., before the inflection point, 100% of the BBR is delivered as the delivery action and after the inflection point, 200% of the BBR is delivered as the delivery action). In some cases, each profile may be a permutation of including one inflection point (or no inflection point) between three possible delivery actions (e.g., 0%, 100%, 200%). In some cases, more than one inflection point may be used, yielding additional profiles. In some cases, the number of profiles may be fewer than thirty. In some cases, only three profiles are analyzed in order to select between whether to delivery 0%, 100%, or 200%. In some cases, the inclusion of additional profiles assuming no basal insulin or continuing supply of maximum basal insulin can allow the system to detect an approaching predicted hypoglycemic event or an approaching predicted hyperglycemic event, and additional profiles can be selected and recorded to detect situations where future decisions are not conforming to an expected profile. In some cases, methods and systems provided herein can continue to deliver insulin according to a selected profile after the select period of time in Block 272, including changes in basal delivery rates, if reliable up-to-date blood glucose data is lost. In other cases, methods and systems provided herein will revert to another mode or alarm and stop insulin delivery if reliable up-to-date blood glucose data is lost.

In some cases, the range of possible values of the BBR for a given profile can be adjusted or modified depending on the FHI. For example, in some cases, if the FHI is "prefer low" (e.g., indicating a preference for the system to aggressively keep the PWD within range and not go high), the target blood glucose might be set around 100 mg/dl and the range for delivery may include 0%, 50%, 100%, 200%, and 300% BBR. As another example, if the FHI is "prefer high" (e.g., indicating that the PWD prefers to avoid hypoglycemic events even with a higher risk of hyperglycemic events), the target blood glucose might be set around 140 mg/dl and the range for delivery may include 0%, 100%, and 200% of BBR.

Evaluating Generated Basal Delivery Profiles and/or Rates

Referring again to FIG. 11, the evaluation of multiple generated basal insulin delivery profiles and/or rates includes projecting future blood glucose levels and comparing those to blood glucose targets. In some cases, multiple permutations may be generated and analyzed.

Predicting Future Blood Glucose Values

Systems and methods provided herein can use any suitable physiology model to predict future blood glucose values. In some cases, methods and systems provided herein can predict future blood glucose values using past and current carbohydrate, insulin, and blood glucose values.

Figure 19:
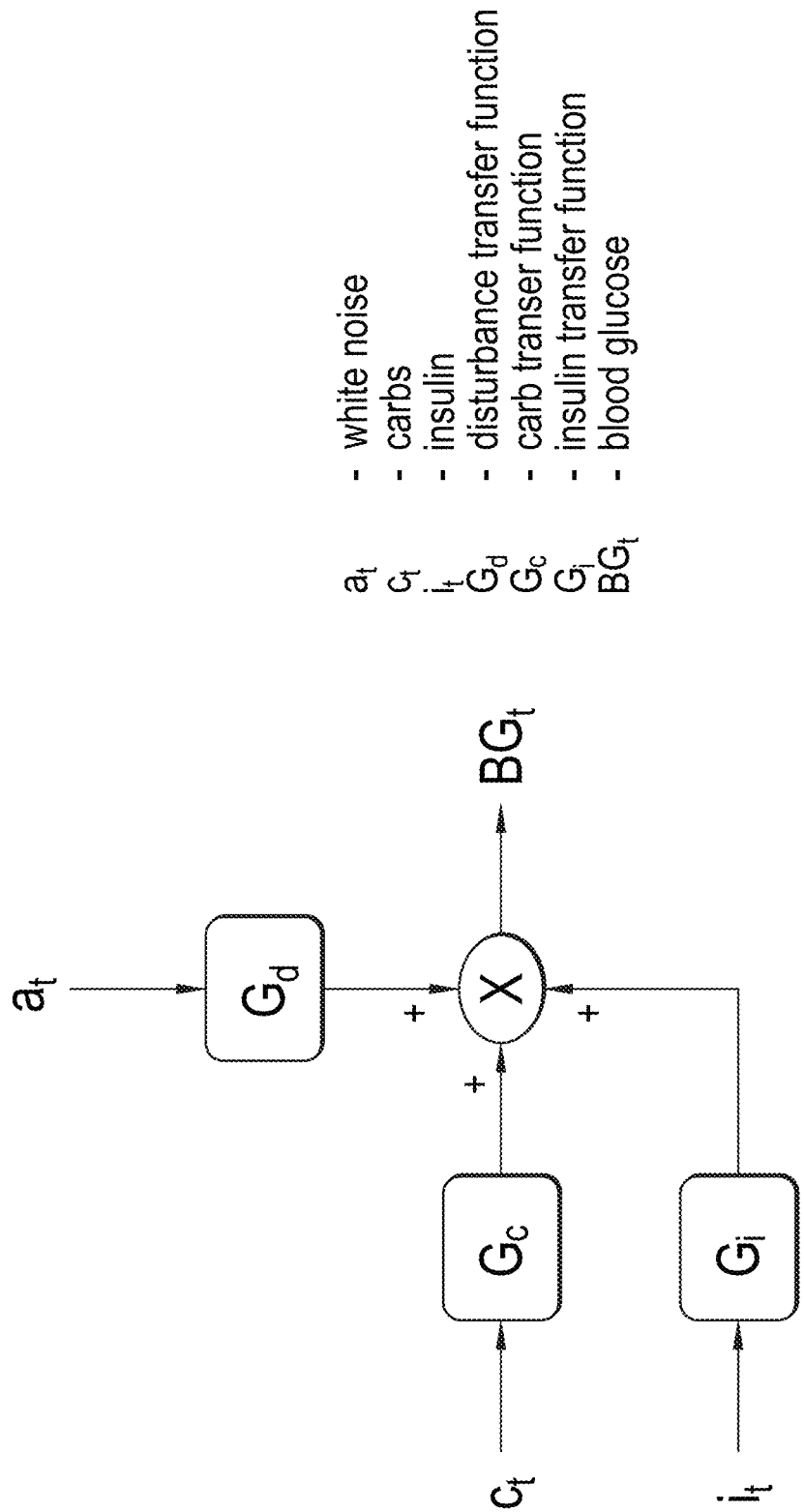
FIG. 19 is an example model for calculating future blood glucose values.

Systems and methods provided herein can in some cases estimate a first future blood glucose a model as depicted in FIG. 19. In some cases, blood glucose can be approximated using two determinist Integrating first order plus dead time (FOPDT) models for the effect of carbohydrates and insulin, combined with an autoregressive (AR2) disturbance model. Accordingly, blood glucose (BG) at time (t) can be estimated using the following equation:

$$BG_t = y_t = BGc_t + BGi_t + BGd_t = G_c c_t + G_i i_t + G_d e^{\alpha t}$$

From the equation above, the first element may represent the effect on blood glucose due to carbohydrates:

$$G_c = \frac{K_c(1-\alpha_c)B^{c_{dt}}}{(1-\alpha_c B)(1-B)}$$

where:
B is the backward shift operator such that $BY_t = Y_{t-1}$, $B^2 Y_t = Y_{t-2}$, $B^k Y_t = Y_{t-k}$ $$k_c = \frac{ISF}{CR}$$

is the carb gain (in units of mg/dl/g)

$$\alpha_c = e^{-\frac{ts}{\tau_c}},$$

where $\tau_c$ is the carb time constant (for example, approximately 30 minutes), and where ts is the sampling time (for example, a CGM may use a sampling time interval of every 5 minutes)

$$c_{dt} = \text{floor}(\tau_{dc}/ts),$$

where $\tau_{dc}$ is the carb deadtime (for example, approximately 15 minutes)

From the equation above, the second element may represent the effect on blood glucose due to insulin:

$$G_i = \frac{K_i(1-\alpha_c)B^{i_{dt}}}{(1-\alpha_i B)(1-B)}$$

where:

$k_i = -ISF$ is the insulin gain (in units of mg/dl/unit)

$$\alpha_i = e^{-\frac{ts}{\tau_i}},$$

where $\tau_i$ is the insulin time constant (for example, approximately 120 minutes)

$$i_{dt} = \text{floor}(\tau_{di}/ts),$$

where $\tau_{di}$ is the insulin deadtime (for example, approximately 30 minutes)

From the equation above, the third element may represent the effect on blood glucose due to disturbances (e.g., the AR2 disturbance model):

$$G_d e^{\alpha t}$$

and may be based on the following log-transformed AR2 model:

$$\ln\left(\frac{BGd_t}{\mu^*}\right) = \alpha_1 \ln\left(\frac{BGd_t}{\mu^*}\right) + \alpha_2 \ln\left(\frac{BGd_{t-2}}{\mu^*}\right) + \alpha_t$$

which when rearranged, yields:

$$BGd_t = BGd_{t-1}^{\alpha_1} BGd_{t-2}^{\alpha_2} \mu^{*(1-\alpha_1-\alpha_2)} e^{\alpha_t}$$

where, in some examples, $$\alpha_t \sim \text{Normal}(0, \sigma_a) \text{ and}$$

$$\sigma_a \approx 50\% \ \ln(\sigma^*) \sqrt{\frac{1+\alpha_2}{1-\alpha_2}((1-\alpha_2)^2) - \alpha_1^2}$$

with $$\mu^* \sim 10^{\text{Normal}(2.09, 0.08)} \text{ and } \sigma^* \sim 10^{\text{Normal}(0.15, 0.028)} \text{ such that}$$

$\alpha_1 \approx 1.6442$, $\alpha_2 \approx 0.6493$.

Using the above notation, expansion of the initial equation for $BG_t$ may be represented by the equation:

$$BG_t = \frac{k_c(1-\alpha_c)}{(1-\alpha_c B)(1-B)} c_{t-dt_c} + \frac{k_i(1-\alpha_i)}{(1-\alpha_i B)(1-B)} i_{t-dt_i} + BGd_{t-1}^{\alpha_1} BGd_{t-2}^{\alpha_2} \mu^{*(1-\alpha_1-\alpha_2)}$$

Systems and methods provided herein can in some cases calculate an amount of insulin on board (IOB) and/or an amount of carbohydrates on board (COB) in order to predict future blood glucose values. IOB and COB represent the amount of insulin and carbohydrates, respectively, which have been infused and/or consumed but not yet metabolized. Knowledge of IOB and COB can be useful for a user of a method or system provided herein when it comes to bolus decisions to prevent insulin stacking, but knowledge of IOB and COB can also be used in methods and systems provided herein to predict future blood glucose values.

IOB and COB represent the amount of insulin and carbohydrates, respectively, which have been infused and/or consumed but not yet metabolized. Knowledge of IOB can be useful in correcting bolus decisions to prevent insulin stacking. Knowledge of IOB and COB can be useful for predicting and controlling blood glucose. Both insulin infusion and carbohydrate consumption can involve deadtime or transportation delay (e.g., it can take ten to forty minutes for insulin and/or carbohydrates to begin to affect blood glucose). During the period immediately after entering the body (e.g., during the deadtime period), it can be beneficial to account for IOB and COB in any decisions such as bolusing. This can be called "Decision" IOB/COB. "Action" IOB/COB, on the other hand, can represent the insulin and/or carbohydrates available for action on blood glucose. In some cases, Decision IOB can be a displayed IOB, while Action IOB can be an IOB determined for use in selecting a basal delivery rate or profile in methods and systems provided herein.

From the equations above, $$BG_{i_t} = \frac{-ISF(1-\alpha_i)B^{i_{dt}}}{(1-\alpha_i B)(1-B)} i_{t-i_{dt}}$$

where $$BY_t = Y_{t-1}, \quad B^2 Y_t = Y_{t-2}, \quad B^k Y_t = Y_{t-k}$$

$$\alpha_i = e^{-\frac{ts}{\tau_i}}$$

where $\tau_1$ is the insulin time constant (for example, approximately 120 minutes)

$i_{dt} = \text{floor}(\tau_{di}/ts)$, where $\tau_{di}$ is the insulin deadtime (for example, approximately 30 minutes) and where ts is the sampling time (for example, a CGM may use a sampling time interval of every 5 minutes)

"Decision" IOB

In some embodiments, Decision IOB at time (t) ($IOB\_D_t$) may be calculated according to the following mathematical process:

$$IOB\_D_t = IOB\_D_{t-1} - \frac{BG_{i_t} - BG_{i_{t-1}}}{-ISF} + i_t$$

or, alternatively, $$\nabla IOB\_D_t = -\frac{\nabla BG_{i_t}}{-ISF} + i_t$$

substituting the equation above for $BG_{i_t}$ into the equation for $IOB\_D_t$ or $\nabla IOB\_D_t$ yields $$IOB_{D_t} = \frac{1 - \alpha_i B - (1-\alpha_i)B^{i_{dt}}}{1 - (\alpha_i + 1) + B + \alpha_i B^2} i_t$$

or, alternatively, $$\nabla IOB\_D_t = \frac{1-\alpha_i}{1-\alpha_i B} i_{t-i_{dt}} + i_t$$

"Action" IOB

In some embodiments, Action IOB at time (t) ($IOB\_A_t$) may be calculated according to the following mathematical process:

$$IOB\_A_t = \frac{1}{1-\alpha_i B} i_{t-i_{dt}}$$

For an arbitrary series of insulin infusions, using an infinite series of expansions of $\frac{1}{1-\alpha_i B}$, $IOB\_A_t$ may be represented by $$IOB_{A_t} = \sum_{k=0}^{n} \alpha_i^k i_{t-k-i_{dt}}$$

Stated another way, $$BGi_t = \frac{-ISF(1-\alpha_i)}{1-B} IOB\_A_t$$

The formulas for COB, including Action COB and Decision COB, may be developed in a similar fashion, using the equation above related to $G_c$:

$$G_{ct} = \frac{k_c(1-\alpha_c)B^c dt}{(1-\alpha_c B)(1-B)}$$

Accordingly, future blood glucose data can be estimated using current or recent blood glucose data, data about when carbohydrates were consumed, and/or data regarding when insulin was and/or will be administered. Moreover, because evaluated insulin delivery profiles and/or rates include basal insulin delivery rates above and below the BBR, those insulin delivery rates above BBR can be added to the IOB calculation and insulin delivery rates below the BBR can be subtracted from the IOB. In some cases, a variation in a Decision IOB due to actual variations from BBR can be limited to positive deviations in order to prevent a user from entering an excessive bolus.

Estimating Glucose Levels from Blood Glucose Data

Referring back to FIG. 1, continuous glucose monitor 50 and blood glucose meter 70 can both provide blood glucose data to system 10. The blood glucose data, however, can be inaccurate. In some cases, continuous glucose monitor 50 can be replaced (or have sensor shaft 56 replaced) at regular or irregular intervals (e.g., every three days, every five days, every seven days, or every ten days). In some cases, data from blood glucose meter 70 can be used to calibrate the continuous glucose monitor 50 at regular or irregular intervals (e.g., every three hours, every six hours, every twelve hours, every day, etc.). In some cases, systems and methods provided herein can remind a user to change the continuous glucose monitor 50 or calibrate continuous glucose monitor 50 using blood glucose meter 70 based on data from continuous glucose monitor 50 and/or at regular intervals. For example, if the pattern of insulin delivery varies greatly from an earlier predicted pattern of insulin deliveries may indicate that the continuous glucose monitor 50 requires maintenance and/or replacement.

In some cases, methods and systems can determine an accuracy factor for blood glucose data from the continuous glucose monitor 50 based upon when the particular continuous glucose monitor sensor shaft 56 was first applied to the PWD and/or when the particular continuous glucose monitor 50 was last calibrated using blood glucose data from blood glucose meter 70. In some cases, methods and systems provided herein make adjustments to future blood glucose targets based on a calculated accuracy factor for data from the continuous glucose monitor 50 in order to reduce a risk of hypoglycemia. In some cases, methods and systems provided herein can estimate the current blood glucose level as being a predetermined number of standard deviations (e.g., 0.5 standard deviations, one standard deviation, two standard deviations) below data received from continuous glucose monitor 50 based on the accuracy factor in order to reduce a risk of hypoglycemia.

After continuous glucose monitor 50 is calibrated or replaced with a new continuous glucose monitor or has a new sensor shaft 56 installed, however, a discontinuity of reported glucose data from the continuous glucose monitor 50 can occur. In some cases, methods and systems provided herein, however, can use and report historical blood glucose values in selecting insulin basal rates and/or profiles. In some cases, methods and systems provided herein can revise stored and/or reported blood glucose levels based on data from one or more continuous glucose monitors in order to transition between different continuous glucose monitor sensors and/or to data produced after a calibration. In some cases, a continuous glucose monitor 50 can provide each blood glucose value with an estimated rate of change, and the rate of change information can be used to retrospectively adjust one or more historical estimated blood glucose values from data from a continuous glucose monitor 50. For example, the rate of change of the pre-calibration reported blood glucose value may be used to determine an estimated post-calibration value assuming the same rate of change. A ratio of the post-calibration reported blood glucose value to the estimated post-calibration value can then be used to linearly interpolate multiple historical blood glucose values based on that ratio. In some cases, all readings between calibrations can be linearly interpolated. In some cases, data from a predetermined amount of time prior to a calibration can be linearly interpolated (e.g., fifteen minutes, thirty minutes, one hour, two hours, three hours, or six hours).

Analyzing Variations from Targets

Methods and systems provided herein can evaluate each future basal delivery profile by predicting blood glucose for the basal delivery profiles and calculating a variation index of the predicted blood glucose values from the target blood glucose values. Methods and systems provided herein can then select the profile of basal rate delivery actions that corresponds to the lowest variation index. The variation index can use a variety of different mathematical formulas to weight different types of variations. The variation index can be a cost function. In some cases, methods and systems provided herein can use a cost function that sums up squares of differences for the projected blood glucose values from target blood glucose values for multiple diurnal time segments. Methods and systems provided herein can use any suitable cost function. In some cases, cost functions can sum the absolute value of the difference between each predicted blood glucose value and each blood glucose target. In some cases, cost functions used in methods and systems provided herein can use a square of the difference. In some cases, cost functions used in methods and systems provided herein can use a square of the difference between the logs of each predicted blood glucose level and each corresponding blood glucose target. In some cases, cost functions used in methods and systems provided herein can assign a higher cost to blood glucose values below the blood glucose target in order reduce the risk of a hypoglycemic event. In some cases, a profile that has the lowest value of loss may be selected. In some cases, cost functions provided herein can include elements that additional bias the selected profile toward a profile that maintains the previously administered basal rate and/or that delivers the baseline basal rate, which may prevent the system from changing delivery rates every time a basal delivery profile or rate is selected in block 265, as shown in FIG. 11. In some cases, the cost function can square the difference between the log of the values in order to provide a higher cost for projected lows than projected highs.

Selecting a Basal Insulin Delivery Profile or Rate

Methods and systems provided herein can then select a basal profile or rate that produces the lowest cost function value. With reference to FIG. 11, at block 272 insulin can then be delivered according to the selected profile for an amount of time. In some cases, the amount of time is a predetermined amount of time. In some cases, the predetermined amount of time is less than the time horizon for the estimated future blood glucose values and the length of time for the selected basal delivery profile. In some cases, the predetermined amount of time is ninety minutes or less, sixty minutes or less, forty-five minutes or less, thirty minutes or less, twenty minutes or less, fifteen minutes or less, ten minutes or less, or five minutes or less. After the period of time, the system can again repeat the operations at blocks 263, 264, 265, and 272 to select and deliver a basal insulin for a subsequent period of time.

Adjusting User-Specific Dosage Parameters

Methods and systems provided herein can make adjustments to the user-specific dosage parameters. For example, FIG. 11 includes the block 281 for detecting time periods when an amount of delivered basal insulin is different from a BBR, which can then be used to adjust user-specific dosage parameters at block 262. These updated user-specific dosage parameters can then be used to generate new basal delivery profiles at block 263 and used at block 264 to evaluate different basal delivery profiles. For example, for a BBR of 1.46 U/hour (associated with a TDB of 35 U/day), if a diurnal period under consideration is one hour and for the first forty-five minutes, insulin was delivered at a rate of 2.92 U/hour (e.g., 2× the BBR) and only the last fifteen minutes was delivered at a rate of 1.46 U/hour (e.g., 1× the BBR), user-specific dosage parameters for a related diurnal time period (e.g., that same hour on another day in the future, or a preceding diurnal time period on a day in the future) may be adjusted.

In some cases, methods and systems provided herein can make adjustments for BBR, ISF, and/or CR for multiple diurnal periods based on variations in the insulin amounts actually delivered for that diurnal period compared to the baseline basal insulin rate for that diurnal period. In some cases, diurnal periods can have a same length of time as a predetermined length of time for the delivery of a selected insulin delivery. In some cases, a diurnal period can be greater than a predetermined length of time for the delivery of a selected insulin delivery, for example, multiple doses of insulin may be delivered during a single diurnal period. In some cases, a diurnal period can be fifteen minutes, thirty minutes, one hour, two hours, etc. In some cases, an actual delivery of insulin for a diurnal period must surpass a predetermined threshold above or below the BBR for that diurnal period in order for user-specific dosage parameters (e.g., BBR, ISF, CR) to be adjusted for that diurnal period. For example, diurnal periods can be one hour long, but each basal delivery profile can be delivered for fifteen minute time periods before methods and systems provided herein determine a new basal insulin delivery profile, and methods and systems provided herein can require that the total basal insulin delivery for the diurnal period be at least greater than 50% of the BBR to increase the BBR for that diurnal period or at 50% or less than the BBR to decrease the BBR for that diurnal period. Using the example from above, for a BBR of 1.46 U/hour, if a diurnal period under consideration is one hour and for the first forty-five minutes (e.g., three iterations of profile generation and delivery actions), insulin was delivered at a rate of 2.92 U/hour (e.g., 2× the BBR) and only the last fifteen minutes (e.g., one iteration of profile generation and delivery action) was delivered at a rate of 1.46 U/hour (e.g., 1× the BBR), the total amount delivered would be at 175% of the BBR for the one hour diurnal period, or an average ratio of 1.75× the BBR. In some cases, because the 175% exceeded 150% of the BBR, methods and systems of the present disclosure may adjust user-specific dosage parameters. As another example using the same 1.46 U/hour BBR and a two hour diurnal time period and delivery profiles reformulated every fifteen minutes, if the first forty-five minutes delivered no insulin (0× the BBR) and the last hour and fifteen minutes delivered 1.46 U/hour, the total amount delivered may be 62.5% of the BBR, or 0.625× of the BBR. In some cases, because the 62.5% did not drop below 50% of the BBR, methods and systems of the present disclosure may not adjust the user-specific dosage parameters and may maintain the user-specific dosage parameters for the particular diurnal period.

An adjustment to the CR, ISF, and BBR can be any suitable amount. In some cases, the adjustment to the BBR is less than the difference between the delivered basal insulin and the previously programmed BBR. In some cases, a change to each user-specific dosage parameter (e.g., BBR, ISF, and CR) is at a predetermined percentage or value. For example, in some cases, each of BBR and ISF can be increased by 5%, 3%, or 1% and CR decreased by the same percent for every period where the amount of delivered basal insulin exceeds the BBR by at least 25%. In some cases, BBR and ISF can be decreased by 5%, 3%, or 1% and CR increased by the same percent for every period where the amount of delivered basal insulin exceeds the BBR by at least 25%. By setting each adjustment at a low level, methods and systems provided herein can eventually be personalized for the PWD without over adjusting the system based on an unusual day (e.g., to mitigate the risk of short term disturbances being mistaken for changes in physiological parameters). In some cases, the adjustment to CR, ISF, and BBR may be based on a relationship between CR, ISF, and BBR, rather than a fixed amount or percentage. In some cases, CR, ISF, and BBR can be adjusted based on a predetermined relationship between their log-transformed values. In some cases, the adjustments to CR, ISF, and BBR may be performed independently. In these and other cases, systems and methods provided herein can monitor for variations in adjustments to CR, ISF, and/or BBR away from a relationship between CR, ISF, and BBR. In such cases, a notification may be provided to a user (e.g., the PWD or a health care provider) that the systems and methods of the present disclosure had adjusted one or more user-specific dosage guidelines outside of or away from a relationship between CR, ISF, and BBR.

In some cases, systems and methods provided herein can update or adjust user-specific operating parameters for select time blocks every twenty-four hours. In some cases, diurnal periods can be updated dynamically (e.g., immediately after a basal delivery profile or rate is selected). In some cases, diurnal periods can be updated by reusable pump controller 200, by mobile computing device 60, or using a remote server in the cloud. In some cases, the length of diurnal periods can vary depending on the time of day (e.g., nighttime diurnal periods could be longer) or depending on the user-specific dosage parameter (e.g., BBRs might have fifteen minute diurnal periods while the CR and ISF might have one hour diurnal periods).

In some cases, when performing an adjustment, a related diurnal period may be adjusted based on variation from the BBR for a given diurnal period. For example, if an adjustment were to be performed because delivery from 2 PM to 3 PM exceeded 150% of the BBR, an adjustment may be made to the user-specific dosage parameters for the same time on a different day in the future (e.g., 2 PM to 3 PM on the next day) or a preceding diurnal period on a different day in the future (e.g., 1 PM to 2 PM on the next day or 12 PM to 1 PM on the next day, etc.). In some cases, modifying a preceding diurnal period may adjust more appropriately for variations in BBR and/or other user-specific dosage parameters because of the delay of effect after delivery of insulin and/or the delay of effect after consumption of carbohydrates (e.g., if a PWD repeatedly goes high between 2 PM and 3 PM, the PWD may need additional insulin during the 1 PM to 2 PM hour).

In some cases, systems and methods disclosed herein can smooth adjustments to user-specific dosage parameters in one diurnal period relative to other diurnal periods. For example, in some cases, a proposed adjustment to a BBR for a first diurnal period may be compared to one or more preceding diurnal periods and one or more following diurnal periods. If the proposed adjustment is a threshold amount different from one or more of the preceding or following diurnal period values, the proposed adjustment may be modified to avoid drastic jumps between diurnal periods. For example, if a preceding diurnal period had a BBR of 1.06 U/hour and the proposed adjustment was from a BBR of 1.4 U/hour to a BBR of 1.90 U/hour, the adjustment may be reduced to smooth the transition from the preceding diurnal time period. In some cases, the smoothing may include adjusting preceding or following diurnal time periods in addition to the diurnal time period under consideration. In these and other cases, such adjustment may be performed once per day or at another periodic time such that following diurnal periods may have already occurred and the smoothing is not being performed based on projections. For example, the diurnal period from 1 PM to 2 PM may be analyzed for potential adjustment at 4 PM such that the diurnal periods from 11 AM to 12 PM and 12 PM to 1 PM and from 2 PM to 3 PM and 3 PM and 4 PM are available in considering any adjustment and/or smoothing to perform on the user-specific dosage parameters for the 1 PM to 2 PM diurnal period.

In some cases, systems and methods disclosed herein can adjust user-specific dosage parameters in a diurnal period based on the FHI. For example, if the FHI is high (e.g., indicating a preference that the PWD not go low), the range for adjusting the BBR may be limited to a relatively small change (e.g., 0.5%, 1%, 1.5%, etc.). As another example, if the FHI is low (e.g., indicating that the PWD is not as concerned about going low), the range for adjusting the BBR may include a broader range of changes (e.g., up to a 5% change).

Adjusting Blood Glucose Targets

Methods and systems provided herein can make adjustments to the blood glucose targets. For example, FIG. 11 includes the block 283 for analyzing the variability of CGM and/or BGM data (e.g., data from the CGM 50 and/or the BGM 70 of FIG. 1), which can then be used to adjust blood glucose targets at the block 261. In some cases, blood glucose targets are set for diurnal periods. In some cases, the diurnal periods for blood glucose targets are at least fifteen minutes long, at least thirty minutes long, at least one hour long, or at least two hours long. In some cases, blood glucose targets can have a constrained range. In some cases, blood glucose targets must be at least 80 mg/dL, at least 90 mg/dL, at least 100 mg/dL, at least 110 mg/dL, or at least 120 mg/dL. In some cases, blood glucose targets must be no greater than 200 mg/dL, no greater than 180 mg/dL, no greater than 160 mg/dL, no greater than 140 mg/dL, or no greater than 125 mg/dL. In some cases, a constrained range is between 100 mg/dL and 160 mg/dL. These updated blood glucose targets can then be used at block 264 to evaluate different basal delivery profiles.

Updated blood glucose targets for a particular diurnal period can be based on historical blood glucose patterns for the PWD and the risk of hypoglycemia for the PWD over the course of a day. The updated blood glucose targets can also consider a set FHI. For example, based on an FHI selection, an initial blood glucose target at a conservative level (e.g., 120 mg/dl) can be set, and over the course of a period of days and/or weeks as more information is gained about variability patterns, the blood glucose target(s) can be adjusted. A slow adjustment can prevent the blocks 283 and 261 from overreacting to short term disturbances but still allow blood glucose target individualization to a PWD's lifestyle and habits over time.

In some cases, methods and systems provided herein can also allow a user to temporarily or permanently adjust blood glucose targets by adjusting their fear of hypoglycemia index (FHI). In some cases, a user adjustment to FHI can result in blood glucose targets being temporarily or permanently adjusted to blood glucose targets based on the variability of CGM (and optionally BGM) data for multiple diurnal periods. In some cases, a user adjustment to FHI can add or subtract a predetermined value from a previously used blood glucose target (e.g., an adjustment from "prefer low" to "prefer medium" could add 20 mg/dL to each stored blood glucose target). In some cases, a temporary adjustment to FHI could analyze variability data for multiple time blocks and set a new blood glucose target for each diurnal period based on the variability data for that time block (e.g., an adjustment from "prefer low" to "prefer medium" could adjust the blood glucose target for each diurnal period from a level estimated to send the PWD below a threshold of 70 mg/dL about 5% of the time to a level estimated to send the PWD below a threshold of 70 mg/dL about 3% of the time).

Allowing a PWD to change the FHI for temporary time periods or otherwise use some form of temporary override may allow a PWD to tell the system that the PWD is about to or is experiencing some activity or condition that might impact their blood glucose levels. For example, a PWD that is about to exercise might set a temporary FHI of "prefer high" to offset the risk that exercise will send the PWD low for that period of time. In some cases, a PWD might set a temporary FHI of "prefer low" if the PWD is feeling sick in order to offset the risk that the sickness will result in high blood glucose levels. In some embodiments, such a temporary override may be a separate setting or entry other than the FHI. In these and other cases, in addition to a preferred range (e.g., "high" or "low"), the user may be able to select a temporary override of a target blood glucose level or range (e.g., approximately 120 mg/dL or between 120 mg/dL and 200 mg/dL, etc.), or may select a particular activity or circumstance the PWD will participate in or is experiencing (e.g., exercising, sickness, menses, driving, etc.).

In some cases, after a temporary override is input, methods and systems of the present disclosure can select a new profile to follow based on the profile more closely aligning with the temporary override. In these and other cases, a new set of profiles can be generated before selecting the new profile. Additionally or alternatively, after a temporary override is input, methods and systems of the present disclosure can temporarily modify the BBR. In some cases, after the BBR has been modified, a new set of profiles may be generated based on the temporarily modified BBR.

In some cases a log of temporary overrides can be generated. For example, each time a user (e.g., the PWD) inputs an override, an entry can be created in the log that includes what override was selected, what starting and ending times, and/or what the reason for the override was. In these and other cases, the log can be periodically provided to a healthcare professional, for example, via email or some other electronic message. Additionally or alternatively, in some cases the log can be parsed for patterns. For example, the PWD may input a temporary override every Monday, Wednesday, and Friday from 6 PM to 7 PM when the PWD exercises. The log can be parsed to find such patterns of overrides. In these and other cases, methods and systems of the present disclosure can modify a BBR based on the patterns. Continuing the example, the BBR may be lowered for the diurnal period of 6 PM to 7 PM on Monday, Wednesday, and Friday because of a PWD repeatedly entering a temporary override during that diurnal period that the PWD is exercising and not to go low.

Overall System

Methods and systems provided herein can control basal insulin delivery over time and adjust basal user-specific dosage parameters and blood glucose targets for multiple diurnal periods to personalize the user-specific dosage parameters over time. For example, FIG. 20 illustrates various examples of user interfaces (e.g., X-400, X-410, X-420, and X-430) displaying various aspects of the present disclosure.

Figure 20:
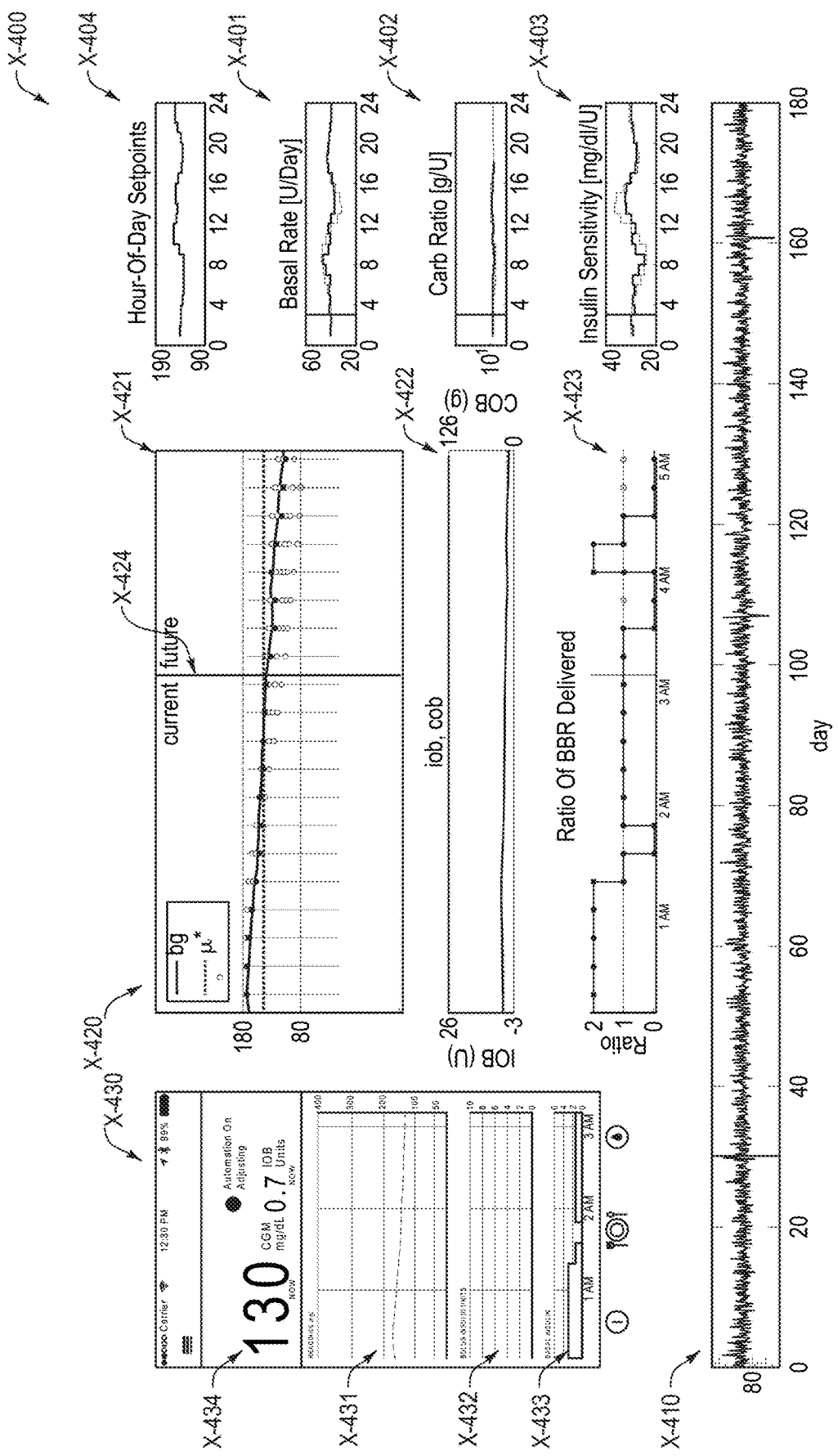
FIG. 20 is an example user interface associated with methods and systems for delivery of insulin described herein.

In some cases, FIG. 20 illustrates a simulation of a method provided herein, showing how methods and systems provided herein may generate a user interface X-400 that may illustrate BBRs X-401, CRs X-402, ISFs X-403, and blood glucose targets X-404 set for multiple time blocks. For example, after a system (e.g., the system 10 of FIG. 1) has run on a PWD after thirty days, user-specific dosage parameters may be personalized based on adjustments made to the user-specific dosage parameters. For example, the user interface X-400 may align the various user-specific dosage parameters over various diurnal periods throughout a day. For example, the BBR X-401 may be higher around meal times (e.g., nine AM, twelve PM, and seven PM), and lower while the PWD is sleeping (e.g., eleven PM to five AM). As an additional example, the CR X-402 and ISF X-403 may follow a similar trajectory of variation as illustrated for the BBR X-401.

In some cases, as illustrated in user interface X-410 of FIG. 20, methods and/or systems of the present disclosure (including, for example, back-end computer systems) may monitor and/or track blood glucose levels over time. For example, the user interface X-410 may illustrate glucose levels for one hundred and eighty days, with a bar indicating the last thirty days. In some cases, when adjusting user-specific dosage parameters, methods and systems of the present disclosure may disregard readings older than thirty days, or may weight more recent readings more heavily than older readings.

In some cases, the user interface X-420 may include time aligned charts (including chart X-421, chart X-422, and chart X-423) that can show a six hour window of the timeline illustrated in user interface X-410. As illustrated in FIG. 20, chart X-421 depicts the current blood glucose values as well as the predictions that have been made over time for that particular delivery time. For example, once the "current" bar X-424 is reached, there may have been multiple predictions made for each time segment. As the window extends further into the future, the number of predictions may be lower. The chart X-422 illustrates the calculated IOB and the calculated COB for the PWD. The chart X-423 indicates whether the method or system delivered 0% of the BBR, 100% of the BBR, or 200% of the BBR for fifteen minute time segments.

As illustrated in FIG. 20, the user interface X-430 depicts a possible user interface for a PWD showing some data that may be displayed on a mobile device of a PWD (e.g., the mobile computing device 60 of FIG. 1). In some cases, only the data prior to the bar X-424 (e.g., historic data) may be shown in the user interface X-430. In a first part X-431 of the user interface X-430, historic blood glucose data can be displayed. In a second section X-432, announced meals and bolus insulin deliveries can be displayed. In a third section X-433, the rates of basal delivery can be displayed. The section X-433 can differ from chart X-423 by displaying the actual rates of basal delivery rather than a ratio of the rate delivered to the BBR. Section X-434 can display a current blood glucose reading, a current IOB, and/or an indication of whether the system is automating. In some cases, more or less information can be displayed on the user interface X-430 than illustrated in FIG. 20. For example, the user interface X-430 may include any of the information from the user interfaces X-400, X-410, and/or X-420 in any combination.

Additional Details About Example Pump Assembly

Figure 21:
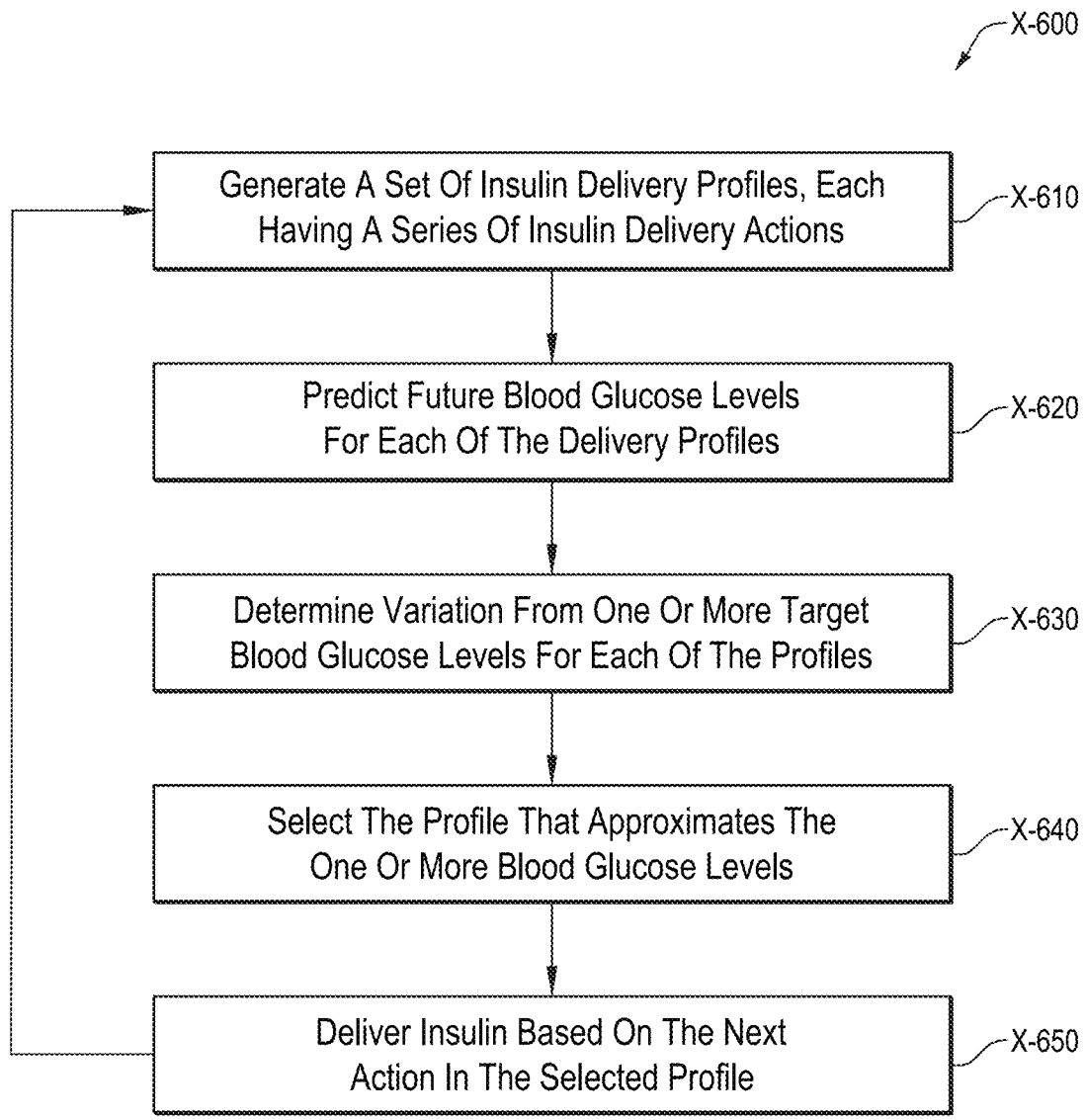
FIG. 21 is a flowchart of an example method of using insulin delivery profiles.

FIG. 21 illustrates a flow diagram of an example method X-600 of using insulin delivery profiles. The method X-600 may be performed by any suitable system, apparatus, or device. For example, the system 10, the pump assembly 15, the mobile computing device 60 of FIG. 1, and/or a remote server may perform one or more of the operations associated with the method X-600. Although illustrated with discrete blocks, the steps and operations associated with one or more of the blocks of the method X-600 may be divided into additional blocks, combined into fewer blocks, or eliminated, depending on the desired implementation.

At block X-610, a set of insulin delivery profiles can be generated, each having a series of insulin delivery actions. For example, the pump assembly 15 may generate a series of potential delivery actions that may include permutations based on one or more potential inflection points in the delivery actions.

At block X-620, a prediction can be made of future blood glucose levels for each of the delivery profiles. For example, the pump assembly 15 and/or the mobile computing device 60 of FIG. 1 can generate a prediction of future blood glucose levels at various points in time if a particular profile is followed. Such prediction may be based on the effect of glucose, insulin, carbohydrates, and/or other disturbances projected for the blood glucose levels at the various points in time.

At block X-630, a determination can be made as to variations from a target blood glucose level for each of the profiles. For example, the pump assembly 15 and/or the mobile computing device 60 of FIG. 1 may compare the predicted blood glucose levels to a target blood glucose level for each of the various points in time. In some cases, the target blood glucose level may be constant and in other cases, the target blood glucose level may vary over time. In these and other cases, the variation may be measured as a distance between the target blood glucose level and the projected blood glucose level, or a square of the difference, etc., as described above.

At block X-640, the profile that approximates the target blood glucose level can be selected. In some cases, the profile that minimizes variation from the target blood glucose level may be selected. For example, a cost function can be utilized and the profile with the lowest cost can be selected as the profile that approximates the target blood glucose level.

At block X-650, insulin may be delivered based on the next action in the selected profile. For example, control circuitry 240 of the pump assembly 15 may send a message to the pump portion of the pump assembly 15 to deliver insulin based on the next action in the selected profile. For example, a next action may indicate that the pump is to deliver 0x, 1x, or 2x of a BBR. The next action can be the first delivery action in the set of actions of the profile.

In some cases, after the block X-650, the method X-600 can return to the block X-610 to generate another set of insulin delivery profiles, predict future blood glucose levels, determine variations from a target blood glucose level, etc. In some cases, the method X-600 can be performed iteratively each time a PWD is to receive a dose of basal insulin. In these and other cases, the method X-600 can routinely update delivery actions based on a repeatedly updated projection of the blood glucose levels of the PWD and the effect a particular delivery action may have on the blood glucose levels. In some cases, methods and systems provided herein can change modes if there is a lack of reliable CGM data at this point in time (e.g., the system can change modes to a mode where BBR is delivered and potentially provide notice that the system has exited the automation mode).

Modifications, additions, or omissions may be made to the method X-600 without departing from the scope of the present disclosure. For example, the operations of the method X-600 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 22:
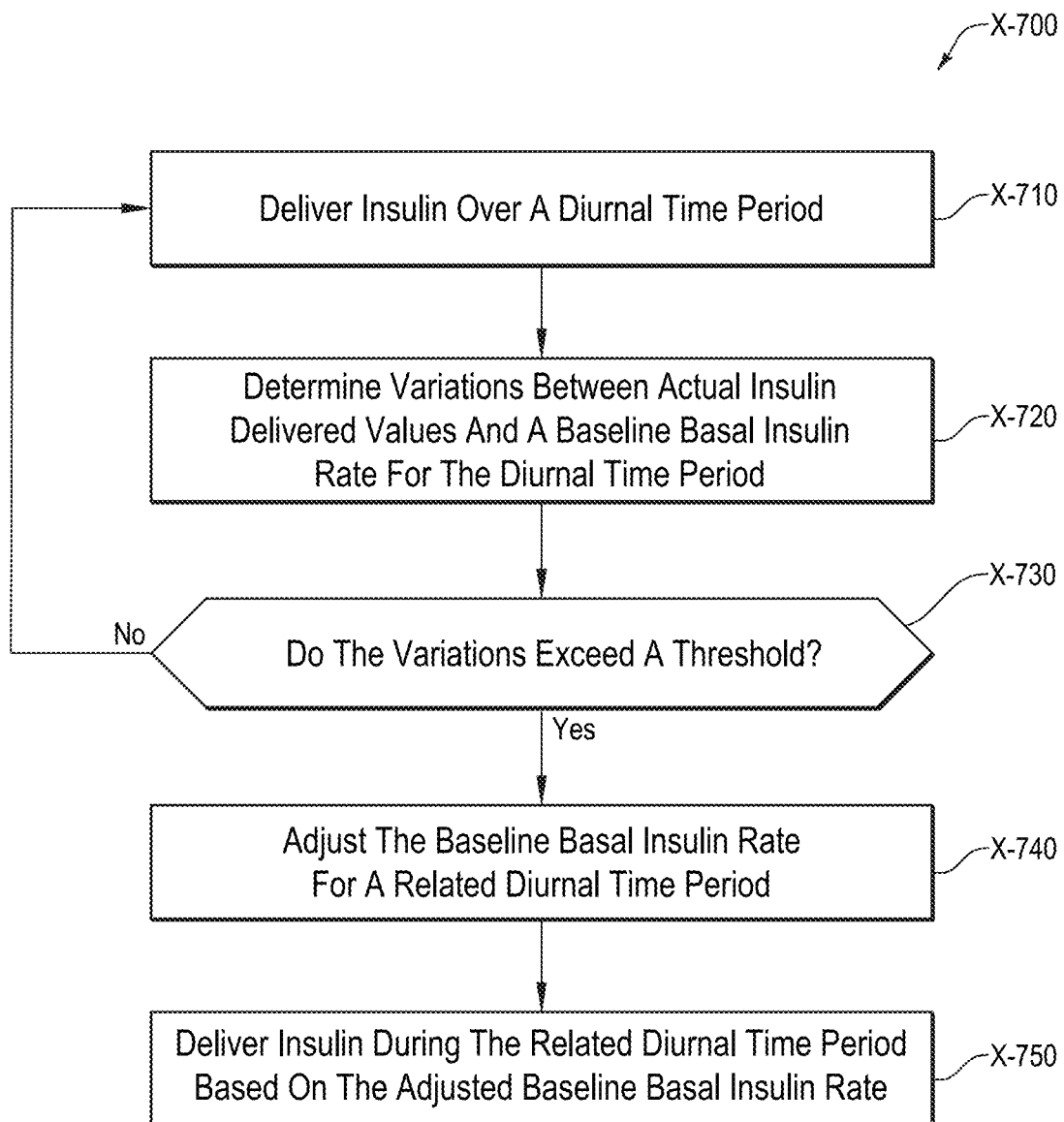
FIG. 22 is a flowchart of an example of adjusting insulin delivery rates.

FIG. 22 illustrates a flow diagram of an example method X-700 of adjusting insulin delivery rates. The method X-700 may be performed by any suitable system, apparatus, or device. For example, the system 10, the pump assembly 15, the mobile computing device 60 of FIG. 1, and/or a remote server may perform one or more of the operations associated with the method X-700. Although illustrated with discrete blocks, the steps and operations associated with one or more of the blocks of the method X-700 may be divided into additional blocks, combined into fewer blocks, or eliminated, depending on the desired implementation.

At block X-710, insulin can be delivered over a diurnal time period. For example, the pump assembly 15 of FIG. 1 can deliver insulin to a PWD based on a BBR for the diurnal time period. In some cases, the insulin may be actually delivered at multiple points in time throughout the diurnal time period as a ratio of the BBR, such as 0x, 1x, and 2x.

At block X-720, variations between actual insulin delivered values and the BBR for the diurnal time period can be determined. For example, if the delivery actions throughout the diurnal time period deliver a ratio of the BBR, the actual delivery actions may be averaged over the diurnal time period to find an average ratio for the diurnal time period. In these and other cases, the actual insulin delivered values can be based on periodically projected blood glucose levels and the BBR. For example, a set of insulin delivery profiles can be generated and a delivery action selected as described in the present disclosure (e.g., as described in FIG. 21).

At block X-730, a determination is made as to whether the variations between the actual insulin delivered values and the baseline basal insulin rate exceeds a threshold. If the variations do exceed the threshold, the method X-700 may proceed to the block X-740. If the variations do not exceed the threshold, the method X-700 may proceed back to the block X-710. In some cases, the threshold may be based on a ratio of the baseline basal delivery rate. For example, the threshold may include that the average rate over the diurnal period be above 150% of the BBR or below 50% of the BBR for the actual delivery values over the diurnal time period.

At block X-740, the baseline basal insulin rate can be adjusted for a related diurnal time period. For example, the BBR can be adjusted higher by a certain amount (e.g., 1%, 2%, or 5%) if the variations went above a threshold and can be adjusted lower by a certain amount (e.g., 1%, 2%, or 5%) if the variations went below a threshold. In some cases, the related diurnal time period can be the same block of time (e.g., if the variations exceeded the threshold during the 2 PM to 3 PM diurnal period, then the BBR from 2 PM to 3 PM of the next day may be adjusted) on another day in the future, and in some cases, the related diurnal time period can be a different time on another day (e.g., if the variations exceeded the threshold during the 2 PM to 3 PM diurnal period, then the BBR from 1 PM to 2 PM of the next day may be adjusted). In some cases, such an adjustment may be performed once per day for all the diurnal periods of that day.

In some cases, the adjustment at block X-740 can include smoothing of the adjustment. For example, a potential modification can be compared to the BBR of the preceding diurnal time period or the following diurnal time period, and may modify the adjustment to be closer to the other diurnal time periods. Additionally or alternatively, the BBR can be smoothed by comparing the potential modification to BBRs of the same time of day for preceding days to determine whether the potential modification may be responsive to an unusual day.

In some cases the adjustment at block X-740 can consider other factors. For example, the adjustment can be based on penalizing a modification that increases the probability of the PWD having a hypoglycemic event (e.g., by penalizing modifications that may increase the probability of the blood glucose levels of the PWD falling below a threshold low blood glucose level). In these and other cases, in addition to or in place of adjusting the BBR, other user-specific dosage-guidelines can be adjusted. For example, ISF and CR can also be adjusted according to the present disclosure. In some cases, if BBR is adjusted higher, ISF may be adjusted higher by the same or an approximately proportional percentage amount and CR may be adjusted lower by the same or an approximately proportional percentage amount of the BBR.

At block X-750, insulin may be delivered during the related diurnal time period based on the adjusted baseline basal insulin rate. For example, the insulin pump can deliver insulin based on the adjusted baseline basal insulin rate. In some cases, such delivery can include a control device (e.g., the control circuitry 240 of FIG. 2B) sending a message to the insulin pump to deliver insulin.

Modifications, additions, or omissions may be made to the method X-700 without departing from the scope of the present disclosure. For example, the operations of the method X-700 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 23:
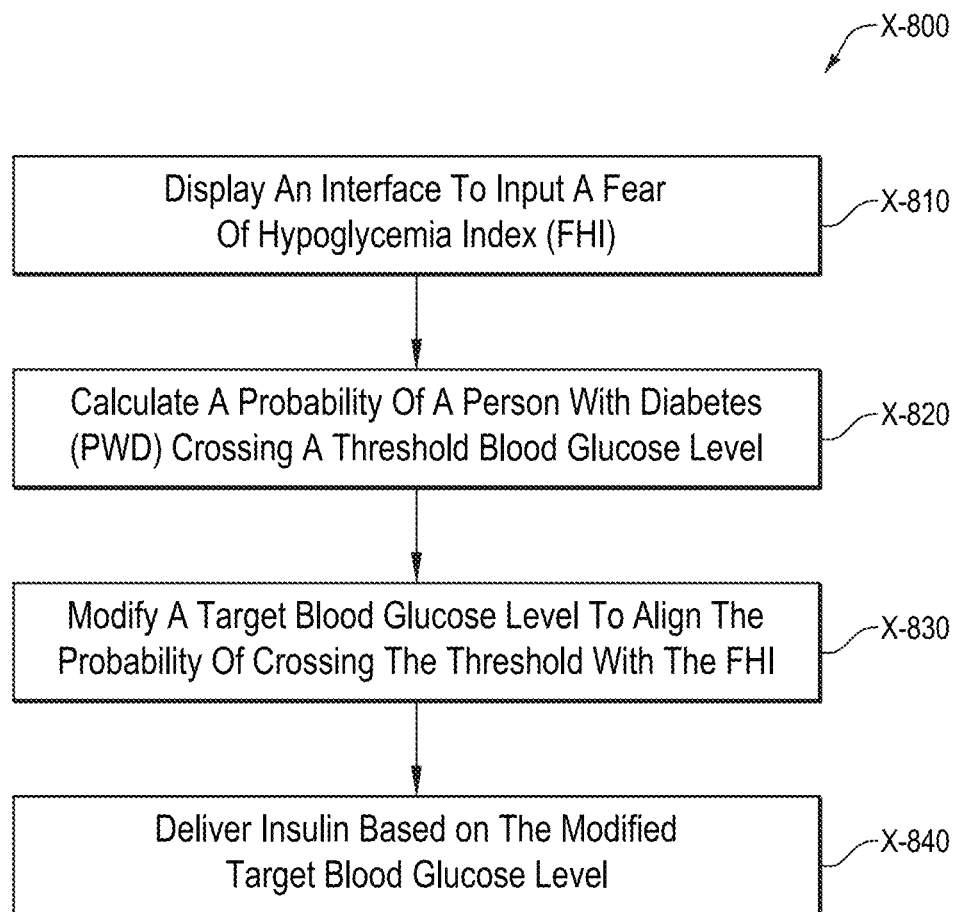
FIG. 23 is a flowchart of an example of utilizing a fear of hypoglycemia index associated with method and systems for delivery of insulin described herein.

FIG. 23 illustrates a flowchart of an example method X-800 of utilizing a fear of hypoglycemia index. The method X-800 may be performed by any suitable system, apparatus, or device. For example, the system 10, the pump assembly 15, the mobile computing device 60 of FIG. 1, and/or a remote server may perform one or more of the operations associated with the method X-800. Although illustrated with discrete blocks, the steps and operations associated with one or more of the blocks of the method X-800 may be divided into additional blocks, combined into fewer blocks, or eliminated, depending on the desired implementation.

At block X-810, an interface can be displayed to a user to input an FHI. For example, an interface can be displayed on a mobile computing device (e.g., the mobile computing device 60 of FIG. 1) and/or to a terminal connected over a network such as the internet to a remote server. In some cases, the user (e.g., a PWD or a healthcare professional) can be presented with an interactive feature from which the user can select the FHI. In these and other cases, the interface can include a variety of ways that the user can input the FHI, such as a preferred blood glucose level, a preferred probability of going above or below a certain threshold, a textual description of a blood glucose level (e.g., "prefer high"), etc. In these and other cases, the FHI can correspond to a threshold blood glucose level and an acceptable probability of crossing the threshold blood glucose level. For example, "prefer high" may designate a low threshold blood glucose level as 100 mg/dl, with a target blood glucose level of 150 mg/dl, and a high threshold blood glucose level of 220 mg/dl, and an acceptable probability of 5% for exceeding either the low or the high threshold values.

At block X-820, a probability of a PWD crossing a threshold blood glucose level is calculated. For example, a calculation can be made as to how likely the PWD is to cross the threshold blood glucose level corresponding to the FHI. In these and other cases, the probability of crossing the threshold can also be compared to the acceptable probability of crossing the threshold. For example, if the FHI indicates that a 5% probability of exceeding a threshold is acceptable, the calculated probability of exceeding the threshold can be compared to the 5% acceptable probability.

At block X-830, target blood glucose level can be modified to more closely align the probability of crossing the threshold with the FHI. For example, if the probability of dropping below a threshold is higher than the acceptable probability, the target blood glucose level may be adjusted higher such that the probability is closer to the acceptable probability. In some cases, the target blood glucose level can be adjusted such that the probability of crossing the threshold is the same as the acceptable probability. In these and other cases, the modification of the baseline basal insulin rate can also be based on the actual insulin delivered compared to the BBR for a diurnal period. For example, if four delivery actions occur during a diurnal time period and each of them deliver 2× the BBR, the BBR can be modified based on both the FHI and the 2× delivered. Continuing the example, if a user had selected a low FHI (e.g., the PWD is not as concerned about going low), the target blood glucose level can be changed by a large amount (e.g., between 0% and 5%) while if the user had selected a high FHI (e.g., the PWD is concerned about going low), the BBR can be changed be a smaller amount (e.g., between 0% and 2%). In these and other cases, the change amount can vary depending on whether it is adjusting up or down. For example, for a PWD that prefers high blood glucose levels, methods and systems of the present disclosure can use a larger change when adjusting the BBR upwards and a lower change when adjusting the BBR downwards. In some cases, increases to the target blood glucose level can be unconstrained, but decreases constrained to 5% or less, 3% or less, 2% or less, or 1% or less.

At block X-840, insulin can be delivered based on the modified target blood glucose level. For example, a control device can determine insulin delivery profiles or rates based the target blood glucose level(s) using any suitable method, including the methods described above. In some cases, the delivery of insulin can be based off of one or more insulin delivery profiles that can be generated, and selecting one of the profiles that most closely approximates a target blood glucose level. In these and other cases, the actions of the delivery profiles can be a ratio of the modified BBR. For example, the delivery actions can include one of delivering 0×, 1×, or 2× the modified BBR.

In some cases, the delivery actions of the delivery profiles can be based off of the FHI as well. For example, for a first FHI (e.g., the PWD is concerned about going low), the possible ratios used in the delivery actions of the profile can include 0×, 0.5×, 1× and 1.5× the BBR (e.g., for a PWD that prefers low), while for a second FHI, the possible ratios used in the delivery actions of the profile can include 0×, 1×, 2×, and 3× (e.g., for a PWD that prefers high).

Modifications, additions, or omissions may be made to the method X-800 without departing from the scope of the present disclosure. For example, the operations of the method 800 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 24:
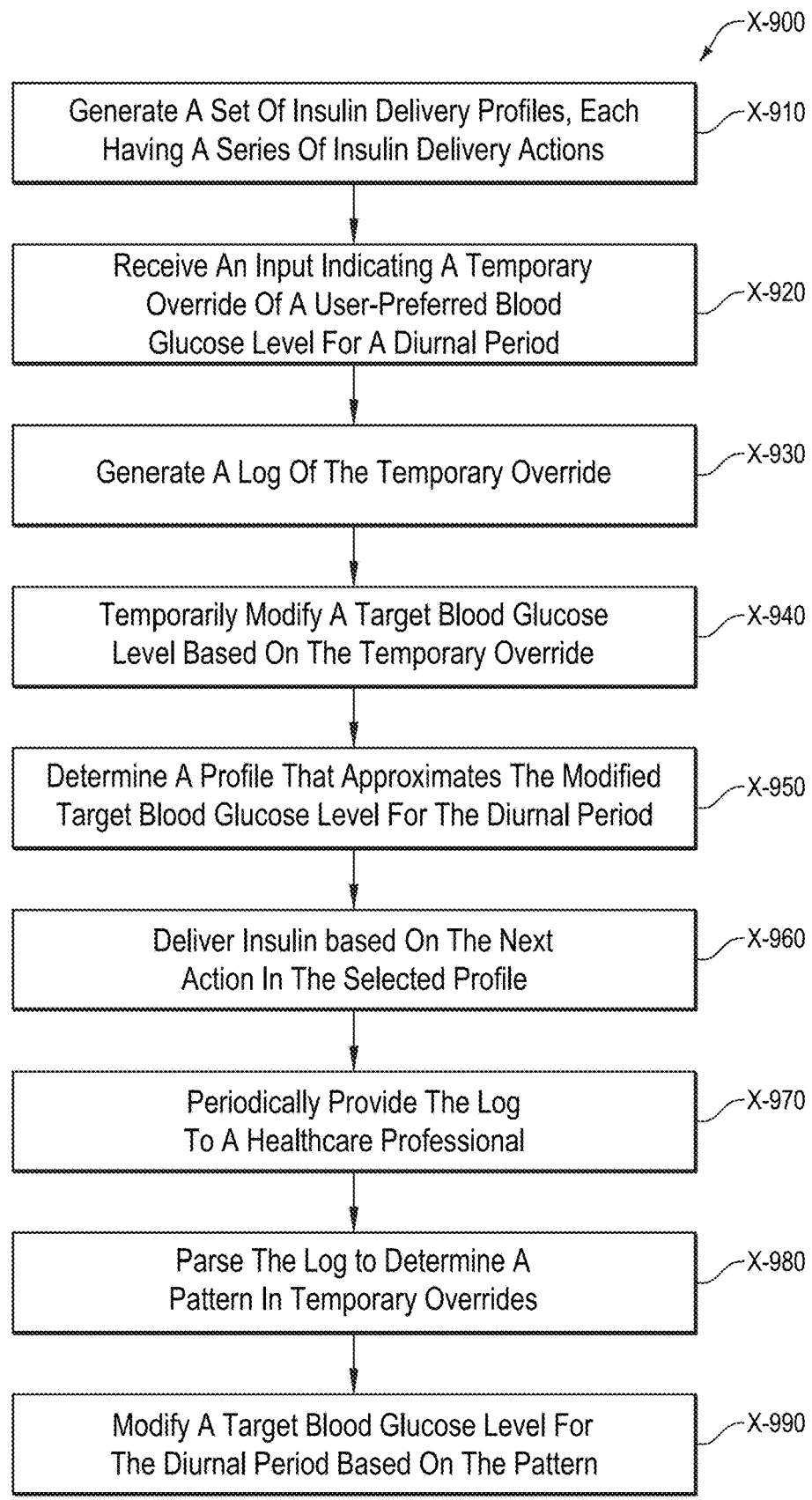
FIG. 24 is a flowchart of an example of utilizing a temporary override associated with methods and systems for delivery of insulin described herein.

FIG. 24 illustrates a flowchart of an example method X-900 of utilizing a temporary override. The method X-900 may be performed by any suitable system, apparatus, or device. For example, the system 10, the pump assembly 15, the mobile computing device 60 of FIG. 1, and/or a remote server may perform one or more of the operations associated with the method X-900. Although illustrated with discrete blocks, the steps and operations associated with one or more of the blocks of the method X-900 may be divided into additional blocks, combined into fewer blocks, or eliminated, depending on the desired implementation.

At block X-910, a set of insulin delivery profiles may be generated, each having a series of insulin delivery actions. For example, an electronic device (e.g., the pump assembly 15, the mobile computing device 60 of FIG. 1 and/or a remote server) may generate a set of profiles in accordance with the present disclosure.

At block X-920, an input indicating a temporary override may be received. The temporary override can indicate a user-preferred blood glucose level for one or more diurnal periods. For example, a user (e.g., a PWD) may be presented with a field or other entry component where the user can enter a numerical blood glucose level for a set period of time. As another example, the user may be presented with multiple activities (e.g., exercising, driving a car for an extended period of time, etc.) and when the activity will be performed. As another example, the user may be presented with a series of textual descriptions of preferred blood glucose levels (e.g., "do not go low," or "do not go high"). In these and other cases, the user may be limited in selecting a temporary override for a period of time some point in the future (e.g., at least thirty minutes in the future).

At block X-930, a log of the temporary override can be generated. For example, the electronic device can record what was selected for the temporary override (e.g., a target blood glucose level, a particular activity, etc.), when, and/or for how long. In some cases, the log may be updated each time the user inputs a temporary override.

At block X-940, a baseline basal insulin rate (BBR) can be temporarily modified based on the temporary override. For example, the BBR can be modified to more closely align the BBR with the user-preferred blood glucose level. For example, the BBR can be adjusted higher if the temporary override indicates a lower than normal blood glucose level. As another example, the BBR can be adjusted lower if the temporary override indicates a higher than normal blood glucose level. In some cases, the temporary override from the block X-920 can be received and the BBR can be modified prior to generating the set of profiles, or the set of profiles can be updated after the temporary override is received and/or the BBR is modified.

At block X-950, a determination can be made as to which profile from the set of profiles approximates the user-preferred blood glucose level during the diurnal period. For example, a predicted blood glucose level for various points in time can be projected based on each of the profiles. The variation from the user-preferred blood glucose level can be analyzed, for example, by accumulating the variation over time and finding the profile with the lowest variation from the user-preferred blood glucose level. In these and other cases, the profile that most closely approximates the user-preferred blood glucose level can be selected as the basis for delivery actions of insulin.

At block X-960, insulin can be delivered based on the next action in the selected profile. For example, a given profile that was selected might have sixteen delivery actions spanning four hours, and the first of sixteen actions may be taken to deliver insulin. In some cases, the block X-960 can include control circuitry or another control device generating a message to be provided to a pump to deliver insulin in accordance with the next action in the selected profile.

At block X-970, the log can be periodically provided to a healthcare professional. For example, the log generated and/or updated at block X-930 can be sent to a healthcare professional using email, text message, via an app, etc., such that the healthcare professional can review the overrides that have occurred for a PWD.

At block X-980, the log can be parsed to determine if a pattern is present in the temporary overrides. For example, the PWD may input a temporary override every Monday, Wednesday, and Friday from 6 PM to 7 PM when they exercise. As another example, the PWD may input a temporary override Monday through Friday from 5:30 PM until 6:15 PM while the PWD drives home from work. The log can be parsed to find such patterns of overrides.

At block X-990, the baseline basal insulin rate can be modified for a given diurnal period based on the pattern. Following the first example given at block X-980, methods and systems of the present disclosure can adjust the BBR for 6 PM to 7 PM on Monday, Wednesday and Friday based on the repeated overrides occurring at those times. Following the second example given at block X-980, methods and systems of the present disclosure can adjust the BBR from 5:30 PM to 6:15 PM Monday through Friday based on the repeated overrides for that span of time.

Modifications, additions, or omissions may be made to the method X-900 without departing from the scope of the present disclosure. For example, the operations of the method X-900 may be implemented in differing order (e.g., the block X-920 can be performed after the block X-910, and/or the blocks X-970 and/or X-980 can be performed any time after the block X-930). Additionally or alternatively, two or more operations may be performed at the same time. Furthermore, the outlined operations and actions are provided as examples, and some of the operations and actions may be optional (e.g., the blocks X-930, X-940, X-970, X-980, and/or X-990), combined into fewer operations and actions, or expanded into additional operations and actions without detracting from the essence of the disclosed embodiments.

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general-purpose or special-purpose computer. By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable media.

Computer-executable instructions comprise, for example, instructions and data which cause a general-purpose computer, special-purpose computer, or special-purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware implementations configured to perform the operations of the module or component and/or software objects or software routines that may be stored on and/or executed by general-purpose hardware (e.g., computer-readable media, processing devices, etc.) of the computing system. In some embodiments, the different components, modules, engines, and services described herein may be implemented as objects or processes that execute on the computing system (e.g., as separate threads). While some of the systems and methods described herein are generally described as being implemented in software (stored on and/or executed by general-purpose hardware), specific hardware implementations or a combination of software and specific hardware implementations are also possible and contemplated. In the present description, a "computing entity" may be any computing system as previously defined herein, or any module or combination of modulates running on a computing system.

Any ranges expressed herein (including in the claims) are considered to be given their broadest possible interpretation. For example, unless explicitly mentioned otherwise, ranges are to include their end points (e.g., a range of "between X and Y" would include X and Y). Additionally, ranges described using the terms "approximately" or "about" are to be understood to be given their broadest meaning consistent with the understanding of those skilled in the art. Additionally, the term approximately includes anything within 10%, or 5%, or within manufacturing or typical tolerances.

All examples and conditional language recited herein are intended for pedagogical objects to aid the reader in understanding the disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosure.

What is claimed is:

1. A method comprising:
   determining available insulin delivery segments for a back-fill time based on a correction bolus;
   determining a cumulative insulin on board (IOB) based on all the available insulin delivery segments being back-filled;
   back-filling a number of the available insulin delivery segments;
   adjusting the number of the available insulin delivery segments that are back-filled until one of the cumulative IOB based on the number of back-filled insulin delivery segments is equal to or less than the correction bolus, or the cumulative insulin of the number of back-filled insulin delivery segments is less than the correction bolus; and
   adjusting a baseline basal rate based on the back-filled insulin delivery segments, the baseline basal rate used for a diurnal time block related to at least a portion of the back-fill time.

2. The method of claim 1, wherein the correction bolus is a negative bolus.

3. The method of claim 1, further comprising configuring an insulin delivery system to deliver insulin during the diurnal time block based on the adjusted baseline basal rate.

4. The method of claim 3, further comprising delivering insulin during the diurnal time block based on the adjusted baseline basal rate.

5. The method of claim 1, wherein the diurnal time block is for a same time of day that covers the portion of the back-fill time on a day later than when the correction bolus is delivered.

6. The method of claim 1, further comprising adjusting one or both of a carbohydrate-to-insulin ratio and an insulin sensitivity factor for the diurnal time block.

7. The method of claim 1, wherein back-filling the number of available insulin delivery segments comprises adjusting at least one insulin delivery action associated with each of the number of available insulin delivery segments.

8. The method of claim 7, wherein the at least one insulin delivery action comprises delivering a dose of insulin that is a multiple or a fraction of a baseline basal insulin.

9. The method of claim 8, further comprising updating historical insulin delivery information based on one or more insulin delivery actions associated with the adjusted number of available insulin delivery segments.

10. A system comprising:
    an insulin delivery device configured to deliver insulin via a plurality of insulin delivery actions over a back-fill time prior to a correction bolus, and deliver the correction bolus; and
    a control device in communication with the insulin delivery device, the control device configured to:
      obtain an amount of insulin delivered in the correction bolus;
      determine available insulin delivery segments for the back-fill time based on which of the plurality of insulin delivery actions delivered less than a maximum amount of insulin relative to a baseline basal rate;
      back-fill a number of the available insulin delivery segments based on an amount of insulin in the correction bolus; and
      adjust a baseline basal rate based on the back-filled insulin delivery segments, the baseline basal rate used for a diurnal time block related to at least a portion of the back-fill time.

11. The system of claim 10, wherein the insulin delivery device delivers insulin during the diurnal time block based on the adjusted baseline basal rate.

12. The system of claim 10, further comprising a user interface, wherein the user interface is configured to display historical insulin delivery information.

13. The system of claim 12, wherein the user interface is configured to update displayed historical insulin delivery information based on one or more insulin delivery actions associated with the number of available insulin delivery segments.

14. The system of claim 13, wherein at least one of the one or more insulin delivery actions is associated with delivering a dose of insulin that is a multiple or a fraction of baseline basal insulin.

15. The system of claim 10, further comprising personalizing the delivery of insulin for a diurnal time period by adjusting one or both of a carbohydrate-to-insulin ratio and an insulin sensitivity factor for the diurnal time block,
    wherein the personalizing is completed after delivering the correction bolus.

* * * * *

UNITED STATES PATENT AND TRADEMARK OFFICE
CERTIFICATE OF CORRECTION

PATENT NO. : 10,583,250 B2  
APPLICATION NO. : 15/870674  
DATED : March 10, 2020  
INVENTOR(S) : Bryan Mazlish, Lane Desborough and Ross Naylor Page 1 of 1

It is certified that error appears in the above-identified patent and that said Letters Patent is hereby corrected as shown below:

In the Specification

| | | |
|---|---|---|
| Column 11, | Line 30, | change "back the mobile" to --back via the mobile-- |
| Column 16, | Line 45, | change "In some embodiments" to --In some embodiments,-- |
| Column 20, | Line 21, | change "In some cases" to --In some cases,-- |
| Column 21, | Line 46, | change "at time j" to --at time j.-- |
| Column 24, | Line 19, | change "to back fill" to --to back-fill-- |
| Column 45, | Line 38, | change "in Block 272," to --in block 272,-- |
| Column 60, | Line 35, | change "method 800 may" to --method X-800 may-- |
| Column 61, | Line 67, | change "given at block" to --given above at block-- |

Signed and Sealed this  
Fifth Day of May, 2020

Andrei Iancu  
*Director of the United States Patent and Trademark Office*